(12) United States Patent
Elliott

(10) Patent No.: US 10,774,039 B2
(45) Date of Patent: Sep. 15, 2020

(54) CYCLOPROPENE AMINO ACIDS AND METHODS

(71) Applicant: United Kingdom Research and Innovation, Swindon (GB)

(72) Inventor: Thomas Elliott, Cambridge (GB)

(73) Assignee: United Kingdom Research and Innovation, Swindon (GB)

( * ) Notice: Subject to any disclaimer, the term of this patent is extended or adjusted under 35 U.S.C. 154(b) by 0 days.

(21) Appl. No.: 15/124,632

(22) PCT Filed: Mar. 10, 2015

(86) PCT No.: PCT/GB2015/050694
§ 371 (c)(1),
(2) Date: Sep. 8, 2016

(87) PCT Pub. No.: WO2015/136265
PCT Pub. Date: Sep. 17, 2015

(65) Prior Publication Data
US 2017/0015623 A1    Jan. 19, 2017

(30) Foreign Application Priority Data
Mar. 14, 2014    (GB) .................................. 1404569.4

(51) Int. Cl.
| C07K 14/00 | (2006.01) |
| C07C 271/22 | (2006.01) |
| C12N 9/36 | (2006.01) |
| C07K 14/435 | (2006.01) |
| C07K 1/107 | (2006.01) |
| C12P 21/02 | (2006.01) |
| C07C 269/06 | (2006.01) |

(52) U.S. Cl.
CPC .......... *C07C 271/22* (2013.01); *C07C 269/06* (2013.01); *C07K 1/1072* (2013.01); *C07K 14/43595* (2013.01); *C12N 9/2462* (2013.01); *C12P 21/02* (2013.01); *C12Y 601/01* (2013.01); *C07C 2601/02* (2017.05)

(58) Field of Classification Search
CPC ....................... A61K 47/48384; C07C 271/22
See application file for complete search history.

(56) References Cited

U.S. PATENT DOCUMENTS

| 7,829,659 | B2 | 11/2010 | Grabstein et al. |
| 9,868,956 | B2 | 1/2018 | Nguyen et al. |
| 9,968,690 | B2 | 5/2018 | Chin et al. |
| 2011/0027829 | A1 | 2/2011 | Neumann et al. |
| 2012/0077186 | A1 | 3/2012 | Skach et al. |
| 2012/0077948 | A1 | 3/2012 | Nguyen et al. |
| 2013/0066063 | A1 | 3/2013 | Berry et al. |
| 2013/0137763 | A1 | 5/2013 | Van Delft et al. |
| 2015/0005481 | A1 | 1/2015 | Chin et al. |
| 2015/0148525 | A1 | 5/2015 | Chin et al. |
| 2015/0259721 | A1* | 9/2015 | Grabstein ............. C07C 271/12 435/34 |
| 2017/0356023 | A1 | 12/2017 | Chin et al. |

FOREIGN PATENT DOCUMENTS

| CN | 104203971 | 12/2014 | |
| EP | 1911840 A1 | 4/2008 | |
| EP | 2192185 A1 | 2/2010 | |
| JP | 2007-514447 A | 6/2007 | |
| WO | WO 2005/003294 A2 | 1/2005 | |
| WO | WO 2006/034332 A2 | 3/2006 | |
| WO | WO 2006/110182 A2 | 10/2006 | |
| WO | WO 2007/090198 A2 | 8/2007 | |
| WO | WO 2008/134761 A2 | 11/2008 | |
| WO | WO 2009/056803 A1 | 5/2009 | |
| WO | WO 2010/139948 A2 | 12/2010 | |
| WO | WO 2011/039518 A2 | 4/2011 | |
| WO | WO 2011/039519 A2 | 4/2011 | |
| WO | WO 2011130616 A1 * | 10/2011 | ........... C07D 487/04 |
| WO | WO-2011130616 A1 * | 10/2011 | ........... C07D 487/04 |
| WO | WO 2011/136645 A1 | 11/2011 | |
| WO | WO 2011/156686 A2 | 12/2011 | |
| WO | WO 2012/104422 A1 | 8/2012 | |
| WO | WO 2012/175924 A2 | 12/2012 | |
| WO | 2013108044 | 7/2013 | |
| WO | WO 2013/171485 A1 | 11/2013 | |
| WO | WO 2015/136265 A1 | 9/2015 | |
| WO | WO 2016/066995 A1 | 5/2016 | |

OTHER PUBLICATIONS

Zhang, Organic Letters, 2006, vol. 8, No. 14, 2965-2968.*
Zhang, Synthesis of Cyclopropene r-Amino Acids via Enantioselective Desymmetrization, Organic Letters 2006, vol. 8, No. 14, of record.*
Patterson, Functionalized Cyclopropenes as Bioorthogonal Chemical Reporters, JACS 2012, 134, 18638-18643.*
Zhang (Synthesis of Cyclopropene r-Amino Acids via Enantioselective Desymmetrization, Organic Letters 2006, vol. 8, No. 14, of record) (Year: 2006).*
Yang (Live-Cell Imaging of Cyclopropene Tags with Fluorogenic Tetrazine Cycloadditions, Angew Chem Int Ed Engl. 2012, 51: 7476-7479) (Year: 2012).*
Patterson (Functionalized Cyclopropenes as Bioorthogonal Chemical Reporters, JACS 2012, 134, 18638-18643, of record) (Year: 2012).*

(Continued)

*Primary Examiner* — Jeanette M Lieb
(74) *Attorney, Agent, or Firm* — Cooley LLP

(57) ABSTRACT

The invention relates to a polypeptide comprising an amino acid having a cyclopropene group wherein said cyclopropene group is joined to the amino acid via a carbamate group. Suitably the cyclopropene group is a 1,3-disubstituted cyclopropene such as a 1,3-dimethylcyclopropene. Suitably the cyclopropene group is present as a residue of a lysine amino acid. The invention also relates to methods of making the polypeptides. The invention also relates to an amino acid comprising cyclopropene wherein said cyclopropene group is joined to the amino acid moiety via a carbamate group.

18 Claims, 17 Drawing Sheets

Specification includes a Sequence Listing.

(56) References Cited

OTHER PUBLICATIONS

Elliott, Thomas et al. "Proteome labeling and protein identification in specific tissues and at specific developmental stages in an animal" Nature Biotechnology, vol. 32, No. 5, pp. 465-472.
Fuhr, Christian "International Search Report and Written Opinion—International Application No. PCT/GB2015/050694" European Patent Office; dated May 18, 2015; pp. 1-14.
Sachdeva, Amit, et al. "Concerted, Rapid, Quantitative, and Site-Specific Dual Labeling of Proteins" Journal of the American Chemical Society, 2014, 136, pp. 7785-7788.
Schmied, Wolfgang H., et al. "Efficient Multisite Unnatural Amino Acid Incorporation in Mammalian Cells via Optimized Pyrrolysyl tRNA Synthetase/tRNA Expression and Engineered eRF1" Journal of the American Chemical Society, 2014, 136, pp. 15577-15583.
Yu, Zhipeng, et al. "Genetically Encoded Cyclopropene Directs Rapid, Photoclick-Chemistry-Mediated Protein Labeling in Mammalian Cells" Angew. Chem. Int. Ed. 2012, 51, pp. 10600-10604.
Wang, Li, "First Office Action—China Application No. 2019030601667810" China Patent Office; dated Feb. 28, 2019.
Zhipeng Yu, et al., "Design of Spiro[2.3]hex-1-ene, a Genetically Encodable Double-Strained Alkene for Superfast Photoclick Chemistry" Journal of American Chemical Society 2014, 136, pp. 4153-4156, S1-S82.
Agard, et al., "A Strain-Promoted [3+2] Azide-Alkyne Cycloaddition for Covalent Modification of Biomolecules in Living Systems". J. Am. Chem. Soc., vol. 126:15046-15047 (Nov. 2, 2004).
Barker, et al.,Barker—"Tetrazine-Norbornene Click Reactions to Functionalize Degradable Polymers Derived from Lactide" Macromol, Rapid Commun. (2011); 32(17), pp. 1362-1366.
Bianco, et al. "Expanding the genetic code of Drosophila melanogaster" Nature Chemical Biology (Sep. 2012); 8(9); pp. 748-750.
Blackman, et al. "Tetrazine Ligation: Fast Bioconjugation Based on Inverse-Electron-Demand Diels-Alder Reactivity" J. Am. Chem. Soc., 2008, vol. 130, pp. 13518-13519.
Blight, et al. "Direct charging of tRNAcua with pyrrolysine in vitro and in vivo" Nature, vol. 43, Sep. 16, 2004, pp. 333-335.
Bulygin, et al., "Three distinct peptides from the N domain of translation termination factor eRF1 surround stop codon in the ribosome" RNA (2010), 16: 1902-1914.
Canalle, et al., "Clickable Enzyme-linked Immunosorbent Assay". BioMacromolecules (2011); vol. 12: 3692-3697.
Chen, et al., "Clicking 1,2,4,5-tetrazine and cyclooctynes with tunable reaction rates", Chem. Commun,. vol. 48:1736-1738 (online Nov. 24, 2011).
Chin, Jason W., "Expanding and Reprogramming the Genetic Code of Cells and Animals", Annu. Rev., Biochem. (2014); 83: 379-408.
Chin, "Reprogramming the genetic code" EMBO Journal, vol. 30:2312-2324 (2011).
Davis et al., "Designer proteins: applications of genetic code expansion in cell biology", Nature Reviews Molecular Cell Biology, vol. 13: 168-182 (Mar. 2012).
Devaraj, et al. "Tetrazine-Based Cycloadditions: Application to Pretargeted Live Cell Imaging" Bioconjugate Chem. (2008); 19(12); pp. 2297-2299.
Dommerholt, et al., "Readily Accessible Bicyclononynes for Bioorthogonal Labeling and Three-Dimensional Imaging of Living Cells", Angew. Chem. Int. Ed., vol. 49:9422-9425 (Dec. 3, 2010).
Elliott, Thomas S., et al. "Proteome labeling and protein identification in specific tissues and at specific D developmental stages in an animal", Nature Biotechnology, vol. 32, No. 5, May 2014.
Fekner, et al., "A Pyrrolysine Analogue for Protein Click Chemistry". Angew Chem Int Ed Engl. (2009); 48(9): 1633-1635.
Gaston, et al. "The complete biosynthesis of the genetically encoded amino acid pyrrolysine from lysine" Nature, vol. 471, No. 7340, Mar. 31, 2011, pp. 647-650.
Hao, et al A readily synthesized cyclic pyrrolysine analogue for site-specific protein "click labeling" Chem. Commun.(2011); 47: 4502-4504.

Ilegems, Erwin, et al. "Downregulation cif eRFI by RNA interference increases mis-acylated tRNA suppression efficiency in human cells" Protein Engineering, Design & Selection, vol. 17, No. 12, pp. 821-827, 2004.
International Search Report and Written Opinion in International Application No. PCT/GB2013/051249, dated Oct. 14, 2013, 15 pages.
International Search Report and Written Opinion in International Application No. PCT/GB2010/001083, dated Mar. 28, 2011, 16 pages.
International Search Report and Written Opinion in International Application No. PCT/GB2015/053141 dated Feb. 2, 2016, 12 pages.
International Search Report and Written Opinion in International Application No. PCT/GB2015/050694, dated May 22, 2015, 12 pages.
International Search Report and Written Opinion for International Application No. PCT/GB2013/050121 dated Oct. 9, 2013, 20 pages.
International Preliminary Report on Patentability in International Application No. PCT/GB2015/053141 dated Feb. 3, 2017, 17 pages.
International Preliminary Report on Patentability in International Application No. PCT/GB2015/050694, dated Sep. 14, 2016, 8 pages.
International Preliminary Report on Patentability in International Application No. PCT/GB2013/051249, dated Nov. 18, 2014, 9 pages.
International Preliminary Report on Patentability in International Application No. PCT/GB2010/001083, dated Dec. 6, 2011, 9 pages.
International Preliminary Report on Patentability for International Application No. PCT/GB2013/050121 dated Jul. 22, 2014, 11 pages.
Kaya, et al. "A Genetically Encoded Norbornene Amino Acid for the Mild and Selective Modification of Proteins in a Copper-Free Click Reaction" Angew. Chem. Int. Ed. (2012); 571(18), pp. 4466-4469.
Koglin, et al., "Facile and Selective Nanoscale Labeling of Peptides in Solution by Using Photolabile Protecting Groups", J. Med. Chem., vol. 46:4369-4372 (2003).
Kolosov, et al., "Invariant amino acids essential for decoding function of polypeptide release factor eRF1", Nucleic Acids Research (2005); vol. 33, No. 19; pp. 6418-6425.
Kryuchkova, P., "Two-step model of stop codon recognition by eukaryotic release factor eRF1", Nucleic Acids Research (2013); vol. 41, No. 8, pp. 4573-4586.
Krzycki, et al. "The direct genetic encoding of pyrrolysine", Current Opinion in Microbiology, Current Biology Ltd, GB., vol. 8, No. 6, Dec. 1, 2005, pp. 706-712.
Lang, et al. "Genetic Encoding of Bicyclononynes and trans-Cyclooctenes for Site-Specific Protein Labeling in Vitro and in Live Mammalian Cells via Rapid Flurogenic Diels-Alder Reactions" J. Am. Chem. Soc. (2012); 134, pp. 10317-10320.
Lang, et al. "Genetically encoded norbornene directs site-specific cellular protein labelling via a rapid bioorthogonal reaction" Nature Chemistry (Apr. 2012); vol. 4, No. 4; Apr. 1, 2012, pp. 298-304.
Lekomtsev, S., et al., "Different modes of stop codon restriction by the Stylonychia and Paramecium eRF1 translation termination factors" PNAS (2007); vol. 104, No. 26; pp. 10824-10829.
Li, et al., "A Pyrrolysine Analogue for Site-Specific Protein Ubiquitination". Angew Chem Int Ed Engl. (2009); 48(48): 9184-9187.
Malito, et al., Crystal structure of a Baeyer-Villiger monooxygenase, PNAS, vol. 101 (36): 13157-13162 (Sep. 7, 2004) (Year: 2004).
Meeuwissen, et al., Cofactor regeneration in polymersome nanoreactors: enzymatically catalysed Baeyer-Villiger reactions. J. Mater. Chem. (2011); vol. 21: 18923-18926 and pp. 1-14 of Supplemental Information (Sep. 12, 2011).
Mukai, et al., "Adding L-lysine derivatives to the genetic code of mammalian cells with engineered pyrrolysyl-tRNA synthetases", Biochemical and Biophysical Research Communications (Jul. 11, 2008); vol. 371, Issue 4, pp. 818-822.
Nuemann, et al., "Genetically encoding N(epsilon)-acetyllysine in recombinant proteins", Nat Chem Biol. (Apr. 2008); 4(4): 232-234.

(56) References Cited

OTHER PUBLICATIONS

Nguyen, et al., "Genetic Encoding and Labeling of Aliphatic Azides and Alkynes in Recombinant Proteins via a Pyrrolysyl-tRNA Synthetase/ tRNACUA Pair and Click Chemistry". J Am Chem Soc. (Jul. 1, 2009); 131(25): 8720-8721.

Nozawa, et al., "Pyrrolysyl-tRNA synthetase:tRNAPyl structure reveals the molecular basis of orthogonality". Nature (Feb. 26, 2009); 457(7233): 1163-1167.

Plass, et al., "Amino Acids for Diels-Alder Reactions in Living Cells" Angew. Chem. Int. Ed. (2012); 51(17), pp. 4166-4170.

Prescher and Bertozzi, "Chemistry in living systems", Nature Chemical Biology (2005); vol. 1, No. 1, pp. 13-21.

Schmied, Wolfgang, H., et al. "Efficient Multisite Unnatural Amino Acid Incorporation in Mammalian Cells via 7 Optimized Pyrrolysyl tRNA Synthetase/tRNA Expression and Engineered eRF1" J. Am. Chem. Soc., 2014, 136, 15577-15583.

Seit-Nebi, Alim, et al. "Conversion of omnipotent translation termination factor eRF1 into ciliate-like UGA-only unipotent eRF1" European Molecular Biology Organization, vol. 3, No. 9; pp. 881-886, 2002.

Sletten and Bertozzi, "Bioorthogonal Chemistry: Fishing for Selectivity in a Sea of Functionality" Angew. Chem. Int. Ed. (2009); 48(38), pp. 6974-6998.

Strable, et al., "Unnatural Amino Acid Incorporation into Virus-Like Particles". Bioconjug Chem. (Apr. 2008); 19(4): 866-875. Epub Mar. 5, 2008.

[Author Unknown] ThermoFisher Scientific, Amine-Reactive Crosslinker Chemistry, Thermo Fisher Scientific, ThermoFisher. com, attached as pdf, 8 pages (Apr. 18, 2012). (cited in U.S. Appl. No. 14/401,803 by the Examiner as having a published date of Apr. 18, 2012).

Virdee, et al. "Traceless and Site-Specific Ubiquitination of Recombinant Proteins" J. Am. Chem. Soc., 2011, vol. 133, pp. 10708-10711.

Yanagisawa, et al, "Multistep engineering of pyrrolysyl-tRNA synthetase to genetically encode N(epsilon)-(oazidobenzyloxycarbonyl)lysine for site-specific protein modification", Chem & Biol. (Nov. 24, 2008); 15(11): 1187-1197.

Zeglis, et al., "Modular Strategy for the Construction of Radiometalated Antibodies for Positron Emission Tomography Based on Inverse Electron Demand Diels-Alder Click Chemistry" Bioconjugate Chem. (2011); 22(10), pp. 2048-2059.

Ambrogelly, et al., "Pyrrolysine is not hardwired for cotranslational insertion at UAG codons," Proc. Natl. Acad. Sci. USA (2007); 104(9):3141-3146.

Kiick,et al., "Incorporation of azides into recombinant proteins for chemoselective modification by the Staudinger ligation," Proc. Natl. Acad. Sci. USA (2002); 99(1): 19-24.

Polycarpo, et al., "An aminoacyl-tRNA synthetase that specifically activates pyrrolysine," Proc. Natl. Acad. Sci. USA (2004); 101(34): 12450-12454.

Xie and Schultz, "Adding amino acid to the genetic repertoire", Current Opinion in Chemical Biology (2005); 9: 548-554.

* cited by examiner

FIG. 2C
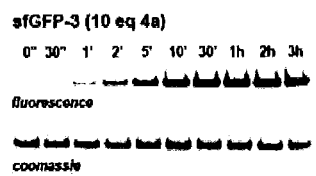
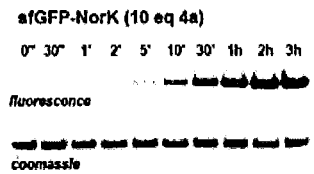
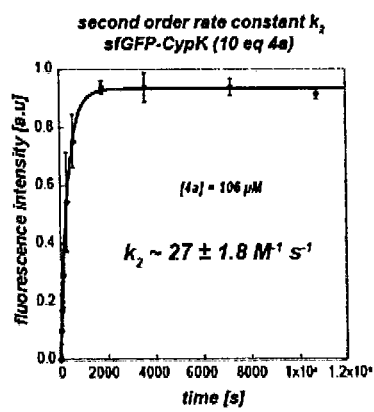
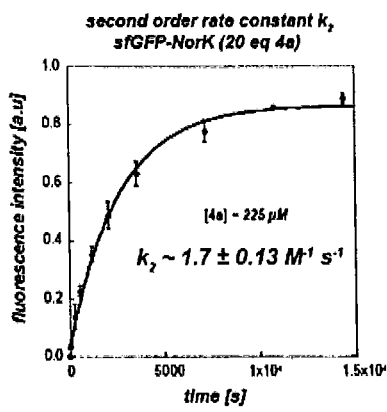

FIG. 3

| Name | Sequence | Notes |
|---|---|---|
| FMT17 | SEQ. ID NO. 18:<br>CATGTAGATCGAATGGACTATAAATC<br>CGTTCAGCCGGG | Mutagenesis primers for D.m.<br>PylT |
| FMT18 | SEQ. ID NO. 19:<br>CCCGGCTGAACGGATTTATAGTCCATT<br>CGATCTACATG | CTA to ATA (Tyr) |
| FMT19 | SEQ. ID NO. 20:<br>CATGTAGATCGAATGGACTTGCAATC<br>CGTTCAGCCGGGTTAG | Mutagenesis primers for D.m.<br>PylT |
| FMT20 | SEQ. ID NO. 21:<br>CTAACCCGGCTGAACGGATTGCAAGT<br>CCATTCGATCTACATG | CTA to TGC (Ala) |
| FMT21 | SEQ. ID NO. 22:<br>GTAGATCGAATGGACTAGAAATCCGT<br>TCAGCCGGG | Mutagenesis primers for D.m.<br>PylT |
| FMT22 | SEQ. ID NO. 23:<br>CCCGGCTGAACGGATTTCTAGTCCATT<br>CGATCTAC | CTA to AGA (Ser) |
| FMT23 | SEQ. ID NO. 24:<br>CATGTAGATCGAATGGACTGCTAATC<br>CGTTCAGCCGGGTTAG | Mutagenesis primers for D.m.<br>PylT |
| FMT24 | SEQ. ID NO. 25:<br>CTAACCCGGCTGAACGGATTAGCAGT<br>CCATTCGATCTACATG | CTA to GCT (Ser) |
| FMT25 | SEQ. ID NO. 26:<br>GTAGATCGAATGGACTTAAAATCCGT<br>TCAGCCGGG | Mutagenesis primers for D.m.<br>PylT |
| FMT26 | SEQ. ID NO. 27:<br>CCCGGCTGAACGGATTTTAAGTCCATT<br>CGATCTAC | CTA to TAA (Leu) |
| FMT27 | SEQ. ID NO. 28:<br>GTAGATCGAATGGACTCAGAATCCGT<br>TCAGCCGGG | Mutagenesis primers for D.m.<br>PylT |
| FMT28 | SEQ. ID NO. 29:<br>CCCGGCTGAACGGATTCTGAGTCCAT<br>TCGATCTAC | CTA to CAG (Leu) |
| FMT29 | SEQ. ID NO. 30:<br>GTAGATCGAATGGACTCATAATCCGT<br>TCAGCCGGG | Mutagenesis primers for D.m.<br>PylT |
| FMT30 | SEQ. ID NO. 31:<br>CCCGGCTGAACGGATTATGAGTCCAT<br>TCGATCTAC | CTA to CAT (Met) |
| FMT31 | SEQ. ID NO. 32:<br>CATGTAGATCGAATGGACTTTTAATCC<br>GTTCAGCCGGGTTAG | Mutagenesis primers for D.m.<br>PylT |
| FMT32 | SEQ. ID NO. 33:<br>CTAACCCGGCTGAACGGATTAAAAGT<br>CCATTCGATCTACATG | CTA to TTT (Lys) |
| MAM01 | SEQ. ID NO. 34:<br>GTAGATCGAATGGACTCATAATCCGT<br>TCAGCCGGG | Forward mutagenesis primer for<br>CTA to CAT (Met) |
| MAM02 | SEQ. ID NO. 35:<br>CCCGGCTGAACGGATTATGAGTCCAT<br>TCGATCTAC | Reverse mutagenesis primer for<br>CTA to CAT (Met) |

FIG. 3 (continued)

| Name | Sequence | Notes |
|---|---|---|
| MAM03 | SEQ. ID NO. 36:<br>GATCGAATGGACTCACAATCCGTTCAGCCGG | Forward mutagenesis primer for CTA to CAC (Val) |
| MAM04 | SEQ. ID NO. 37:<br>CCGGCTGAACGGATTGTGAGTCCATTCGATC | Reverse mutagenesis primer for CTA to CAC (Val) |
| MAM05 | SEQ. ID NO. 38:<br>GATCGAATGGACTCTTAATCCGTTCAGCCG | Forward mutagenesis primer for CTA to CTT (Lys) |
| MAM06 | SEQ. ID NO. 39:<br>CGGCTGAACGGATTAAGAGTCCATTCGATC | Reverse mutagenesis primer for CTA to CTT (Lys) |
| MAM07 | SEQ. ID NO. 40:<br>GATCGAATGGACTCTCAATCCGTTCAGCCG | Forward mutagenesis primer for CTA to CTC (Glu) |
| MAM08 | SEQ. ID NO. 41:<br>CGGCTGAACGGATTGAGAGTCCATTCGATC | Reverse mutagenesis primer for CTA to CTC (Glu) |
| MAM09 | SEQ. ID NO. 42:<br>GTAGATCGAATGGACTGTAAATCCGTTCAGCCG | Forward mutagenesis primer for CTA to GTA (Tyr) |
| MAM10 | SEQ. ID NO. 43:<br>CGGCTGAACGGATTTACAGTCCATTCGATCTAC | Reverse mutagenesis primer for CTA to GTA (Tyr) |
| MAM11 | SEQ. ID NO. 44:<br>GATCGAATGGACTCCAAATCCGTTCAGCCG | Forward mutagenesis primer for CTA to CCA (Trp) |
| MAM12 | SEQ. ID NO. 45:<br>CGGCTGAACGGATTTGGAGTCCATTCGATC | Reverse mutagenesis primer for CTA to CCA (Trp) |

Anti-FLAG        ANTI-HA        TAMRA- imaging

ANTI-HA        ANTI-HA    FLUORESCENCE

FIG. 15

```
atggtgtccaagggcgaggagctgtttaccggcgtggtgcccattctggtggagctggat
 M  V  S  K  G  E  E  L  P  T  G  V  V  P  I  L  V  E  L  D
ggcgacgtgaacggccacaagttcagcgtgtccggcgagggcgagggcgacgccacctat
 G  D  V  N  G  H  K  F  S  V  S  G  E  G  E  G  D  A  T  Y
ggaaagctgaccctgaagttcatctgcaccaccggcaagctgcccgtgccatggccaacc
 G  K  L  T  L  K  F  I  C  T  T  G  K  L  P  V  P  W  P  T
ctcgtgaccaccctgacctatggcgtgcagtgcttcagccgctaccccgatcacatgaag
 L  V  T  T  L  T  Y  G  V  Q  C  F  S  R  Y  P  D  H  M  K
cagcacgatttcttcaagagcgccatgcccgagggctacgtgcaggagcgcaccatcttt
 Q  H  D  F  F  K  S  A  M  P  E  G  Y  V  Q  E  R  T  I  F
ttcaaggatgacggcaactacaagacccgcgccgaagtgaagttcgagggcgatacccta
 F  K  D  G  N  Y  K  T  R  A  E  V  K  F  E  G  D  T  L
gtgaaccgcatcgagctgaagggcatcgatttcaaggaggatggaaacatcctgggccac
 V  N  R  I  E  L  K  G  I  D  F  K  E  D  G  N  I  L  G  H
aagctggagtacaactacaacagccacaacgtgtacatcatggccgacaagcagaagaac
 K  L  E  Y  N  Y  N  S  H  N  V  Y  I  M  A  D  K  Q  K  N
ggcatcaaagtgaacttcaagatccgccacaacatcgaggatggcagcgtgcagctggcc
 G  I  K  V  N  F  K  I  R  H  N  I  E  D  G  S  V  Q  L  A
gatcactaccagcagaacacccccatcggcgacggccccgtgctgctgcccgataaccat
 D  H  Y  Q  Q  N  T  P  I  G  D  G  P  V  L  L  P  D  N  H
tacctgagcacccagagcgccctgagcaaggaccccaacgagaagcgcgacaacatggtg
 Y  L  S  T  Q  S  A  L  S  K  D  P  N  E  K  R  D  H  M  V
ctgctggagtttgtgaccgccgccggcattaccctgggcatggatgagctgtacaagcgc
 L  L  E  F  V  T  A  A  G  I  T  L  G  M  D  E  L  Y  K  R
gcccagatccacgatctggtgtaggtgggaggatcgaccgcgtgtcgaagggcgaggag
 A  Q  I  H  D  L  V  -  V  G  G  S  T  R  V  S  K  G  E  E
gataacatggccatcatcaaggagttcatgcgcttcaaggtgcacatggagggctccgtg
 D  N  M  A  I  I  K  E  F  M  R  F  K  V  H  M  E  G  S  V
aatggacacgagttcgagattgagggcgagggcgagggacgcccatatgagggaaccaag
 N  G  H  E  F  E  I  E  G  E  G  E  G  R  P  Y  E  G  T  Q
accgccaagctgaaagtgaccaagggcggaccctgcccttcgcctgggatatctgagc
 T  A  K  L  K  V  T  K  G  G  P  L  P  F  A  W  D  I  L  S
ccccagtttatgtacggcagcaaggcctacgtgaagcaccccgccgatatccccgattac
 P  Q  F  M  Y  G  S  K  A  Y  V  K  H  P  A  D  I  P  D  Y
ctgaagctgagcttcccagagggcttcaagtgggagcgcgtgatgaatttcgaggacggc
 L  K  L  S  F  P  E  G  F  K  W  E  R  V  M  N  F  E  D  G
ggagtcgtgaccgtgacccaggatagcagtttgcaggatggcgagttcatctacaaagtg
 G  V  V  T  V  T  Q  D  S  S  L  Q  D  G  E  F  I  Y  K  V
aagctgcgcggcaccaacttccccgtccgatggcccagtgatgcagaagaagccatggga
 K  L  R  G  T  N  F  P  S  D  G  P  V  M  Q  K  K  T  M  G
tgggaggccagcagcgagcgcatgtatcccgaggatggcgccctgaagggcgagatcaag
 W  E  A  S  S  E  R  M  Y  P  E  D  G  A  L  K  G  E  I  K
cagcgcctgaagctgaaggatggcggccactacgatgccgaagtgaagaccacctacaag
 Q  R  L  K  L  K  D  G  G  H  Y  D  A  E  V  K  T  T  Y  K
gccaagaagcccgtgcagctgcccggcgcctacaatgtgaacatcaagctggatatcacc
 A  K  K  P  V  Q  L  P  G  A  Y  N  V  N  I  K  L  D  I  T
tcccacaacgaggactacaccatcgtggagcagtatgagcgcgccgagggccgccatagt
 S  H  N  E  D  Y  T  I  V  E  Q  Y  E  R  A  E  G  R  H  S
accggcggaatggacgagctgtataagatgtaccctacgatgtgcccgattagccgag
 T  G  G  M  D  E  L  Y  K  M  Y  P  Y  D  V  P  D  Y  A  E
cagaagctgatctccgaggaggacctgcaccatcaccaccaccggaagtggcagcggc
 Q  K  L  I  S  E  E  D  L  H  H  H  H  H  H  G  S  G  S  G
tccccaaagaagaagcgcaaggtgtaa
 S  P  K  K  K  R  K  V  -
```

CYCLOPROPENE AMINO ACIDS AND METHODS

CROSS-REFERENCE TO RELATED APPLICATIONS

This application is a national stage entry under 35 U.S.C. 371 of International Application PCT/GB2015/050694 filed Mar. 10, 2015. International Application PCT/GB2015/050694 cites the priority of British Patent Application 1404569.4, filed on Mar. 14, 2014.

FIELD OF THE INVENTION

The invention relates to site-specific incorporation of bio-orthogonal groups via the (expanded) genetic code. In particular the invention relates to incorporation of carbamate-bonded cyclopropenes into polypeptides via genetically incorporated amino acids such as lysines. Such cyclopropene groups are useful for addition of further chemical groups such as tetrazines.

BACKGROUND TO THE INVENTION

The site-specific incorporation of bio-orthogonal groups via genetic code expansion provides a powerful general strategy for site specifically labelling proteins with any probe. However, the slow reactivity of the bio-orthogonal functional groups that can be genetically encoded, and/or their need for photoactivation, has limited this strategy's utility.

The rapid, site-specific labeling of proteins with diverse probes remains an outstanding challenge for chemical biologists; enzyme mediated labeling approaches may be rapid, but use protein or peptide fusions that introduce perturbations into the protein under study and may limit the sites that can be labeled, while many 'bio-orthogonal' reactions for which a component can be genetically encoded are too slow to effect the quantitative and site specific labeling of proteins on a time-scale that is useful to study many biological processes.

There is a pressing need for general methods to site-specifically label proteins, in diverse contexts, with user-defined probes.

Inverse electron demand Diels-Alder reactions involving tetrazines have emerged as an important class of rapid bio-orthogonal reactions. The rates reported for some of these reactions are very fast.

Yu et al 2012 (Angew. Chem. Int. Ed. Volume 51, pages 10600-10604) disclose Genetically Encoded Cyclopropene Directs Rapid, Photoclick Chemistry Mediated Protein Labelling in Mammalian Cells. The authors report the synthesis of a stable cyclopropene amino acid, the characterisation of its reactivity in a photo induced cycloaddition reaction with two tetrazoles, its site-specific incorporation into proteins both in *E. coli* and in mammalian cells, and its use in directing bioothogonal labelling of proteins both in vitro and in vivo. In order to incorporate their cyclopropene containing amino acid into proteins, the authors had to evolve an orthogonal tRNA/tRNA synthetase pair that selectively charges their cyclopropene lysine amino acid in response to a TAG amber codon. This required a synthetase library to be constructed, five positions within that synthetase to be randomised, together with at least five rounds of positive and negative selection screening. It is a drawback of this work that it relies on the specific mutant synthetase produced. In joining their tetrazole compounds to the cyclopropene moiety in their modified amino acids, Yu et al use photo activation. Photo activation is carried out at either 302 nano metres or 365 nano metres. The requirement for photo activation in joining tetrazoles to the amino acid of Yu et al is a drawback in the art. This is a laborious extra step in the conjugation chemistry. UV is also damaging to cells and so is disadvantageous in the in vivo/cellular setting.

Kamber et al disclose Isomeric Cyclopropenes Exhibiting Unique Bioorthogonal Reactivities (2013 JACS Volume 135, pages 13680-13683). The authors discuss two reactions that can be used to tag biomolecules in complex environments: the inverse electron demand Diels-Alder reaction of tetrazines with 1,3-disubstituted cyclopropenes, and the 1,3-dipolar cycloaddition of nitrile imines with 3,3-disubstituted cyclopropenes. The authors discuss various chemical reaction schemes used to generate stable cyclo adducts. None of the molecules discussed by Kamber et al are amino acids. There is no reason to imagine that the compounds as described could be incorporated into amino acids. Even if any such incorporation was attempted, there is absolutely no suggestion or guidance which might allow such compounds to be incorporated into polypeptides. No schemes for synthesis of amino acids comprising any of the chemical groups described are presented by Kamber et al. There are no biochemical tools for incorporation into proteins mentioned anywhere in this document. Kamber et al are solely concerned with examining the substitution pattern on the cyclopropene, one such pattern allowing reactions with tetrazines and one such pattern not being permissive of reactions with tetrazines.

The present invention seeks to overcome problem(s) associated with the prior art.

SUMMARY OF THE INVENTION

In one aspect the invention provides a polypeptide comprising an amino acid having a cyclopropene group wherein said cyclopropene group is joined to the amino acid via a carbamate group.

Suitably said cyclopropene group is a 1,3-disubstituted cyclopropene. Suitably said cyclopropene is a 1,3-dimethylcyclopropene. Suitably said cyclopropene group is present as a residue of a lysine amino acid. Suitably said polypeptide further comprises a tetrazine compound linked to said cyclopropene group.

In another aspect, the invention relates to an amino acid comprising cyclopropene wherein said cyclopropene group is joined to the amino acid moiety via a carbamate group.

Suitably said cyclopropene is a 1,3-disubstituted cyclopropene. Suitably said cyclopropene is a 1,3-dimethylcyclopropene. Suitably said amino acid is a lysine amino acid. Suitably said amino acid comprises $N^\varepsilon$-[((2-methylcycloprop-2-en-1-yl)methoxy)carbonyl]-1-lysine.

Suitably said amino acid comprises, or more suitably consists of:

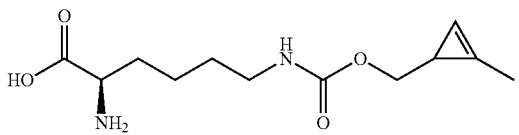 [SMILES: CC1=CC1COC(=O)NCCCC[C@@H](N)C(=O)O]

In another aspect, the invention relates to a method of producing a polypeptide comprising a cyclopropene group wherein said cyclopropene group is joined to the amino acid moiety via a carbamate group, said method comprising genetically incorporating an amino acid comprising a cyclopropene group joined to the amino acid moiety via a carbamate group, into a polypeptide.

Suitably producing the polypeptide comprises (i) providing a nucleic acid encoding the polypeptide which nucleic acid comprises an orthogonal codon encoding the amino acid having a cyclopropene group;

(ii) translating said nucleic acid in the presence of an orthogonal tRNA synthetase/tRNA pair capable of recognising said orthogonal codon and incorporating said amino acid having a cyclopropene group into the polypeptide chain.

Suitably said orthogonal codon comprises an amber codon (TAG), said tRNA comprises MbtRNA$_{CUA}$ and said tRNA synthetase comprises MbPylRS.

Suitably said orthogonal codon comprises an amber codon (TAG), said tRNA comprises MmtRNA$_{CUA}$ and said tRNA synthetase comprises MmPylRS.

In another aspect, the invention relates to a method as described above wherein said amino acid comprising a cyclopropene group is an amino acid as described above.

In another aspect, the invention relates to a method of producing a polypeptide comprising a tetrazine group, said method comprising providing a polypeptide comprising a cyclopropene group as described above, contacting said polypeptide with a tetrazine compound, and incubating to allow joining of the tetrazine to the cyclopropene group by an inverse electron demand Diels-Alder cycloaddition reaction.

Suitably said reaction is allowed to proceed for 10 minutes or less, preferably for 1 minute or less, preferably for 30 seconds or less. Reactions in vivo, or in eukaryotic culture conditions such as tissue culture medium or other suitable media for eukaryotic cells, may need to be conducted for longer than 30 seconds to achieve maximal labelling. The skilled operator can determine optimum reaction times by trial and error based on the guidance provided herein.

In another aspect, the invention relates to a polypeptide as described above wherein said polypeptide comprises two or more amino acids each having a cyclopropene group, wherein each said cyclopropene group is joined to each said amino acid via a carbamate group. Provision of two or more cyclopropene groups on the polypeptide advantageously allows joining of two or more conjugated groups (functional groups) to the polypeptide. This is especially helpful when the conjugated groups (functional groups) comprise drug molecules such as cytotoxic molecules such as in an antibody-drug-conjugate.

Suitably said polypeptide comprises four amino acids each having a cyclopropene group.

Suitably the antibody drug conjugate (ADC) comprising a polypeptide as described above comprises four amino acids each having a cyclopropene group. This is especially advantageous for the joining of four cytotoxic molecules to the ADC of interest.

In another aspect, the invention relates to an antibody drug conjugate (ADC) comprising a polypeptide as described above. Suitably the polypeptide is an antibody polypeptide such as whole antibody (e.g. a monoclonal antibody (mAb)) or is an antibody fragment (e.g. a single-chain variable fragment [scFv]), suitably an antibody fragment comprising CDR amino acid sequence.

Suitably the antibody polypeptide (or fragment) may advantageously be humanised by manufacture of chimaeric antibody polypeptide(s); suitably the antibody polypeptide (or fragment) may advantageously be CDR-grafted; suitably the antibody polypeptide (or fragment) may advantageously be fully humanised to the extent that the technology permits.

Suitably the antibody polypeptide (or fragment) may be fused to another polypeptide of interest such as such as a ligand for the transferrin receptor, for example transferrin or a part thereof, to assist in transport and/or targeting of the ADC.

In another aspect, the invention relates to a polypeptide as described above wherein said tetrazine group is further joined to a fluorophore.

Suitably said fluorophore comprises fluorescein, tetramethyl rhodamine (TAMRA) or boron-dipyrromethene (BODIPY).

Suitably said fluorophore may comprise one or more Alexa fluorophore(s). Suitably said fluorophore may comprise one or more Cyanine based fluorophore(s).

DETAILED DESCRIPTION

Genetic code expansion methods allow the quantitative, site-specific, and genetically directed incorporation of unnatural amino acids with diverse chemical structures and bearing diverse functional groups. This is most commonly achieved by inserting the unnatural amino acid in response to an amber stop codon introduced into a gene of interest.[12,13] Genetic code expansion is achieved via the introduction of an orthogonal aminoacyl-tRNA synthetase/tRNA$_{CUA}$ pair into cells. The pyrrolysyl-tRNA synthetase/tRNA$_{CUA}$ pair is amongst the most useful pairs for genetic code expansion,[13] because it 1) can specifically recognize a range of useful unnatural amino acids, 2) can be evolved to recognize an extended range of chemical structures, and 3) can be used as an orthogonal pair for genetic code expansion in *E. coli*,[14] yeast,[15] mammalian cells,[16-18] *C. elegans*[19] and *D. melanogaster*.[20]

We demonstrate production of newly synthesized proteins with cyclopropene groups that can be labelled with tetrazine probes introduced via a chemoselective inverse electron demand Diels-Alder reaction.

In another aspect, the invention relates to a homogenous recombinant polypeptide as described above. Suitably said polypeptide is made by a method as described above.

Also disclosed is a polypeptide produced according to the method(s) described herein. As well as being the product of those new methods, such a polypeptide has the technical feature of comprising cyclopropene suitably carbamate-linked cyclopropene.

Mutating has it normal meaning in the art and may refer to the substitution or truncation or deletion of the residue, motif or domain referred to. Mutation may be effected at the polypeptide level e.g. by synthesis of a polypeptide having the mutated sequence, or may be effected at the nucleotide level e.g. by making a nucleic acid encoding the mutated sequence, which nucleic acid may be subsequently translated to produce the mutated polypeptide. Where no amino acid is specified as the replacement amino acid for a given mutation site, suitably a randomisation of said site is used. As a default mutation, alanine (A) may be used. Suitably the mutations used at particular site(s) are as set out herein.

A fragment is suitably at least 10 amino acids in length, suitably at least 25 amino acids, suitably at least 50 amino acids, suitably at least 100 amino acids, suitably at least 200 amino acids, suitably at least 250 amino acids, suitably at least 300 amino acids, suitably at least 313 amino acids, or suitably the majority of the polypeptide of interest.

The methods of the invention may be practiced in vivo or in vitro.

In one embodiment, suitably the methods of the invention are not applied to the human or animal body. Suitably the methods of the invention are in vitro methods. Suitably the methods do not require the presence of the human or animal body. Suitably the methods are not methods of diagnosis or of surgery or of therapy of the human or animal body.

The term 'comprises' (comprise, comprising) should be understood to have its normal meaning in the art, i.e. that the stated feature or group of features is included, but that the term does not exclude any other stated feature or group of features from also being present.

ADVANTAGES

Cyclopropene is a less carbon rich group than known protein labelling groups.

Cyclopropene amino acid of the current invention leads to more rapid protein labelling than prior art techniques.

Using the cyclopropene amino acid of the present invention leads to a more efficient incorporation than prior art labelled amino acids.

It has been known to incorporate amino acids bearing norbornene groups into proteins. The present invention offers specific advantages over prior art methods involving norbornene groups. For example, although the conjugation chemistry for cyclopropene amino acids of the invention is similar to that of norbornene containing amino acids, conjugation to cyclopropene amino acids can be faster.

Incorporation of cyclopropene amino acids according to the invention can be more efficient than incorporation of prior art unnatural amino acids. The incorporation of cyclopropene amino acids according to the invention can lead to a higher level of incorporation than prior art unnatural amino acids.

It is an advantage of the invention that the cyclopropene amino acids taught can be incorporated using wild type tRNA synthetases. Prior art unnatural amino acids have tended to require mutant tRNA synthetases for their incorporation, such as, for example, amino acids incorporating BCN groups.

Rapid conjugation reactions for unnatural amino acids incorporated into polypeptides have been mentioned in the prior art. For example, TCO/BCN amino acids offer rapid reaction times, which can be faster than norbornene reaction times. However, it is an advantage of the cyclopropene amino acids that very rapid reaction times are provided.

Certain known unnatural amino acids are able to use the wild type tRNA synthetases. For example, amino acids comprising norbornene groups can be incorporated using wild type tRNA synthetase. However, by using cyclopropene containing amino acids of the invention a higher level of incorporation is achieved. In other words, the amount of material produced which comprises the unnatural amino acid is greater when using cyclopropene containing amino acids of the invention than when using prior art unnatural amino acids such as those comprising norbornene.

It is an advantage of the invention that the cyclopropene amino acids form excellent substrates for the tRNA synthetases noted herein, most suitably the wild type tRNA synthetases noted herein.

It is an advantage of the invention that the cyclopropene containing amino acids support excellent linker chemistry, for example rapid and specific reaction with tetrazine containing compounds.

It is an advantage of the invention that the cyclopropene containing amino acids are smaller in size than known unnatural amino acids previously used to label proteins. For example, a known unnatural amino acid comprising norbornene can be incorporated into polypeptides, but cyclopropene containing amino acids of the invention are advantageously of smaller size than the norbornene containing amino acids of the prior art.

It is an advantage of the invention that the cyclopropene amino acids are less likely to perturb protein structure when incorporated into polypeptides. At least part of this advantageous effect may be attributed to the small size of the cyclopropene molecular group.

A key advantage of incorporation of a cyclopropene group is that it permits a range of extremely useful further compounds such as labels to be easily and specifically attached to the cyclopropene group.

In another aspect, the invention relates to a polypeptide as described above wherein said cyclopropene group is joined to a tetrazine group.

Cyclopropene-Carbamate Linkage

An unnatural amino acid comprising an amide bonded cyclopropene has been described in the prior art (Yu et al 2012). This amino acid is 3,3 disubstituted. This amino acid is as follows:

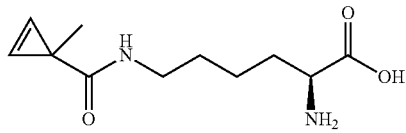 [SMILES: CC1(C(=O)NCCCC[C@H](N)C(=O)O)C=C1]

In order to incorporate this amino acid into polypeptides, it is essential to use a mutant tRNA synthetase.

In contrast, the amino acid comprising cyclopropene of the present invention contains a carbamate group (rather than an amide group). The cyclopropene containing amino acid of the present invention is therefore chemically distinct from the amide bonded cyclopropene amino acid in the art.

An exemplary amino acid of the invention is 1,3 disubstituted. An exemplary amino acid of the invention is as follows:

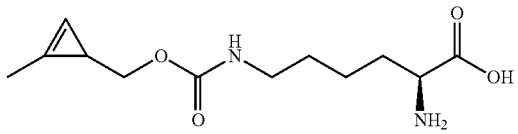 [SMILES: CC1=CC1COC(=O)NCCCC[C@H](N)C(=O)O]

It is an advantage of the carbamate-cyclopropene amino acid of the invention that it is incorporated well by the wild type tRNA synthetase. This has the advantage of requiring less biological manipulation in order to obtain good incorporation. This also provides the advantage of enhanced or increased incorporation. In other words, the cyclopropene-carbamate amino acid of the present invention is incorporated to higher levels and/or more efficiently than known unnatural amino acids.

Use of the cyclopropene amino acid of the invention may provide a superior rate of reaction with tetrazine compounds.

The carbamate chemistry of the invention provides the advantage of more degrees of freedom in the chemical structure of the incorporated amino acid. In particular, the carbamate cyclopropene of the invention has more degrees of freedom compared to the amide cyclopropene known in the art. Similarly, the carbamate cyclopropene of the invention is more accessible when present in the polypeptide chain.

By comparison with the amide bonded cyclopropene known in the art, the carbamate cyclopropene of the present invention is a slightly "longer" amino acid. This provides the advantage of a greater "reach" for the groups of the amino acid protruding away from the amino acid backbone. Again, this can render those groups more accessible for further labelling or conjugation reactions.

The chemical structure of the carbamate cyclopropene of the invention advantageously provides more conformational degrees of freedom. In other words, the carbamate cyclopropene group of the invention can adopt more conformations within a protein structure than prior art amide bonded cyclopropene amino acids.

In more detail, this may arise from the nature of the bonding between cyclopropene group and amino acid group. In the prior art amide arrangement, the important bond is SP2 hybridised. In the invention, the important bond is SP3 hybridised, which is a more flexible bonding arrangement.

Moreover, the cyclopropene carbamate arrangement of the invention comprises a methylene group between the carbamate and the cyclopropene group. Firstly, this provides a longer molecule. The prior art amide bonded version is a less advantageous shorter molecule. More specifically, the methylene carbon in the amino acid of the present invention corresponds to a double bonded oxygen group (=o) instead of the advantageous methylene carbon of the present invention. The double bonded version in the prior art amide amino acid cannot rotate as freely as the methylene carbon bonded group in the amino acid of the invention.

The fact that the amino acid of the present invention is smaller than prior art norbornene containing amino acids and yet still preserves the advantageous carbamate chemistry is a benefit of the invention. This benefit provides, among other things, better incorporation of the amino acid into the polypeptide chain.

In addition, the joining to tetrazine compounds (tetrazine conjugation) is advantageously facilitated by the carbamate cyclopropene arrangement in the amino acid of the present invention.

Suitably said tetrazine group is further joined to a fluorophore.

Suitably said tetrazine group is further joined to a polyethylene glycol (PEG) group.

Suitably said fluorophore comprises fluorescein, tetramethyl rhodamine (TAMRA) or boron-dipyrromethene (BODIPY).

Incorporation

Suitably the cyclopropene amino acid of the invention is incorporated into a polypeptide using the wild type tRNA synthetase.

Suitably the amino acid having a cyclopropene group is incorporated at a position corresponding to a lysine residue in the wild type polypeptide. This has the advantage of maintaining the closest possible structural relationship of the cyclopropene containing polypeptide to the wild type polypeptide from which it is derived.

Suitably the polypeptide comprises a single cyclopropene group. This has the advantage of maintaining specificity for any further chemical modifications which might be directed at the cyclopropene group. For example when there is only a single cyclopropene group in the polypeptide of interest then possible issues of partial modification (e.g. where only a subset of cyclopropene groups in the polypeptide are subsequently modified), or issues of reaction microenvironments varying between alternate cyclopropene groups in the same polypeptides (which could lead to unequal reactivity between different cyclopropene group(s) at different locations in the polypeptide) are advantageously avoided.

Suitably the polypeptide comprises two cyclopropene groups; suitably the polypeptide comprises three cyclopropene groups; suitably the polypeptide comprises four cyclopropene groups; suitably the polypeptide comprises five cyclopropene groups; suitably the polypeptide comprises ten cyclopropene groups or even more.

In principle multiple cyclopropene containing amino acids could be incorporated by the same or by different orthogonal codons/orthogonal tRNA pairs. Suitably multiple cyclopropene containing amino acids are incorporated by insertion of multiple amber codons (together with a suitable orthogonal tRNA synthetase as described herein).

Suitably the amino acid comprising cyclopropene is a lysine amino acid. In one embodiment, the tRNA may be from one species such as *Methanosarcina barkeri*, and the tRNA synthetase may be from another species such as *Methanosarcina mazei*. In another embodiment, tRNA may be from a first species such as *Methanosarcina mazei* and the tRNA synthetase may from a second species such as *Methanosarcina barkeri*. When an orthogonal pair comprises tRNA and tRNA synthetase from different species, it is always with the proviso that the orthogonal pair work effectively together ie. that the tRNA synthetase will effectively amino acylate the tRNA of the amino acid of interest. Equally, mutant tRNAs or mutant tRNA synthetases may be used provided they have the correct amino acylation activity. Although it is an advantage of the invention that the cyclopropene containing amino acids of the invention are effectively charged onto tRNAs using the wild type PylRS synthetase, it is equally possible to use mutant PylRS synthetases provided they are effective in charging the tRNA with the cyclopropene containing amino acid of the invention. Most suitably, orthogonal pairs comprise the tRNA and a tRNA synthetase from the same species.

Of course it is possible to evolve the wild type synthetase (or another variant of a suitable synthetase) to make a synthetase for incorporation of the cyclopropene amino acid of the invention which may have increased efficiency. In principle, a Pyl derived tRNA synthetase might be of use. Chimeric tRNA synthetases may be produced provided that the charging/acetylation part of the tRNA synthetase molecule is based on or derived from Pyl tRNA synthetase. In other words, the anti-codon part of the tRNA molecule may be varied according to operator choice, for example to direct tRNA in recognising an alternate codon such as a sense codon, a quadruplet codon, an amber codon or another "stop" codon. However, the functional acylation/charging part of the tRNA molecule should be conserved in order to preserve the cyclopropene charging activity.

Either of the *Methanosarcina barkeri* and *Methanosarcina mazei* species pyrrolysine tRNA synthetases are suitable.

Both the *Methanosarcina barkeri* and *Methanosarcina mazei* tRNAs are suitable. In any case these tRNAs differ by only one nucleotide. This one nucleotide difference has no impact on their activity in connection with cyclopropene containing amino acids. Therefore, either tRNA is equally applicable in the present invention.

The tRNA used may be varied such as mutated. In all cases, any such variants or mutants of the Pyl tRNA should always retain the capacity to interact productively with the tRNA synthetase used to charge the tRNA with the cyclopropene containing amino acid.

Genetic Incorporation and Polypeptide Production

In the method according to the invention, said genetic incorporation preferably uses an orthogonal or expanded genetic code, in which one or more specific orthogonal codons have been allocated to encode the specific amino acid residue with the cyclopropene group so that it can be genetically incorporated by using an orthogonal tRNA synthetase/tRNA pair. The orthogonal tRNA synthetase/tRNA pair can in principle be any such pair capable of charging the tRNA with the amino acid comprising the cyclopropene group and capable of incorporating that amino acid comprising the cyclopropene group into the polypeptide chain in response to the orthogonal codon. The orthogonal codon may be the orthogonal codon amber, ochre, opal or a quadruplet codon. The codon simply has to correspond to the orthogonal tRNA which will be used to carry the amino acid comprising the cyclopropene group. Preferably the orthogonal codon is amber.

It should be noted that many of the specific examples shown herein have used the amber codon and the corresponding tRNA/tRNA synthetase. As noted above, these may be varied. Alternatively, in order to use other codons without going to the trouble of using or selecting alternative tRNA/tRNA synthetase pairs capable of working with the amino acid comprising the cyclopropene group, the anticodon region of the tRNA may simply be swapped for the desired anticodon region for the codon of choice. The anticodon region is not involved in the charging or incorporation functions of the tRNA nor recognition by the tRNA synthetase so such swaps are entirely within the ambit of the skilled operator. Thus in some embodiments the anticodon region of the tRNA used in the invention such as $MbtRNA_{CUA}$ or $MmtRNA_{CUA}$ may be exchanged i.e. a chimeric $tRNAc_{CUA}$ may be used such that the anticodon region is swapped to recognise an alternate codon so that the cyclopropene containing amino acid may be incorporated in response to a different orthogonal codon as discussed herein including ochre, opal or a quadruplet codon, and the nucleic acid encoding the polypeptide into which the cyclopropene amino acid is to be incorporated is correspondingly mutated to introduce the cognate codon at the point of incorporation of the cyclopropene amino acid. Most suitably the orthogonal codon is amber.

Thus alternative orthogonal tRNA synthetase/tRNA pairs may be used if desired.

Preferably the orthogonal synthetase/tRNA pair are *Methanosarcina barkeri* MS pyrrolysine tRNA synthetase (MbPylRS) and its cognate amber suppressor tRNA (Mb-$tRNA_{CUA}$).

The *Methanosarcina barkeri* PylT gene encodes the $MbtRNA_{CUA}$ tRNA.

The *Methanosarcina barkeri* PylS gene encodes the MbPylRS tRNA synthetase protein. When particular amino acid residues are referred to using numeric addresses, the numbering is taken using MbPylRS (*Methanosarcina barkeri* pyrrolysyl-tRNA synthetase) amino acid sequence as the reference sequence (i.e. as encoded by the publicly available wild type *Methanosarcina barkeri* PylS gene Accession number Q46E77):

```
SEQ ID NO 1:
MDKKPLDVLI SATGLWMSRT GTLHKIKHYE VSRSKIYIEM

ACGDHLVVNN SRSCRTARAF RHHKYRKTCK RCRVSDEDIN

NFLTRSTEGK TSVKVKVVSA PKVKKAMPKS VSRAPKPLEN

PVSAKASTDT SRSVPSPAKS TPNSPVPTSA PAPSLTRSQL

DRVEALLSPE DKISLNIAKP FRELESELVT RRKNDFQRLY

TNDREDYLGK LERDITKFFV DRDFLEIKSP ILIPAEYVER

MGINNDTELS KQIFRVDKNL CLRPMLAPTL YNYLRKLDRI

LPDPIKIFEV GPCYRKESDG KEHLEEFTMV NFCQMGSGCT

RENLESLIKE FLDYLEIDFE IVGDSCMVYG DTLDIMHGDL

ELSSAVVGPV PLDREWGIDK PWIGAGFGLE RLLKVMHGFK

NIKRASRSES YYNGISTNL.
```

If required, the person skilled in the art may adapt MbPylRS tRNA synthetase protein by mutating it so as to optimise for the cyclopropene amino acid to be used. The need for mutation (if any) depends on the cyclopropene amino acid used. An example where the MbPylRS tRNA synthetase may need to be mutated is when the cyclopropene amino acid is not processed by the MbPylRS tRNA synthetase protein.

Such mutation (if desired) may be carried out by introducing mutations into the MbPylRS tRNA synthetase, for example at one or more of the following positions in the MbPylRS tRNA synthetase: M241, A267, Y271, L274 and C313.

tRNA Synthetases

The tRNA synthetase of the invention may be varied. Although specific tRNA synthetase sequences may have been used in the examples, the invention is not intended to be confined only to those examples.

In principle any tRNA synthetase which provides the same tRNA charging (aminoacylation) function can be employed in the invention.

For example the tRNA synthetase may be from any suitable species such as from archea, for example from *Methanosarcina barkeri* MS; *Methanosarcina barkeri* str. Fusaro; *Methanosarcina mazei* G01; *Methanosarcina acetivorans* C2A; *Methanosarcina thermophila*; or *Methanococcoides burtonii*. Alternatively the the tRNA synthetase may be from bacteria, for example from *Desulfitobacterium hafniense* DCB-2; *Desulfitobacterium hafniense* Y51; *Desulfitobacterium hafniense* PCP1; *Desulfotomaculum acetoxidans* DSM 771.

Exemplary sequences from these organisms are the publically available sequences. The following examples are provided as exemplary sequences for pyrrolysine tRNA synthetases:

```
SEQ ID NO 2:
>M.barkeriMS/1-419/Methanosarcina barkeri MS
VERSION Q6WRH6.1 GI:74501411
MDKKPLDVLISATGLWMSRTGTLHKIKHHEVSRSKIYIEMACGDHLVVNN

SRSCRTARAFRHHKYRKTCKRCRVSDEDINNFLTRSTESKNSVKVRVVSA

PKVKKAMPKSVSRAPKPLENSVSAKASTNTSRSVPSPAKSTPNSSVPASA

PAPSLTRSQLDRVEALLSPEDKISLNMAKPFRELEPELVTRRKNDFQRLY
```

TNDREDYLGKLERDITKFFVDRGFLEIKSPILIPAEYVERMGINNDTELS

KQIFRVDKNLCLRPMLAPTLYNYLRKLDRILPGPIKIFEVGPCYRKESDG

KEHLEEFTMVNFCQMGSGCTRENLEALIKEFLDYLEIDFEIVGDSCMVYG

DTLDIMHGDLELSSAVVGPVSLDREWGIDKPWIGAGFGLERLLKVMHGFK

NIKRASRSESYYNGISTNL

SEQ ID NO 3:
>M.barkeriF/1-419/Methanosarcina barkeri
str. Fusaro
VERSION YP_304395.1 GI:73668380
MDKKPLDVLISATGLWMSRTGTLHKIKHYEVSRSKIYIEMACGDHLVVNN

SRSCRTARAFRHHKYRKTCKRCRVSDEDINNFLTRSTEGKTSVKVKVVSA

PKVKKAMPKSVSRAPKPLENPVSAKASTDTSRSVPSPAKSTPNSPVPTSA

PAPSLTRSQLDRVEALLSPEDKISLNIAKPFRELESELVTRRKNDFQRLY

TNDREDYLGKLERDITKFFVDRDFLEIKSPILIPAEYVERMGINNDTELS

KQIFRVDKNLCLRPMLAPTLYNYLRKLDRILPDPIKIFEVGPCYRKESDG

KEHLEEFTMVNFCQMGSGCTRENLESLIKEFLDYLEIDFEIVGDSCMVYG

DTLDIMHGDLELSSAVVGPVPLDREWGIDKPWIGAGFGLERLLKVMHGFK

NIKRASRSESYYNGISTNL

SEQ ID NO 4:
>M.mazei/1-454
Methanosarcina mazei Go1
VERSION NP_633469.1 GI:21227547
MDKKPLNTLISATGLWMSRTGTIHKIKHHEVSRSKIYIEMACGDHLVVNN

SRSSRTARALRHHKYRKTCKRCRVSDEDLNKFLTKANEDQTSVKVKVVSA

PTRTKKAMPKSVARAPKPLENTEAAQAQPSGSKFSPAIPVSTQESVSVPA

SVSTSISSISTGATASALVKGNTNPITSMSAPVQASAPALTKSQTDRLEV

LLNPKDEISLNSGKPFRELESELLSRRKKDLQQIYAEERENYLGKLEREI

TRFFVDRGFLEIKSPILIPLEYIERMGIDNDTELSKQIFRVDKNFCLRPM

LAPNLYNYLRKLDRALPDPIKIFEIGPCYRKESDGKEHLEEFTMLNFCQM

GSGCTRENLESIITDFLNHLGIDFKIVGDSCMVYGDTLDVMHGDLELSSA

VVGPIPLDREWGIDKPWIGAGFGLERLLKVHDFKNIKRAARSESYYNGI

STNL

SEQ ID NO 5:
>M.acetivorans A-443
Methanosarcina acetivorans C2A
VERSION NP_615128.2 GI:161484944
MDKKPLDTLISATGLWMSRTGMIHKIKHHEVSRSKIYIEMACGERLVVNN

SRSSRTARALRHHKYRKTCRHCRVSDEDINNFLTKTSEEKTTVKVKVVSA

PRVRKAMPKSVARAPKPLEATAQVPLSGSKPAPATPVSAPAQAPAPSTGS

ASATSASAQRMANSAAAPAAPVPTSAPALTKGQLDRLEGLLSPKDEISLD

SEKPFRELESELLSRRKKDLKRIYAEERENYLGKLEREITKFFVDRGFLE

IKSPILIPAEYVERMGINSDTELSKQVFRIDKNFCLRPMLAPNLYNYLRK

LDRALPDPIKIFEIGPCYRKESDGKEHLEEFTMLNFCQMGSGCTRENLEA

IITEFLNHLGIDFEIIGDSCMVYGNTLDVMHDDLELSSAVVGPVPLDREW

GIDKPWIGAGFGLERLLKVMHGFKNIKRAARSESYYNGISTNL

SEQ ID NO 6:
>M.thermophila/1-478
Methanosarcina thermophila, VERSION
DQ017250.1 GI:67773308
MDKKPLNTLISATGLWMSRTGKLHKIRHHEVSKRKIYIEMECGERLVVNN

SRSCRAARALRHHKYRKICKHCRVSDEDLNKFLTRTNEDKSNAKVTVVSA

PKIRKVMPKSVARTPKPLENTAPVQTLPSESQPAPTTPISASTTAPASTS

TTAPAPASTTAPAPASTTAPASASTTISTSAMPASTSAQGTTKFNYISGG

FPRPIPVQASAPALTKSQIDRLQGLLSPKDEISLDSGTPFRKLESELLSR

RRKDLKQIYAEEREHYLGKLEREITKFFVDRGFLEIKSPILIPMEYIERM

GIDNDKELSKQIFRVDNNFCLRPMLAPNLYNYLRKLNRALPDPIKIFEIG

PCYRKESDGKEHLEEFTMLNFCQMGSGCTRENLEAIIKDFLDYLGIDFEI

VGDSCMVYGDTLDVMHGDLELSSAVVGPVPMDRDWGINKPWIGAGFGLER

LLKVMHNFKNIKRASRSESYYNGISTNL

SEQ ID NO 7:
>M.burtonii/1-416
Methanococcoides burtonii DSM 6242, VERSION
YP_566710.1 GI:91774018
MEKQLLDVLVELNGVWLSRSGLLHGIRNFEITTKHIHIETDCGARFIVRN

SRSSRSARSLRHNKYRKPCKRCRPADEQIDRFVKKTFKEKRQTVSVFSSP

KKHVPKKPKVAVIKSFSISTPSPKEASVSNSIPTPSISVVKDEVKVPEVK

YTPSQIERLKTLMSPDDKIPIQDELPEFKVLEKELIQRRRDDLKKMYEED

REDRLGKLERDITEFFVDRGFLEIKSPIMIPFEYIERMGIDKDDHLNKQI

FRVDESMCLRPMLAPCLYNYLRKLDKVLPDPIRIFEIGPCYRKESDGSSH

LEEFTMVNFCQMGSGCTRENMEALIDEFLEHLGIEYEIADNCMVYGDTI

DIMHGDLELSSAVVGPIPLDREWGVNKPWMGAGFGLERLLKVRHNYTNIR

RASRSELYYNGINTNL

SEQ ID NO 8:
>D.hafniense_DCB-2/1-279
Desulfitobacterium hafniense DCB-2
VERSION YP_002461289.1 GI:219670854
MSSFWTKVQYQRLKELNASGEQLEMGFSDALSRDRAFQGIEHQLMSQGKR

HLEQLRTVKHRPALLELEEGLAKALHQQGFVQVVTPTIITKSALAKMTIG

EDHPLFSQVFWLDGKKCLRPMLAPNLYTLWRELERLWDKPIRIFEIGTCY

RKESQGAQHLNEFTMLNLTELGTPLEERHQRLEDMARWVLEAAGIREFEL

VTESSVVYGDTVDVMKGDLELASGAMGPHFLDEKWEIVDPWVGLGFGLER

LLMIREGTQHVQSMARSLSYLDGVRLNIN

SEQ ID NO 9:
>D.hafniense_Y51/1-312
Desulfitobacterium hafniense Y51
VERSION YP_521192.1 GI:89897705
MDRIDHTDSKFVQAGETPVLPATFMFLTRRDPPLSSFWTKVQYQRLKELN

ASGEQLEMGFSDALSRDRAFQGIEHQLMSQGKRHLEQLRTVKHRPALLEL

EEGLAKALHQQGFVQVVTPTIITKSALAKMTIGEDHPLFSQVFWLDGKKC

LRPMLAPNLYTLWRELERLWDKPIRIFEIGTCYRKESQGAQHLNEFTMLN

LTELGTPLEERHQRLEDMARWVLEAAGIREFELVTESSVVYGDTVDVMKG

DLELASGAMGPHFLDEKWEIVDPWVGLGFGLERLLMIREGTQHVQSMARS

LSYLDGVRLNIN

-continued

```
SEQ ID NO 10:
>D.hafniensePCP1/1-288
Desulfitobacterium hafniense
VERSION AY692340.1 GI:53771772
MFLTRRDPPLSSFWTKVQYQRLKELNASGEQLEMGFSDALSRDRAFQGIE

HQLMSQGKRHLEQLRTVKHRPALLELEEKLAKALHQQGFVQVVTPTIITK

SALAKMTIGEDHPLFSQVFWLDGKKCLRPMLAPNLYTLWRELERLWDKPI

RIFEIGTCYRKESQGAQHLNEFTMLNLTELGTPLEERHQRLEDMARWVLE

AAGIREFELVTESSVVYGDTVDVMKGDLELASGAMGPHELDEKWEIFDPW

VGLGFGLERLLMIREGTQHVQSMARSLSYLDGVRLNIN

SEQ ID NO 11:
>D.acetoxidans/1-277
Desulfotomaculum acetoxidans DSM 771
VERSION YP_003189614.1 GI:258513392
MSFLWTVSQQKRLSELNASEEEKNMSFSSTSDREAAYKRVEMRLINESKQ

RLNKLRHETRPAICALENRLAAALRGAGFVQVATPVILSKKLLGKMTITD

EHALFSQVFWIEENKCLRPMLAPNLYYILKDLLRLWEKPVRIFEIGSCFR

KESQGSNHLNEFTMLNLVEWGLPEEQRQKRISELAKLVMDETGIDEYHLE

HAESVVYGETVDVMHRDIELGSGALGPHFLDGRWGVVGPWVGIGFGLERL

LMVEQGGQNVRSMGKSLTYLDGVRLNI
```

When the particular tRNA charging (aminoacylation) function has been provided by mutating the tRNA synthetase, then it may not be appropriate to simply use another wild-type tRNA sequence, for example one selected from the above. In this scenario, it will be important to preserve the same tRNA charging (aminoacylation) function. This is accomplished by transferring the mutation(s) in the exemplary tRNA synthetase into an alternate tRNA synthetase backbone, such as one selected from the above.

In this way it should be possible to transfer selected mutations to corresponding tRNA synthetase sequences such as corresponding pylS sequences from other organisms beyond exemplary *M. barkeri* and/or *M. mazei* sequences.

Target tRNA synthetase proteins/backbones, may be selected by alignment to known tRNA synthetases such as exemplary *M. barkeri* and/or *M. mazei* sequences.

This subject is now illustrated by reference to the pylS (pyrrolysine tRNA synthetase) sequences but the principles apply equally to the particular tRNA synthetase of interest.

For example, an alignment of all, PylS sequences may be prepared. These can have a low overall % sequence identity. Thus it is important to study the sequence such as by aligning the sequence to known tRNA synthetases (rather than simply to use a low sequence identity score) to ensure that the sequence being used is indeed a tRNA synthetase.

Thus suitably when sequence identity is being considered, suitably it is considered across the sequences of the examples of tRNA synthetases as above. Suitably the % identity may be as defined from an alignment of the above sequences.

It may be useful to focus on the catalytic region. The aim of this is to provide a tRNA catalytic region from which a high % identity can be defined to capture/identify backbone scaffolds suitable for accepting mutations transplanted in order to produce the same tRNA charging (aminoacylation) function, for example new or unnatural amino acid recognition.

Thus suitably when sequence identity is being considered, suitably it is considered across the catalytic region. Suitably the % identity may be as defined from the catalytic region.

'Transferring' or 'transplanting' mutations onto an alternate tRNA synthetase backbone can be accomplished by site directed mutagenesis of a nucleotide sequence encoding the tRNA synthetase backbone. This technique is well known in the art. Essentially the backbone pylS sequence is selected (for example using the active site alignment discussed above) and the selected mutations are transferred to (i.e. made in) the corresponding/homologous positions.

When particular amino acid residues are referred to using numeric addresses, unless otherwise apparent, the numbering is taken using MbPylRS (*Methanosarcina barkeri* pyrrolysyl-tRNA synthetase) amino acid sequence as the reference sequence (i.e. as encoded by the publicly available wild type *Methanosarcina barkeri* PylS gene Accession number Q46E77):

```
SEQ ID NO 1:
MDKKPLDVLI SATGLWMSRT GTLHKIKHYE VSRSKIYIEM

ACGDHLVVNN SRSCRTARAF RHHKYRKTCK RCRVSDEDIN

NFLTRSTEGK TSVKVKVVSA PKVKKAMPKS VSRAPKPLEN

PVSAKASTDT SRSVPSPAKS TPNSPVPTSA PAPSLTRSQL

DRVEALLSPE DKISLNIAKP FRELESELVT RRKNDFQRLY

TNDREDYLGK LERDITKFFV DRDFLEIKSP ILIPAEYVER

MGINNDTELS KQIFRVDKNL CLRPMLAPTL YNYLRKLDRI

LPDPIKIFEV GPCYRKESDG KEHLEEFTMV NFCQMGSGCT

RENLESLIKE FLDYLEIDFE IVGDSCMVYG DTLDIMHGDL

ELSSAVVGPV PLDREWGIDK PWIGAGFGLE RLLKVMHGFK

NIKRASRSES YYNGISTNL
```

This is to be used as is well understood in the art to locate the residue of interest. This is not always a strict counting exercise—attention must be paid to the context or alignment. For example, if the protein of interest is of a slightly different length, then location of the correct residue in that sequence corresponding to (for example) L266 may require the sequences to be aligned and the equivalent or corresponding residue picked, rather than simply taking the 266th residue of the sequence of interest. This is well within the ambit of the skilled reader.

Notation for mutations used herein is the standard in the art. For example L266M means that the amino acid corresponding to L at position 266 of the wild type sequence is replaced with M.

The transplantation of mutations between alternate tRNA backbones is now illustrated with reference to exemplary *M. barkeri* and *M. mazei* sequences, but the same principles apply equally to transplantation onto or from other backbones.

For example Mb AcKRS is an engineered synthetase for the incorporation of AcK Parental protein/backbone: *M. barkeri* PylS Mutations: L266V, L270I, Y271F, L274A, C317F Mb PCKRS: engineered synthetase for the incorporation of PCK Parental protein/backbone: *M. barkeri* PylS Mutations: M241F, A267S, Y271C, L274M Synthetases with the same substrate specificities can be obtained by transplanting these mutations into *M. mazei* PylS. Thus the following synthetases may be generated by transplantation of the mutations from the Mb backbone onto the Mm tRNA backbone: Mm AcKRS introducing mutations L301V, L305I, Y306F, L309A, C348F into *M. mazei* PylS, and Mm PCKRS introducing mutations M276F, A302S, Y306C, L309M into *M. mazei* PylS.

Full length sequences of these exemplary transplanted mutation synthetases are given below.

SEQ ID NO 12:
>Mb_PylS/1-419
MDKKPLDVLISATGLWMSRTGTLHKIKHHEVSRSKIYIEMACGDHLVVNN

SRSCRTARAFRHHKYRKTCKRCRVSDEDINNFLTRSTESKNSVKVRVVSA

PKVKKAMPKSVSRAPKPLENSVSAKASTNTSRSVPSPAKSTPNSSVPASA

PAPSLTRSQLDRVEALLSPEDKISLNMAKPFRELEPELVTRRKNDFQRLY

TNDREDYLGKLERDITKFFVDRGFLEIKSPILIPAEYVERMGINNDTELS

KQIFRVDKNLCLRPMLAPTLYNYLRKLDRILPGPIKIFEVGPCYRKESDG

KEHLEEFTMVNFCQMGSGCTRENLEALIKEFLDYLEIDFEIVGDSCMVYG

DTLDIMHGDLELSSAVVGPVSLDREWGIDKPWIGAGFGLERLLKVMHGFK

NIKRASRSESYYNGISTNL

SEQ ID NO 13:
>Mb_AcKRS/1-419
MDKKPLDVLISATGLWMSRTGTLHKIKHHEVSRSKIYIEMACGDHLVVNN

SRSCRTARAFRHHKYRKTCKRCRVSGEDINNFLTRSTESKNSVKVRVVSA

PKVKKAMPKSVSRAPKPLENSVSAKASTNTSRSVPSPAKSTPNSSVPASA

PAPSLTRSQLDRVEALLSPEDKISLNMAKPFRELEPELVTRRKNDFQRLY

TNDREDYLGKLERDITKFFVDRGFLEIKSPILIPAEYVERMGINNDTELS

KQIFRVDKNLCLRPMVAPTIFNYARKLDRILPGPIKIFEVGPCYRKESDG

KEHLEEFTMVNFFQMGSGCTRENLEALIKEFLDYLEIDFEIVGDSCMVYG

DTLDIMHGDLELSSAVVGPVSLDREWGIDKPWIGAGFGLERLLKVMHGFK

NIKRASRSESYYNGISTNL

SEQ ID NO 14:
>Mb_PCKRS/1-419
MDKKPLDVLISATGLWMSRTGTLHKIKHHEVSRSKIYIEMACGDHLVVNN

SRSCRTARAFRHHKYRKTCKRCRVSDEDINNFLTRSTESKNSVKVRVVSA

PKVKKAMPKSVSRAPKPLENSVSAKASTNTSRSVPSPAKSTPNSSVPASA

PAPSLTRSQLDRVEALLSPEDKISLNMAKPFRELEPELVTRRKNDFQRLY

TNDREDYLGKLERDITKFFVDRGFLEIKSPILIPAEYVERFGINNDTELS

KQIFRVDKNLCLRPMLSPTLCNYMRKLDRILPGPIKIFEVGPCYRKESDG

KEHLEEFTMVNFCQMGSGCTRENLEALIKEFLDYLEIDFEIVGDSCMVYG

DTLDIMHGDLELSSAVVGPVSLDREWGIDKPWIGAGFGLERLLKVMHGFK

NIKRASRSESYYNGISTNL

SEQ ID NO 15:
>Mm_PylS/1-454
MDKKPLNTLISATGLWMSRTGTIHKIKHHEVSRSKIYIEMACGDHLVVNN

SRSSRTARALRHHKYRKTCKRCRVSDEDLNKFLTKANEDQTSVKVKVVSA

PTRTKKAMPKSVARAPKPLENTEAAQAQPSGSKFSPAIPVSTQESVSVPA

SVSTSISSISTGATASALVKGNTNPITSMSAPVQASAPALTKSQTDRLEV

LLNPKDEISLNSGKPFRELESELLSRRKKDLQQIYAEERENYLGKLEREI

TRFFVDRGFLEIKSPILIPLEYIERMGIDNDTELSKQIFRVDKNFCLRPM

LAPNLYNYLRKLDRALPDPIKIFEIGPCYRKESDGKEHLEEFTMLNFCQM

GSGCTRENLESIITDFLNHLGIDFKIVGDSCMVYGDTLDVMHGDLELSSA

VVGPIPLDREWGIDKPWIGAGFGLERLLKVKHDFKNIKRAARSESYYNGI

STNL

SEQ ID NO 16:
>Mm_AcKRS/1-454
MDKKPLNTLISATGLWMSRTGTIHKIKHHEVSRSKIYIEMACGDHLVVNN

SRSSRTARALRHHKYRKTCKRCRVSDEDLNKFLTKANEDQTSVKVKVVSA

PTRTKKAMPKSVARAPKPLENTEAAQAQPSGSKFSPAIPVSTQESVSVPA

SVSTSISSISTGATASALVKGNTNPITSMSAPVQASAPALTKSQTDRLEV

LLNPKDEISLNSGKPFRELESELLSRRKKDLQQIYAEERENYLGKLEREI

TRFFVDRGFLEIKSPILIPLEYIERMGIDNDTELSKQIFRVDKNFCLRPM

VAPNIFNYARKLDRALPDPIKIFEIGPCYRKESDGKEHLEEFTMLNFFQM

GSGCTRENLESIITDFLNHLGIDFKIVGDSCMVYGDTLDVMHGDLELSSA

VVGPIPLDREWGIDKPWIGAGFGLERLLKVKHDFKNIKRAARSESYYNGI

STNL

SEQ ID NO 17:
>Mm_PCKRS/1-454
MDKKPLNTLISATGLWMSRTGTIHKIKHHEVSRSKIYIEMACGDHLVVNN

SRSSRTARALRHHKYRKTCKRCRVSDEDLNKFLTKANEDQTSVKVKVVSA

PTRTKKAMPKSVARAPKPLENTEAAQAQPSGSKFSPAIPVSTQESVSVPA

SVSTSISSISTGATASALVKGNTNPITSMSAPVQASAPALTKSQTDRLEV

LLNPKDEISLNSGKPFRELESELLSRRKKDLQQIYAEERENYLGKLEREI

TRFFVDRGFLEIKSPILIPLEYIERFGIDNDTELSKQIFRVDKNFCLRPM

LSPNLCNYMRKLDRALPDPIKIFEIGPCYRKESDGKEHLEEFTMLNFCQM

GSGCTRENLESIITDFLNHLGIDFKIVGDSCMVYGDTLDVMHGDLELSSA

VVGPIPLDREWGIDKPWIGAGFGLERLLKVKHDFKNIKRAARSESYYNGI

STNL

The same principle applies equally to other mutations and/or to other backbones.

Transplanted polypeptides produced in this manner should advantageously be tested to ensure that the desired function/substrate specificities have been preserved.

Polynucleotides encoding the polypeptide of interest for the method described above can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Vectors of the invention may be transformed or transfected into a suitable host cell as described to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Another aspect of the invention is a method, such as an in vitro method, of incorporating the cyclopropene containing amino acid(s) genetically and site-specifically into the protein of choice, suitably in a eukaryotic cell. One advantage of incorporating genetically by said method is that it obviates the need to deliver the proteins comprising the cyclopropene amino acid into a cell once formed, since in this embodiment they may be synthesised directly in the target cell. The method comprises the following steps:
i) introducing, or replacing a specific codon with, an orthogonal codon such as an amber codon at the desired site in the nucleotide sequence encoding the protein
ii) introducing an expression system of orthogonal tRNA synthetase/tRNA pair in the cell, such as a pyrollysyl-tRNA synthetase/tRNA pair
iii) growing the cells in a medium with the cyclopropene containing amino acid according to the invention.

Step (i) entails or replacing a specific codon with an orthogonal codon such as an amber codon at the desired site in the genetic sequence of the protein. This can be achieved by simply introducing a construct, such as a plasmid, with the nucleotide sequence encoding the protein, wherein the site where the cyclopropene containing amino acid is desired to be introduced/replaced is altered to comprise an orthogonal codon such as an amber codon. This is well within the person skilled in the art's ability and examples of such are given here below.

Step (ii) requires an orthogonal expression system to specifically incorporate the cyclopropene containing amino acid at the desired location (e.g. the amber codon). Thus a specific orthogonal tRNA synthetase such as an orthogonal pyrollysyl-tRNA synthetase and a specific corresponding orthogonal tRNA pair which are together capable of charging said tRNA with the cyclopropene containing amino acid are required. Examples of these are provided herein.

Protein Expression and Purification

Host cells comprising polynucleotides of the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins of the invention can be extracted from host cells by a variety of techniques known in the art, including enzymatic, chemical and/or osmotic lysis and physical disruption.

Proteins of the invention can be purified by standard techniques known in the art such as preparative chromatography, affinity purification or any other suitable technique.

Further Advantages

Yu et al join tetrazoles to cyclopropene amino acids in polypeptides. Yu et al require the use of ultraviolet irradiation in order to photoactivate their conjugation groups. Their best reaction rates were achieved with 302 nano metres UV irradiation. However, this type of UV irradiation has high ionisation potential. This means that the molecules and/or cells upon which the radiation is directed are likely to be damaged by this UV energy. By contrast, the conjugations of the present invention do not require any UV step for photoactivation. Even when Yu et al use a less damaging source of UV irradiation (eg. 365 nano metre UV irradiation), the observed reaction rates are considerably slower than those provided by the present invention. Thus, even if the UV irradiation is adjusted in Yu et al in an attempt to try to avoid or reduce some of the drawbacks associated with UV treatment, the same laborious irradiation step must still be carried out and slower reaction rates are achieved. It is an advantage of the present invention that UV irradiation can be omitted, and that excellent reaction rates are obtained even without photoactivation.

It is an advantage of the cyclopropene amino acids of the present invention that they are easy to manufacture. For example, the number steps in the synthetic pathway is advantageously few.

It should be noted that the prior art cyclopropene amino acid of Yu et al contains an amide group. This amide bond is a potential substrate for peptidases. Peptidase action on the amide bond of the prior art cyclopropene amino acid would cleave the cyclopropene part of the molecule off the polypeptide. This is clearly a disadvantage. By contrast, it is an advantage of the carbamate linked cyclopropene groups of the present invention that carbamate bonded cyclopropene is not a target for peptidases.

Prior art based techniques rely on tetrazole chemistry for conjugation. In contrast, the present invention teaches the use of advantageous tetrazine chemistry.

It is an advantage of the carbamate bonded cyclopropene amino acids of the present invention that they enable the use of the wild type PylRS synthetase. Making use of the wild type synthetase is advantageous as it involves less labour by alleviating the need to prepare mutant synthetases. In addition, the mutant synthetases do not always amino acylate in tRNA to the same level as wild type tRNA synthetases. In other words, the mutations required to be made to a synthetase in order to handle prior art cyclopropene amide bonded amino acids can cause a loss of efficiency of amino acylation. In contrast, it is demonstrated herein that amino acylation using the wild type synthetase with the amino acid of the present invention is a very efficient process, which is a further advantage over prior art techniques.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which:

FIG. 1A: Proteome tagging via SORT (stochastic orthogonal recoding of translation) uses an orthogonal aminoacyl-tRNA synthetase/tRNA pair. The pyrrolysyl-tRNA synthetase/tRNA pair is used in this study. This synthetase (and its previously evolved active-site variants) recognizes a range of unnatural amino acids (yellow star, and yellow hexagon), does not aminoacylate endogenous tRNAs, but efficiently aminoacylates its cognate tRNA—without regard to anticodon identity; PyltRNA is not a substrate for endogenous aminoacyl-tRNA synthetases. Orthogonal pyrrolysyl-tRNA synthetase/tRNA$_{XXX}$ pairs (XXX indicates choice of anticodon, yellow) in which the anticodon has been altered compete for the decoding of sense codons (dark blue and pink) via a pathway that is orthogonal to that used by natural synthetases and tRNAs (dark blue and pink) to direct natural amino acids. SORT allows the incorporation of diverse chemical groups into the proteome, in response to diverse codons. Since there is no competition at the active site of the orthogonal synthetase, starvation and minimal media are not required. In addition the expression pattern of the orthogonal proteome tagging system can be genetically directed allowing tissue specific proteome labelling. Selective pressure incorporation approaches are shown in for comparison to SORT. FIG. 1B: The combination of encoding amino acids (1-3) across the proteome via SORT and chemoselective modification of 3 with tetrazine probes (4a-g, 5, 6 and 7) allows detection of labelled proteins via SORT-M (stochastic orthogonal recoding of translation and chemoselective modification). Amino acid structures: N$^\varepsilon$-((tert-butoxy)carbonyl)-L-lysine 1, N$^\varepsilon$-(1-propynlyoxy)carbonyl)-L-lysine 2 and N$^\varepsilon$-(((2-methylcycloprop-2-en-1-yl)methoxy)carbonyl)-L-lysine.

FIG. 2A-C Shows Quantitative Site-Specific Incorporation of 3 into Proteins Expressed in *E. coli* and its Rapid and Quantitative Labelling with Tetrazine Probes FIG. 2A: The PylRS/RNA$_{CUA}$ pair directs efficient, site-specific incorporation of 3 into sfGFP bearing an amber stop codon at position 150. Incorporation of 3 is more efficient than 1 a well-established excellent substrate for the PylRS/tRNA$_{CUA}$ pair.

FIG. 2B: Specific and quantitative labelling of 2 nmol sfGFP bearing 3 with 10 equivalents of tetrazine fluorophore 4a. ESI-MS analysis of sfGFP-3 purified from *E. coli* grown with 1 mM 3 bearing the PylRS/RNA$_{CUA}$ pair and SfGFP150TAG confirms the incorporation of 3. sfGFP150-3: Expected mass: 27951.5 Da, Found mass: 27950±1.0 Da, minor peak 27820 corresponding to loss of N-terminal methionine. Labelling sfGFP150-3 with 4a is quantitative, as judged by ESI-MS of the labelling reaction. Expected mass: 28758.4 Da, Found mass: 28758±1.0 Da, minor peak 28627 corresponds to loss of N-terminal methionine.

FIG. 2C: Determining the rate constant for labelling of sfGFP-3 (10.6 sfGFP incorporating 3 at position 150), with 10 equivalents of 4a. 2 nmol of purified sfGFP-3, (10.6 μM in 20 mM Tris-HCl, 100 mM NaCl, 2 mM EDTA, pH 7.4) were incubated with 20 nmol of tetrazine-dye conjugate 4a (10 μl of a 2 mM solution in DMSO). At different time points 8 μl, aliquots were taken from the solution and quenched with a 700-fold excess of BCN and plunged into liquid nitrogen. Samples were mixed with NuPAGE LDS sample buffer supplemented with 5% β-mercaptoethanol, heated for 10 min to 90° C. and analyzed by 4-12% SDS page. The amounts of labelled proteins were quantified by scanning the fluorescent bands with a Typhoon Trio phosphoimager (GE Life Sciences). Bands were quantified with the ImageQuant™ TL software (GE Life Sciences) using rubber band background subtraction. The rate constant was determined by fitting the data to a single-exponential equation. The calculated observed rate k' was divided by the concentration of 4a to obtain rate constant k for the reaction. Measurements were done in triplicate. All data processing was performed using Kaleidagraph software (Synergy Software, Reading, UK). For comparison the rate of labelling sfGFP bearing Nε-5-norbornene-2-yloxycarbonyl-L-lysine (NorK), a known substrate for PylRS, was determined in a similar way using 11.25 μM sfGFP bearing NorK at position 150 (SfGFP-NorK) and 20 equivalents of 4a.

FIG. 3 shows—primers (SEQ ID NOS. 18-45).

FIG. 4A: Proteome labelling with 3 via the indicated PylRS/tRNA$_{XXX}$ pair. Cells contained two plasmids, one encoding MbPylRS, the other encoding T4 lysozyme and the indicated tRNA$_{XXX}$. Cells were grown in the presence of 0.1 mM 3 from OD$_{600}$=0.2 and T4 lysozyme expression, induced by the addition of 0.2 mM arabinose after 1 h. After a further 3 h cells were harvested. Tagged proteins in the lysate were detected via an inverse electron demand Diels-Alder reaction between incorporated 3 and tetrazine fluorophore 4a (20 mM, 1 h, RT). The amino acids in parentheses are the natural amino acids encoded by the endogenous tRNA bearing the corresponding anti-codon. FIG. 4B: Lane profile analysis for each codon.

T4 lysozyme isolated after SORT with UUU(Lys) in the presence of 1 mM 3. Expected mass WT T4 lysozyme: 19512.2 Da, Found mass: 19510±2.0 Da. Expected mass WT T4 lysozyme Lys 3→single mutation: 19622.3 Da, Found mass: 19620±2.0 Da.

Figure 6:
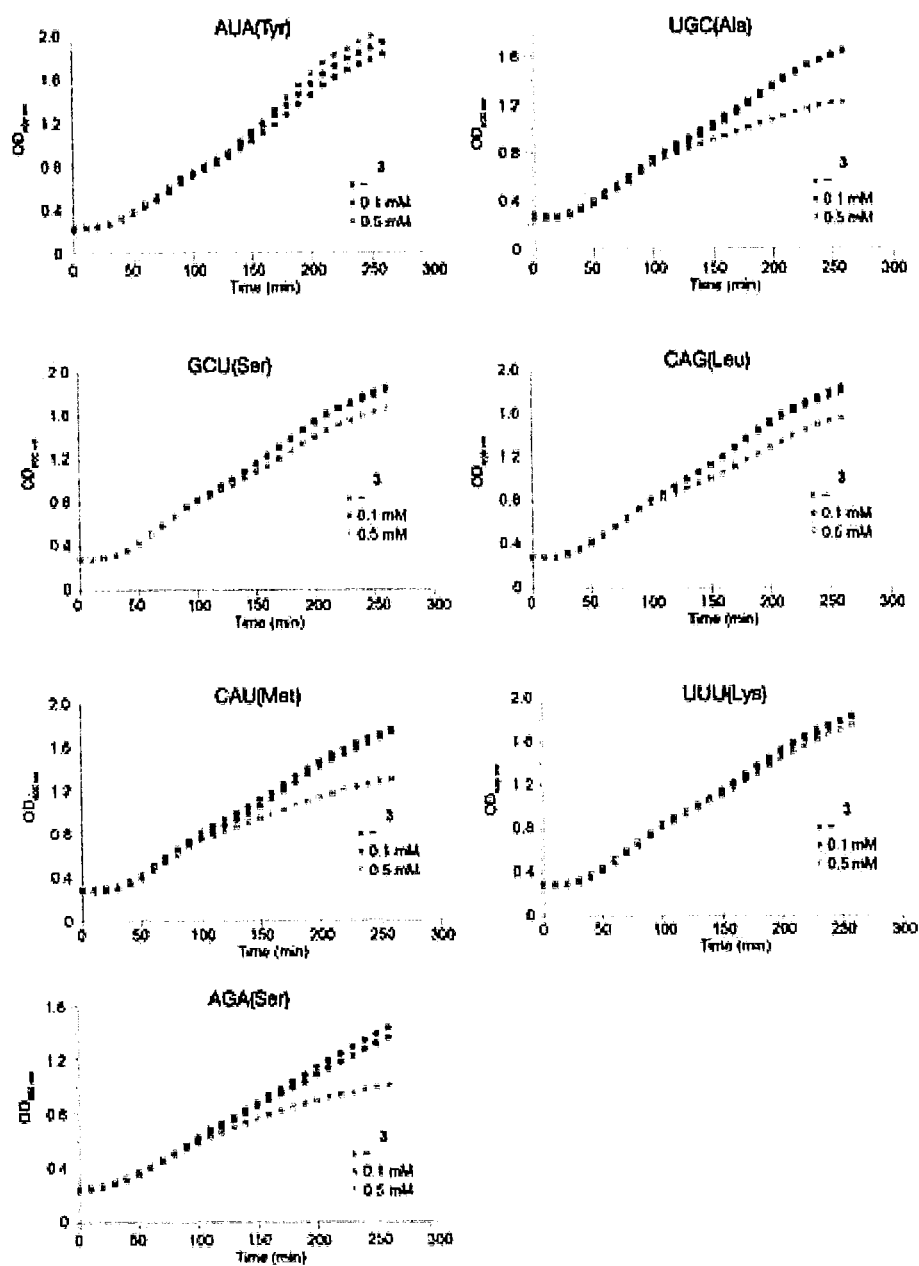

FIG. 6 Shows Incorporation of 3 (0.1 mM) via SORT-M is Not Toxic to Cells

Chemically competent DH10B cells were transformed with two plasmids: pBKwtPylRS necessary for expression of PylRS, and pBAD_wtT4L_MbPylT$_{XXX}$ plasmids that is required for expression of PyltRNA$_{XXX}$ and expresses lysozyme under arabinose control. The cells were recovered in 1 ml SOB medium for one hour at 37° C. prior to aliquoting to 10 ml LB-KT (LB media with 50 μg ml$^{-1}$ kanamycin, and 25 μg ml$^{-1}$ tetracycline) and incubated overnight (37° C., 250 rpm, 12 h). The overnight culture (OD$_{600}$≈3) was diluted to a OD$_{600}$~0.3 in 10 mL LB-KT$_{1/2}$ (LB media with 25 μg ml$^{-1}$ kanamycin, and 12.5 μg ml$^{-1}$ tetracycline) supplemented with 3 at different concentrations, 0, 0.1, 0.5 mM. 200 μL aliquots of these cultures were transferred into a 96-well plate and $OD_{600}$ measured using a Microplate reader, Infinite 200 Pro (TECAN). $OD_{600}$ was measured for each sample every 10 min with linear 1 mm shaking between the measurements.

Figure 7:
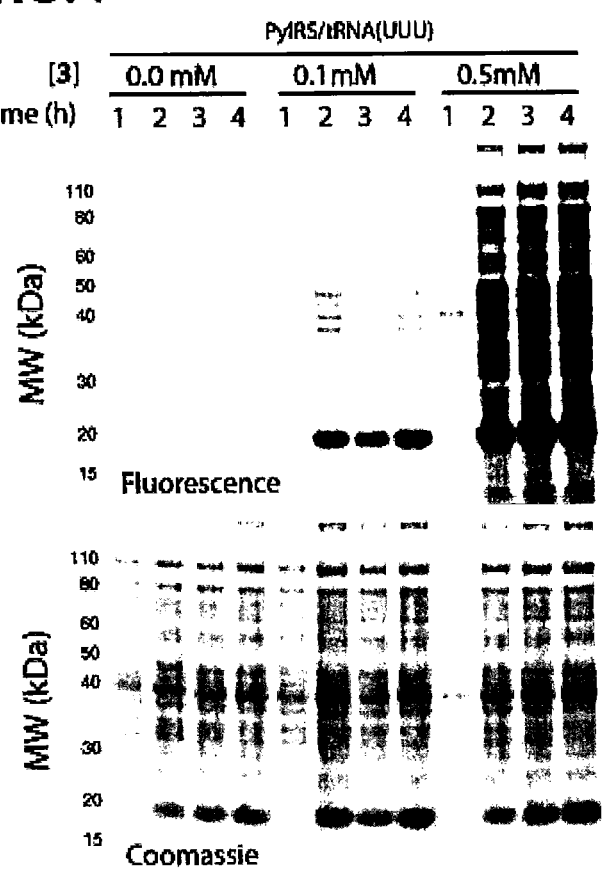

FIG. 7 Shows Measurement of Time-Dependent Variation in Incorporation of 3 in Proteome via SORT-M at Different Concentrations of 3 in Response to AAA Codon Chemically competent DH10B cells were transformed with two plasmids: pBKwtPylRS necessary for expression of PylRS, and pBAD_wtT4LMbPylT$_{UUU}$ plasmid that is required for expression of PyltRNA$_{UUU}$. pBAD_wtT4L_MbPylT$_{UUU}$ plasmid also contains the gene for expression of T4 lysozyme that is downstream of arabinose-inducible promoter. After transformation, cells were recovered in 1 ml SOB medium for one hour at 37° C. prior to inoculation in 10 ml LB-KT (LB media with 50 µg ml$^{-1}$ kanamycin, and 25 µg tetracycline). The culture was incubated overnight (37° C., 250 rpm, 12 h) and subsequently diluted to an $OD_{600}$~0.3 in 30 mL LB-KT$_{1/2}$ (LB media with 25 µg ml$^{-1}$ kanamycin, and 12.5 µg ml$^{-1}$ tetracycline) supplemented with 3 at different concentrations, 0, 0.1, 0.5 mM. The cultures was incubated (37° C., 250 rpm) for 1 h, when $OD_{600}$ reached approximately 0.6. 2 ml culture aliquot was collected in a separate tube for each of three cultures. This is the pre-induction culture (lane labelled as 1 in the gel image). Subsequently arabinose was added at a final concentration of 0.2% (v/v) to induce expression of T4 lysozyme and culture aliquots of 2 mL were collected every hour (lanes labelled as 2, 3 and 4 corresponding to 1, 2 and 3 h culture collection after induction). For each of the collected cultures, bacterial cells were pelleted by centrifugation at 4° C., washed with ice cold PBS (3×1 mL) and subsequently the pellets were frozen and stored at –20° C. The pellets were then thawed in 200 µL of ice cold PBS and lysed by sonication (9×10 s ON/20 s OFF, 70% power). The lysates were clarified by centrifugation at 15,000 RPM, 4° C. for 30 minutes. The supernatants were transferred to fresh 1.5 mL tubes. 50 µL of supernatant was transferred to a new tube for the labeling reactions, and the rest was frozen in liquid nitrogen and stored at –80 C. To the 50 µL of supernatant, 0.5 µL of 2 mM 4a was added and the lysates were incubated at 25° C. for 1 hour. After 1 h, 17 µL of 4×LDS sample buffer supplemented (6 mM BCN and 5% BME) was added and mixed by vortexing gently. Samples were incubated for 10 min before boiling at 90° C. for 10 min. Samples were analysed by 4-12% SDS-PAGE and fluorescent images were acquired using Typhoon Trio phosphoimager (GE Life Sciences)

Figure 8A:
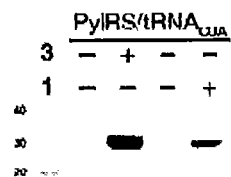
Figure 8B:
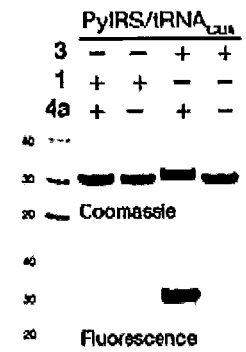
Figure 8C:
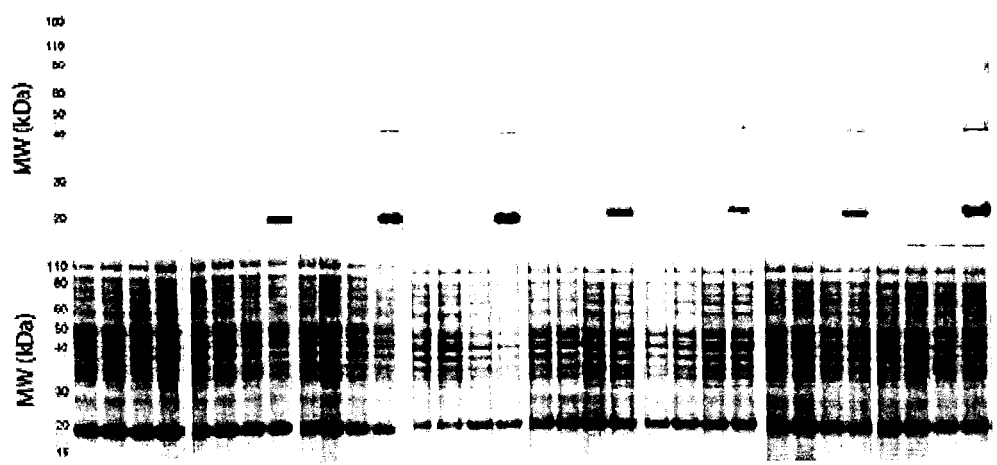

FIG. 8A-C shows Site-specific incorporation of 3 into proteins at diverse codons and specific proteome labelling using SORT-M in human cells. FIG. 8A: Western blot analysis demonstrates the efficient amino acid dependant expression of an mCherry-EGFP fusion protein separated by an amber stop codon bearing a C-terminal HA-tag (mCh-TAG-EGFP-HA) in HEK293T cells. Anti-FLAG detected tagged PylRS. FIG. 8B: Specific labelling of mCh-TAG-EGFP-HA (immunoprecipitated from 10$^6$ cells) with 4a (20 µM in 50 µL PBS, 1 h, RT) confirms the incorporation of 3 into protein in HEK293 cells. FIG. 8C: SORT-M labelling of 3 that is statistically incorporated into newly synthesised proteins across the whole proteome of mammalian cells directed by six different PylRS/PyltRNA$_{XXX}$ (mutants using 0.5 mM 3). Labeling with 4g (20 µM in PBS, 1 h, RT, as above). The amino acids in parentheses are the natural amino acids encoded by the endogenous tRNA bearing the corresponding anti-codon.

Figure 9A:
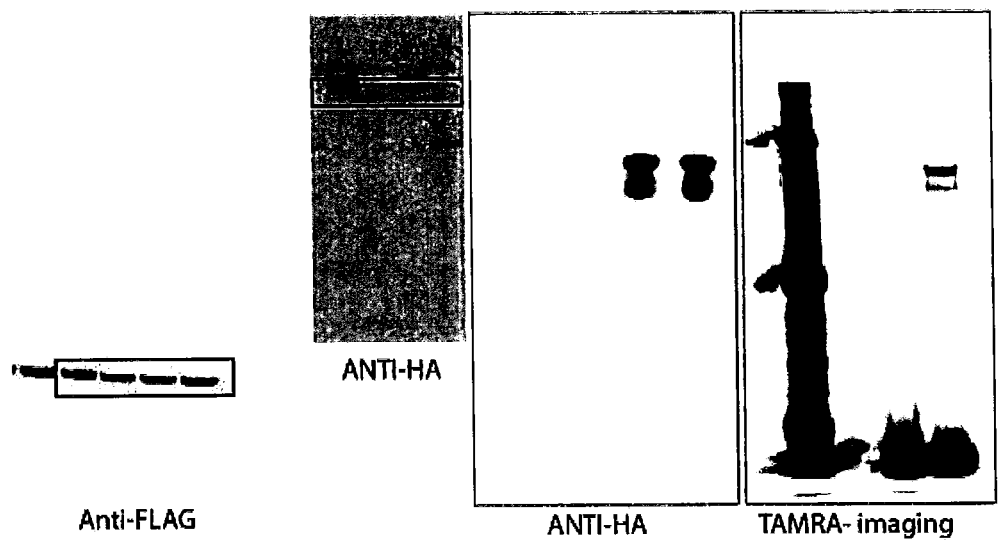
Figure 9B:
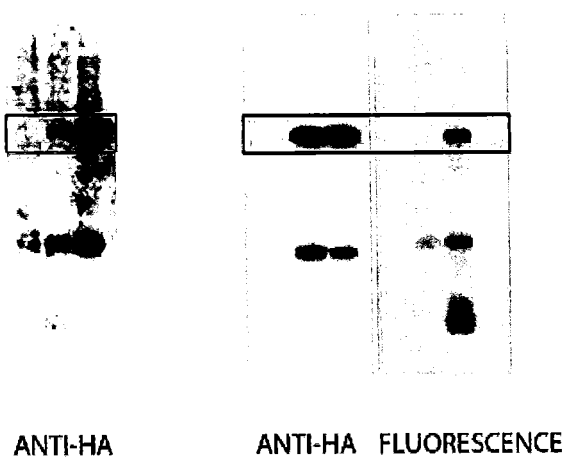
Figure 10A:
Figure 10B:
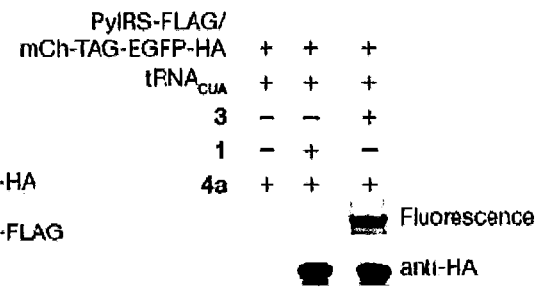
Figure 10C:
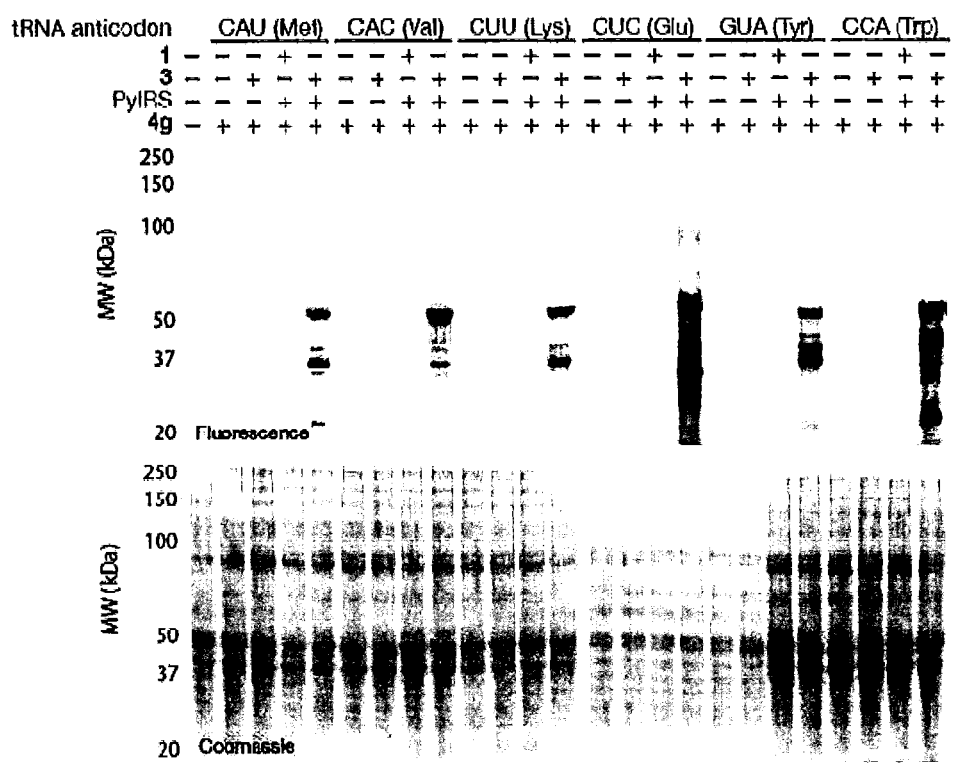

FIG. 9A: Full blots from FIG. 8A-C.
FIG. 9B: Full blots from FIG. 10A-C.
FIG. 10 shows Site-specific incorporation of amino acid 3 into protein produced in Drosophila melanogaster. FIG. 10A: Incorporation of 3 demonstrated by a dual luciferase reporter. Dual luciferase assay on ovary extract from 10 female flies expressing Triple-Rep-L in the presence or absence of 10 mM 1 or 10 mM 3. The data show a representative example from 1 of 3 biological replicates. The error bars represent the standard deviation of 3 technical replicates from a single biological replicate. FIG. 10B: Site-specific incorporation of 3 (or 1) into GFP_TAG_m-Cherry-HA in flies expressing PylRS/PyltRNA$_{CUA}$. The full-length protein resulting from unnatural amino acid incorporation is detected by anti-HA western blot. FIG. 10C: Specific labelling of encoded 3 with tetrazine probes. Flies were fed with no amino acid, amino acid 1 (500 flies) or amino acid 3 (100 flies). 5 times more flies were fed with 1 in order to generate comparable amount of reporter protein. The full-length protein containing the unnatural amino acid was immunoprecipitated from lysed ovaries with anti-GFP beads. The beads were labelled (4g, 4 µM, 200 µL, PBS, RT, 2 h) washed. Full length protein was detected by anti-HA blot and the same gel imaged on a fluorescence scanner shows specific fluorescent labelling of the protein incorporating 3 but not 1, confirming the identity of the incorporated amino acid.

Figure 11A:
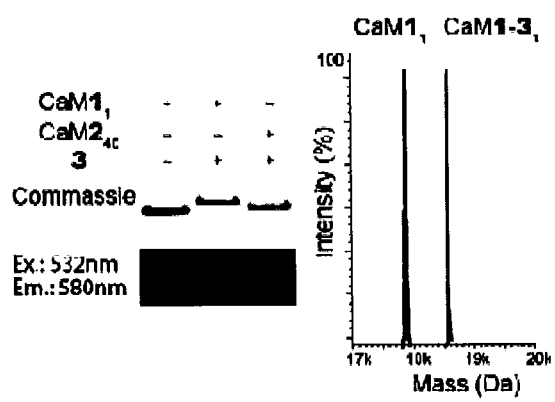
Figure 11B:
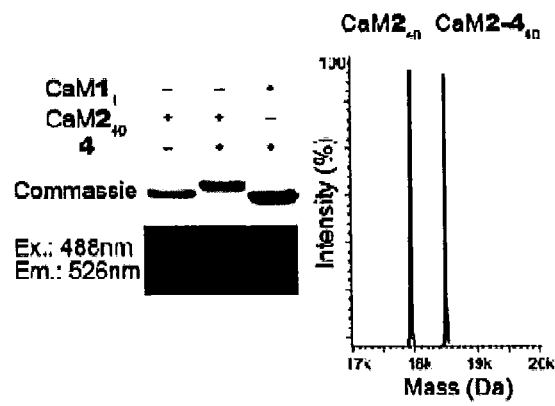

FIG. 11A-B (example 6): Specific protein labeling at genetically encoded unnatural amino acids 1 and 2. FIG. 11A: Genetically encoded 1, but not 2, in calmodulin is specifically labeled with probe 3. Coomassie and fluorescence images demonstrate the specificity of labeling and ESI MS before labelling (black, expected mass: 17875, found mass: 17874) and after labelling (red, expected mass: 18553, found mass: 18552) demonstrate the reaction is quantitative. FIG. 11B: Genetically encoded 2, but not 1, in calmodulin is specifically labeled with probe 4. Coomassie and fluorescence images demonstrate the specificity of labeling and ESI MS before labelling (black, expected mass: 17930, found mass: 17930) and after labelling (green, expected mass: 18484, found mass: 18485) demonstrate the reaction is quantitative. Raw (before deconvolution) ESI-MS spectra are not shown.

Figure 12A:
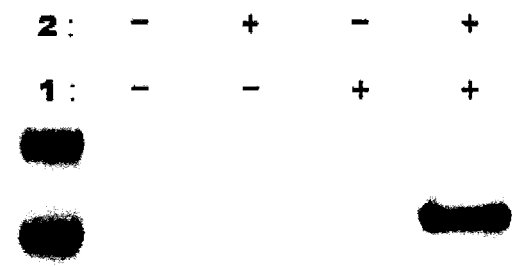
Figure 12B:
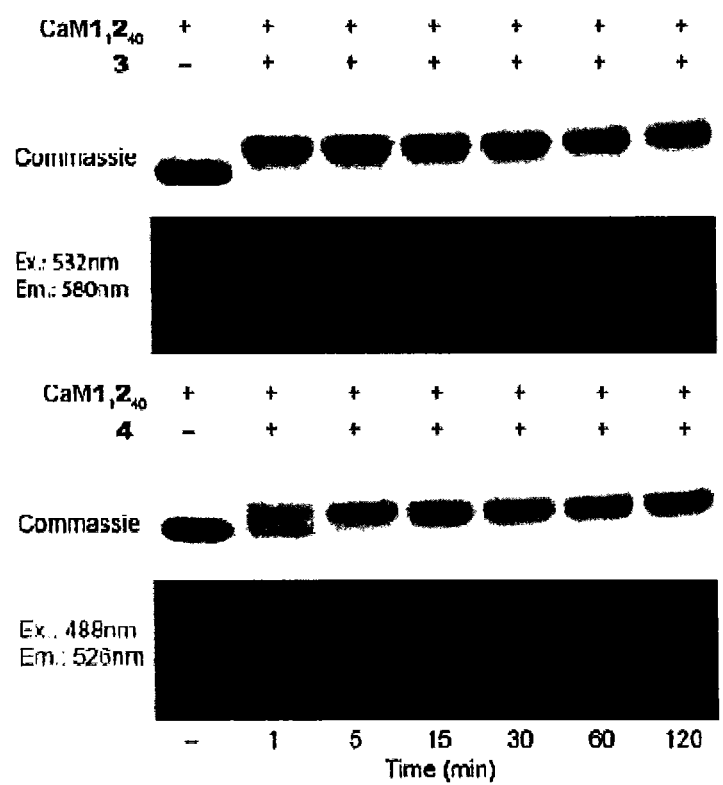

FIG. 12A-B (example 6): Incorporating 1 and 2 at positions 1 and 40 of Calmodulin and the kinetics of specific labelling. FIG. 12A: Expression was performed in E. coli bearing ribo-Q1, O-gst-cam$_{1TAG-40AGTA}$, the PylRS/tRNA$_{UACU}$ pair and the MjPrpRS/tRNA$_{CUA}$ pair. Amino acids 1 and 2 were used at 4 and 1 mM, respectively. FIG. 12B: Labelling time course for reaction of CaM1$_1$2$_{40}$ with 3 and 4. Each reaction was followed for 2 h by in gel fluorescence and mobility shift.

Figure 13A:
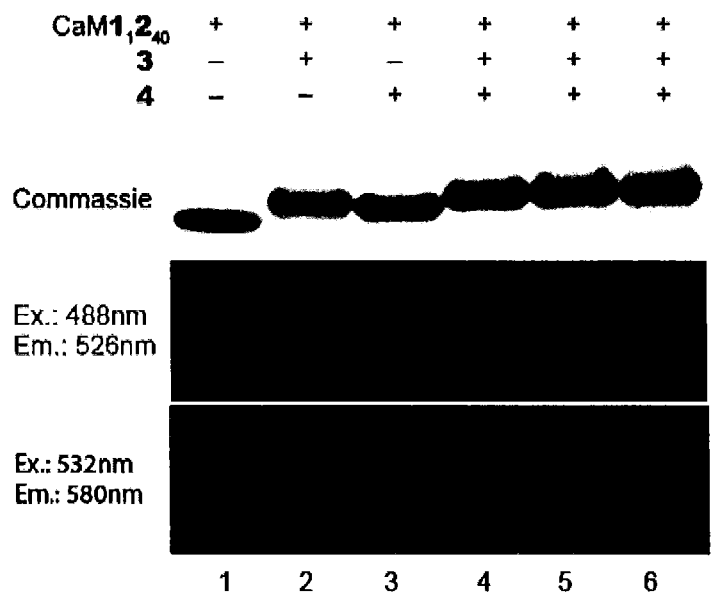
Figure 13B:
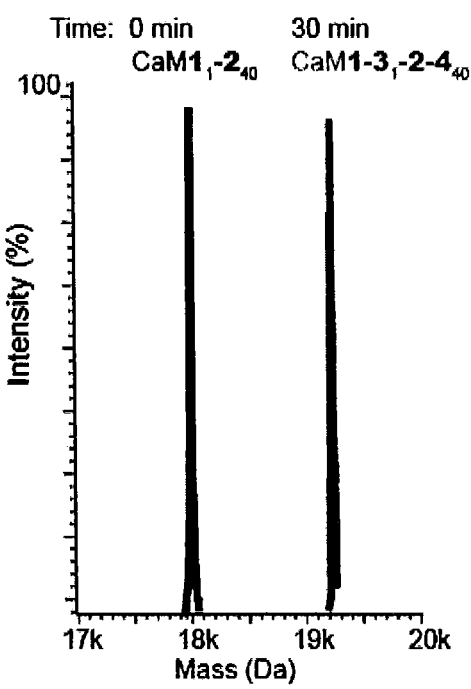

FIG. 13A-B (example 6): Concerted, quantitative one-pot, dual labeling of Calmodulin in 30 minutes. FIG. 13A: Dye dependent labeling of CaM1$_1$2$_{40}$; sequential labeling with purification after first labeling in lane 4, sequential labeling without purification in lane 5, one-pot dual labeling in lane 6. FIG. 13B: ESI-MS of one-pot protein labeling, before labeling (black, expected mass: 18000 found mass: 18000), after labeling (gold, expected mass: 19233 found mass: 19234). Raw (before deconvolution) ESI-MS spectra are not shown.

Figure 14A:
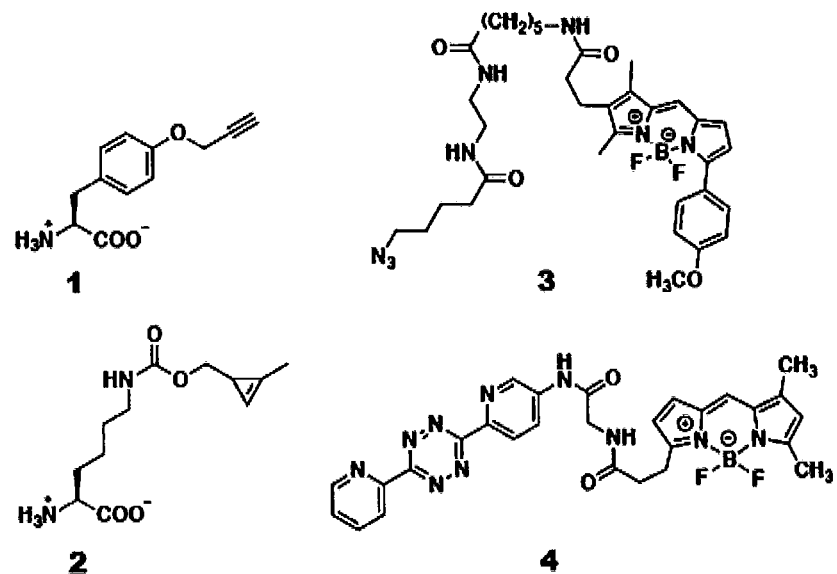
Figure 14B:
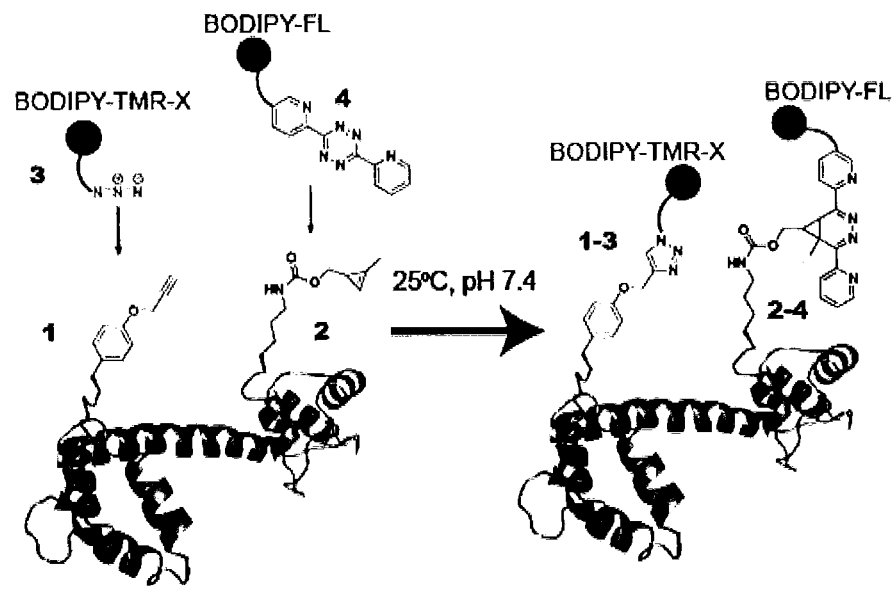

FIG. 14A-B shows a concerted, rapid, one-pot quantitative dual labelling of proteins in aqueous medium at physiological pH and temperature. FIG. 14A: Unnatural amino acids and fluorophores used in this example. FIG. 14B:

Concerted labeling at an encoded terminal alkyne and an encoded cyclopropene via mutually orthogonal cycloadditions.

FIG. 15 shows Amino acid and DNA sequence of *Drosophila* GFP-amber-mCherry-HA.

GFP (amino acid residues 1-238), Amber codon at position 248, mCherry (amino acid residues 255-489), HA tag (amino acid residues 491-499), Myc tag (amino acid residues 500-509), His tag (amino acid residues 510-515) and SV40 NLS (amino acid residues 523-528).

Figure 16:
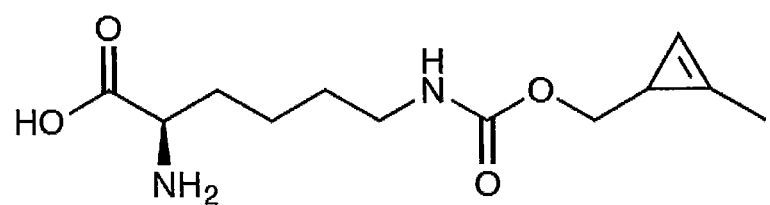

FIG. 16 shows structure of exemplary amino acid $N^\epsilon$-[((2-methylcycloprop-2-en-1-yl)methoxy)carbonyl]-1-lysine.

EXAMPLES—DESCRIPTION OF THE EMBODIMENTS

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

Chemical Syntheses—General Methods

All chemicals and solvents were purchased from Sigma-Alrich, Alfa Aesar or Fisher Scientific and used without further purification unless otherwise stated. Qualitative analysis by thin layer chromatography (TLC) was performed on aluminium sheets coated with silica (Merck TLC 60F-254). The spots were visualized under short wavelength ultra-violet lamp (254 nm) or stained with basic, aqueous potassium permanganate, ethanolic ninhydrin or vanillin. Flash column chromatography was performed with specified solvent systems on silica gel 60 (mesh 230-400).

LC-MS analysis was performed on Agilent 1200 machine. The solvents used consisted of 0.2% formic acid in water (buffer A) and 0.2% formic acid in acetonitrile (buffer B). LC was performed using Phenomenex Jupiter C18 column (150×2 mm, 5 µm) and monitored using variable wavelengths. Retention times ($R_t$) are recorded to a nearest 0.1 min and m/z ratio to nearest 0.01 mass units. The following programme was used for small molecule LC gradient: 0-1 min (A:B 10:90-10:90, 0.3 mL/min), 1-8 min (A:B 10:90-90:10, 0.3 mL/min), 8-10 min (A:B 90:10-90:10, 0.3 mL/min), 10-12 (A:B 90:10-10:90, 0.3 mL/min).

Mass spectrometry analysis following LC was carried out in ESI mode on a 6130 Quadrupole spectrometer and recorded in both positive and negative ion modes. NMR analysis was carried out on a Bruker 400 MHz instrument. All reported chemical shifts ($\delta$) relative to TMS were referenced to the residual protons in deuterated solvents used: $d_1$—chloroform ($^1H$ $\delta$=7.26 ppm, $^{13}C$ $\delta$=77.16 ppm), $d_6$—dimethylsulfoxide ($^1H$ $\delta$=2.49 ppm, $^{13}C$ $\delta$=39.52 ppm), $D_2O$ ($^1H$ $\delta$=4.70). APT or two-dimensional experiments (COSY, HSQC) were always performed to provide additional information used for analysis where needed. Coupling constants are given in Hz and described as: singlet—s, doublet—d, triplet—t, quartet—q, broad singlet—br, multiplet—m, doublet of doublets—dd, etc. and combinations thereof.

Protein Expression, Purification and Labelling of Site-Specifically Incorporated 3 in *E. coli*

Expression and purification of sfGFP-3 from *E. coli* Electrocompetent *E. coli* DH10B cells were co-transformed with pBK-MbPylRS and psfGFP150TAG PyIT[14, 26]. Transformed cells were recovered in S.O.B. (1 mL, supplemented with 0.2% glucose) for 1 h at 37° C. and used to inoculate LB containing 50 µg/mL kanamycin and 25 µg/mL tetracycline (LB-KT). The cells were incubated with shaking overnight at 37° C., 250 r.p.m. 1 mL of overnight culture was used to inoculate 100 mL of LB-KT½, the day culture was then incubated (37° C., 250 r.p.m). At $O.D._{600}$~0.3, the culture was divided equally and supplemented with either 3 (1 mM) or $H_2O$ (500 µL) and incubated further (37° C., 250 r.p.m). At $O.D._{600}$~0.6 protein expression was induced by the addition of arabinose (0.2%), after 4 h, the cells were harvested by centrifugation (4000 r.p.m, 20 min) and the pellet frozen until further use.

The frozen bacterial pellet was thawed on ice and resuspended in 2.5 mL lysis buffer (Bugbuster®, Novagen®, 50 µg/mL DNAse 1, Roche inhibitor cocktail and 20 mM imidazole). Cells were incubated (4° C., 30 minutes) then clarified by centrifugation (16000 g, 4° C., 30 minutes). The clarified lysates were transferred to fresh tubes and 100 µL Ni-NTA slurry added. The mixtures was incubated with agitation (4° C., 1 h) and then collected by centrifugation (1000 g, 4° C., 5 min). The beads were resuspended three times in 500 µL wash buffer (10 mM Tris-HCL, 40 mM imidazole, 200 mM NaCl, pH 8) and collected by centrifugation (1000 g, 4° C., 5 min). Finally, the beads were resuspended in 100 µL, elution buffer (10 mM Tris-HCL, 300 mM imidazole, 200 mM NaCl, pH 8), pelleted by centrifugation (1000 g, 4° C., 5 min) and the supernatant collected into fresh tubes. The elution was repeated three times with 100 µL of elution buffer. The purified proteins were analysed by 4-12% SDS-PAGE and LC-MS.

Protein Mass Spectrometry

Using an Agilent 1200 LC-MS system, ESI-MS was additionally carried out with a 6130 Quadrupole spectrometer. The solvent system consisted of 0.1% formic acid in $H_2O$ as buffer A, and 0.1% formic acid in acetonitrile (MeCN) as buffer B. Protein UV absorbance was monitored at 214 and 280 nm. Protein MS acquisition was carried out in positive ion mode and total protein masses were calculated by deconvolution within the MS Chemstation software (Agilent Technologies).

In Vitro Labeling of Purified sfGFP150-3

To Purified sfGFP150-1 or sfGFP150-3 protein (~30 µM, in elution buffer) was added 4a (10 molar equivalents, from a 2 mM stock solution in DMSO). The reactants were mixed by aspirating several times and the mixture then incubated at room temperature for 2 hours, a sample was analysed by ESI-MS. Following incubation the proteins were separated by 4-12% SDS-PAGE and analysed by using Typhoon Trio phosphoimager (GE Life Sciences).

Time Course of sfGFP150-3 and sfGFP150-NorK Labelling and Rate Constant Determination 2 nmol sfGFP-3 (10.6 µM) was labeled at room temperature by the addition of 20 nmol of tetrazine-dye conjugate 4a (10 µl of a 2 mM solution in DMSO) the samples were mixed by aspirating several times. At different time points, 8 µL aliquots were taken from the solution and quenched with a 700-fold excess of bicyclo[6.1.0]non-4-yn-9-yl-methanol (BCN) and plunged into liquid nitrogen. Samples were mixed with NuPAGE LDS sample buffer supplemented with 5% β-mercaptoethanol, heated for 10 min to 90° C. and analyzed by 4-12% SDS page. The amounts of labelled proteins were quantified by scanning the fluorescent bands with a Typhoon Trio phosphoimager (GE Life Sciences). Bands were quantified with the ImageQuant™ TL software (GE Life Sciences) using rubber band background subtraction. The rate constant was determined by fitting the data to a single-exponential equation. The calculated observed rate k' was divided by the concentration of 4a to obtain rate constant k for the reaction. Measurements were done in triplicate. All data processing was performed using Kaleidagraph software (Synergy Software, Reading, UK). For comparison the rate of labelling sfGFP bearing Ne-5-norbornene-2-yloxycarbonyl-L-lysine (NorK), a known substrate for PylRS, was determined in a similar way using 11.25 mM sfGFP bearing NorK at position 150 (SfGFP-NorK) and 20 equivalents of 4a.

Plasmid Construction for pBAD_wtT4L_MbPylT$_{XXX}$ pBAD_T4L83TAG_MbPylT$_{CUA}$ was digested with NcoI and KpnI restriction enzymes. The same restriction enzymes were also used to digest the wild-type T4 lysozyme from (D67) pBAD_wtT4L. The insert and backbone were ligated in 3:1 ratio using T4 DNA ligase (RT, 2 hours), transformed into chemically competent DH10B cells and grown on Tetracycline agar plates (37° C., 18 hours). Single colonies were picked and the correct sequence was confirmed by DNA sequencing (GATC Gmbh.), this step created pBAD_wtT4L_MbPylT$_{CUA}$. All final constructs were confirmed by DNA sequencing.

Proteomic Incorporation of 3 Via SORT in E. coli Expressing T4 Lysozyme

Electrocompetent E. coli DH10B cells (50 μL) were either doubly transformed with pBAD_wtT4L_MbPylT$_{XXX}$ plasmid (2 μL, necessary for expression of PyltRNA$_{XXX}$ and expresses T4 lysozyme under arabinose control) and pBKwtPylS plasmid (2 μL necessary for expression of PylRS) or singly transformed with pBAD_wtT4L_MbPylT$_{XXX}$ alone. Transformed cells were recovered in 1 mL S.O.B. (supplemented with 0.2% glucose) for 1 h at 37° C. 100 μL of the recovery was used to inoculate 5 mL LB-KT (50 μg/mL kanamycin and 25 μg/mL tetracycline) or LB-T (25 μg/mL tetracycline). Cultures were incubated overnight (37° C., 250 r.p.m.). 1 mL of each overnight culture was used to inoculate 15 mL ½ strength antibiotic containing media LB-T or LB-KT. Cultures were incubated at 37° C. until O.D.$_{600}$~0.3 was reached, at this time each culture was divided into 5 mL aliquots and supplemented with either 3 (0.1 mM final conc.) or H$_2$O (50 μL). Cultures were then incubated (37° C., 250 r.p.m.). At O.D.$_{600}$ 0.6. T4 lysozyme expression was initiated by the addition of arabinose (0.2% final conc.) and cultures incubated for a further 4 hours. Cells were harvested by centrifugation (4000 rpm, 4° C., 20 minutes) and then resuspended three times in 1 mL of ice cold PBS and collected by centrifugation (4000 rpm, 4° C., 20 minutes). The final bacterial pellets were immediately frozen for storage.

E. coli: Chemoselective Labelling Proteomes Tagged with 3 with Tetrazine-Dye Conjugates Frozen bacterial pellets were resuspended in 500 μL PBS and lysed using a bath sonicator (energy output 7.0, 90 s total sonication time. 10 s blasts and 20 s breaks, Misonix Sonicator 3000). The lysate was cleared by centrifugation (4° C., 14000 r.p.m., 30 min) and the supernatant aspirated to a fresh tube. To 50 μL of cleared cell lysate was added. 4a (2 mM, stock in DMSO, final concentration—20 μM). The reactions were mixed by aspirating several times and the samples then incubated in the dark (room temperature, 1 h). After this time 17 μL of 4×LDS sample buffer supplemented (6 mM BCN and 5% BME) was added and mixed by vortexing gently. Samples were incubated for 10 min before boiling at 90° C. for 10 min. Samples were analysed by 4-12% SDS-PAGE and fluorescent images were acquired using Typhoon Trio phosphoimager (GE Life Sciences).

The same protocol for fluorescent labelling of the E. Coli proteins was applied for all tetrazine-dye conjugates.

Site-Specific Incorporation of 3 in HEK293 Cells and Chemoselective Labelling with Tetrazine Probes Site Specific Incorporation of 3 in HEK Cells HEK293 Cells (ATCC CRL-1573) were plated on 24 well plates and grown to near confluence. The cells were transfected using Lipofectamine 2000 (Invitrogen) with the pMmPylS-mCherry-TAG-EGFP-HA construct and the p4CMVE-U6-PylT construct.[18] After 16 hrs growth with or without 1 mM 3 or with 1 mM 1 the cells were lysed on ice using RIPA buffer (Sigma). The lysates were spun down and the supernatant was added to 4×LDS sample buffer (Life technologies). The samples were run out by SDS-PAGE, transferred to a nitrocellulose membrane and blotted using primary rat anti-HA(clone 3F10, Roche, No. 867 423) and mouse anti-FLAG (clone G191, Abnova, cat. MAB8183), the secondary antibodies were anti-rat (Invitrogen, A11077) and anti-mouse (Cell Signaling Technologies, No. 7076S).

Labelling Site-Specifically Incorporated 3 from HEK 293 Cells

Adherent HEK293T cells (ATCC CRL-11268; 4×10⁶ per immunoprecipitation) were transfected with 7.5 μg p4CMVE-U6-PylT and 7.5 μg pPylRS-mCherry-TAG-EFGP-HA[18] using TransIT-293 transfection reagent according to the manufacturer's protocol and cultured for 48 hours in DMEM/10% FBS, supplemented with 0.5 mM 1 or 2 mM 3 where indicated. Cells were washed twice with PBS and lysed on ice for 30 minutes in 1 mL Lysis Buffer (150 mM NaCl, 1% Triton X-100, 50 mM Tris HCl (pH 8.0). After clarifying the lysate by centrifugation (10 min at 16000 g), HA-tagged proteins were captured using 50 μL μMACS HA-tag MicroBeads (Miltenyl Biotec) per transfection, washed with 0.5 mL RIPA (150 mM NaCl, 1% Igepal CA-630, 0.5% sodium deoxycholate, 0.1% SDS, 50 mM Tris HCl (pH 8.0) and 0.5 mL PBS (pH 7.4). The suspension of MicroBeads was incubated with 50 μL PBS (pH 7.4), 20 μM 4a for 1 hour and subsequently washed with 0.5 mL RIPA to remove excess dye. HA-tagged proteins were eluted from beads using SDS sample buffer and separated on a 4-12% Bis-Tris PAGE gel (Invitrogen), imaged using a Typhoon imager (GE Healthcare) and subsequently stained with DirectBlue or transferred for western blotting with Anti-HA-tag pAb-HRP-DirecT (MBL).

Expression and Purification of SfGFP from Mammalian Cells

HEK293T were transfected in a 10 cm tissue culture dish with 15 ug DNA using PEI and incubated for 72 hours with 3 (0.5 μM). Cells were washed twice with PBS and lysed in 1 mL RIPA buffer. Cleared lysate was added to 50 μL GFP-Trap® M (ChromoTek) and incubated for 4 h. Beads were washed with 1 mL RIPA, 1 mL PBS, 1 mL PBS+500 mM NaCl, 1 mL ddH2O and eluted in 1% Acetic Acid/ddH2O. Purified protein was labeled with 2 μM 4a for 4 h and loaded on a 4-12% Bis-Tris PAGE gel. Fluorescence of 4a-labeled sfGFP was detected on a Typhoon imager and gel was stained subsequently with DirectBlue.

Fly Plasmids, Transgenicflies and Culture

For all fly experiments no randomisation or blinding was used within this study

Plasmid Construction for Transgenic Fly Line Generation

The PyltRNA$_{CUA}$ anticodon was mutated using the QuikChange mutagenesis kit and pSG108 (pJet 1.2-U6-PylT, gift from S. Greiss) as a template. This contains the PylT gene without its 3' terminal CCA fused to the Drosophila U6-b promoter. Primers FMT19 and FMT20 were used to generate PyltRNA$_{TGC}$ to decode alanine codons (creating pFT18); primers FMT23 and FMT24 were used to generate PyltRNAccr to decode serine codons (creating pFT20); primers FMT27 and FMT28 were used to generate PyltRNA$_{CAG}$ to decode leucine codons (creating pFT22) and primers FMT29 and FMT30 were used to generate PyltRNA$_{CAT}$ to decode methionine codons (creating pFT23). The mutated tRNA expression cassettes were subcloned from pFT18, pFT20, pFT22 and pFT23 into pUC18 using EcoRI and HinDIII then multimerised using AsiSI, BamHI and BglII to create 2, then 4 copies of the tRNA. The 4 copy versions of the tRNA cassette were subcloned into pSG118 using AsiSI and MluI to create pFT58 (Ala), pFT60 (Ser), pFT62 (Leu) and pFT63 (Met). pSG118 contains the M. mazei PylRS gene.[20]

Fly Lines and Culture Conditions

Transgenic lines were created by P element insertion using a Drosophila embryo injection service (BestGene Inc.). Lines were generated using the following plasmids: pFT58 (Ala), pFT60 (Ser), pFT62 (Leu) and pFT63 (Met). nos-Gal4-VP16 (Bloomington 4937) and MS1096-Gal4 (Bloomington 8860) were used as Gal4 drivers. All flies were grown at 25° C. on standard Iberian medium. Flies were fed unnatural amino acids by mixing dried yeast with the appropriate concentration of amino acid (usually 10 mM) diluted in dH$_2$O to make a paste. Ovaries were prepared from females that were grown on Iberian fly food supplemented with a yeast paste with or without the amino acid for a minimum of 48 hours. For proteome labelling experiments transgenic male flies of constructs FT58, FT60, FT62 and FT63 were crossed with nos-vp16-GAL4 virgins to generate FT58/nos-vp16-GAL4, FT60/nos-vp16-GAL4, FT62/nos-vp16-GAL4 and FT63/nos-vp16-GAL4 respectively.

Site Specific Incorporation of 3 in D. melanogaster

Luciferase Assays

Ovaries from 10 females of Triple Rep-L flies recombined with nos-Gal4-VP16 fed 3, 1 or no amino acid were dissected in 100 μl 1× Passive lysis buffer and processed for luciferase assays as previously described[20].

Immunoprecipitation and Labelling of Site Specifically Incorporated 3

Ovaries from 100 (for control and 3) or 500 (for 1) females were dissected in PBS then lysed in 300 or 1500 μl RIPA buffer containing ix complete protease inhibitor cocktail (Roche). A sample was taken into 4×LDS buffer as a total lysate control then the remainder was used for immunoprecipitation with GFP-TRAP agarose beads (Chromotek) following the manufacturer's instructions. The total volume of the IP was 3 ml. After overnight incubation, the beads were washed 2× with RIPA buffer then 2× with PBS. For tetrazine labeling, the beads were resuspended in 200 μl PBS+4 μM 4g and incubated for 2 hours on a roller at RT. The beads were washed 3 times with 500 μL of wash buffer then resuspended in 4×LDS sample buffer.

Example 1—Synthesis of N$^\varepsilon$-[((2-methylcycloprop-2-en-1-yl)methoxy)carbonyl]-L-lysine 3

A class of reaction useful in protein labelling is the very rapid and specific inverse electron demand Diels-Alder reaction between strained alkenes (or alkynes) and tetrazines.[21-25]

Figure 1A:
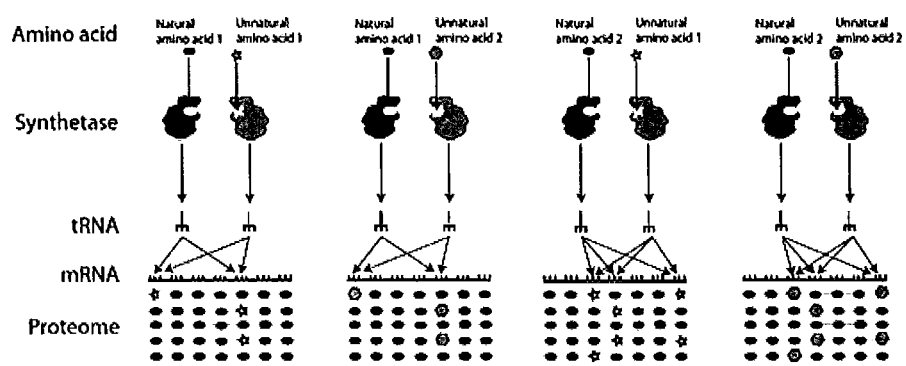
FIG. 1A-B: SORT-M enables proteome tagging and labelling at diverse codons, with diverse chemistries, and in genetically targeted cells and tissues.
Figure 1B:
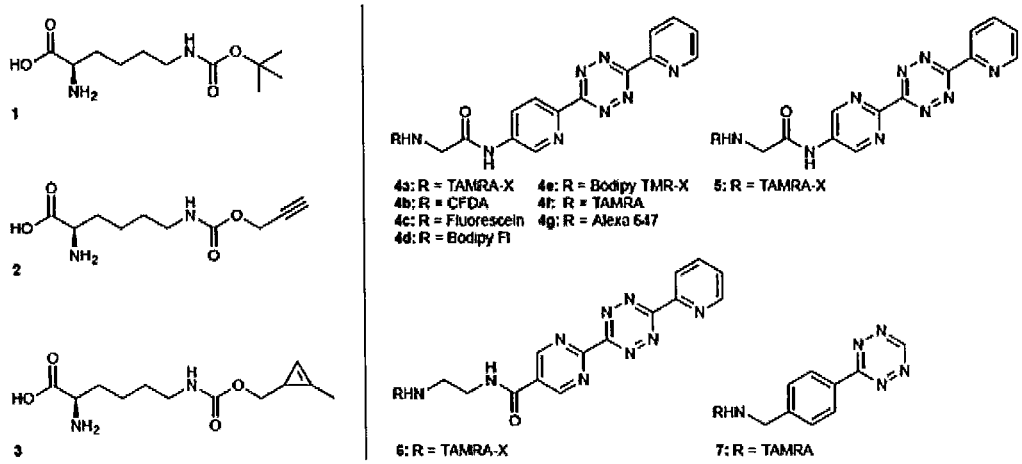

While we, and others, have previously encoded unnatural amino acids bearing strained alkenes, alkynes and tetrazines via genetic code expansion and demonstrated their use for site-specific protein labelling via inverse electron demand Diels-Alder reactions,[26-30] all the molecules used to date are rather large. We have previously shown that a variety of carbamate derivatives of lysine are good substrates for PylRS,[31] and it has been demonstrated that 1,3 disubstituted cyclopropenes, unlike 3,3 disubstituted cyclopropenes,[32,24] react efficiently with tetrazines.[22] We therefore designed and synthesized a carbamate derivative of lysine, bearing a 1,3 disubstituted cyclopropene (N$^\varepsilon$-[((2-methylcycloprop-2-en-1-yl)methoxy)carbonyl]-L-lysine 3, FIG. 1b), for incorporation into proteins and labelling with tetrazines.

Synthesis of Methylcycloprop-2-en-1-yl}methoxy)carbonyl]-L-lysine (3)

Scheme 1

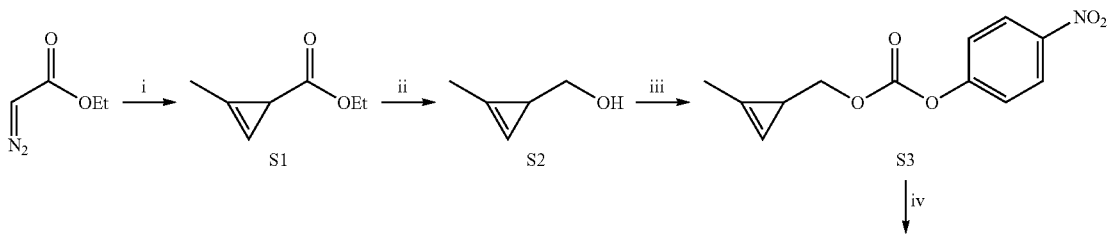

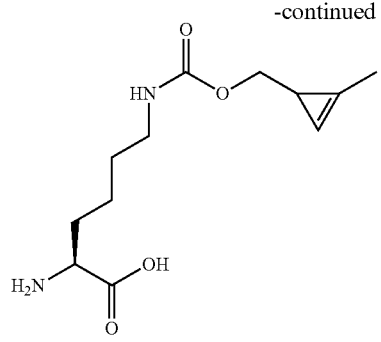 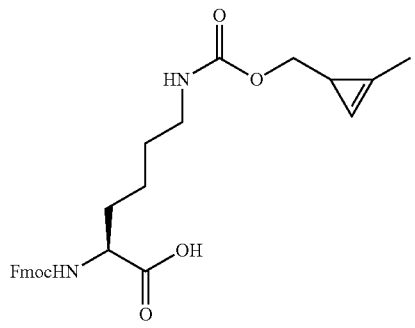

Synthesis of N$^\varepsilon$-[({2-methylcycloprop-2-en-1-yl}methoxy)carbonyl]-L-lysine 3. Reagents and conditions:
i. Rh$_2$(OAc)$_4$, propyne, CH$_2$Cl$_2$, 4° C. to RT, 75% yield;
ii. DIBAL-H, CH$_2$Cl$_2$, 0° C. to RT;
iii. 4-nitrophenyl chloroformate, Hunig's base, CH$_2$Cl$_2$, RT, 73% yield;
iv. Fmoc-Lys-OH, Hunig's base. THF/DMF, 4° C. to RT, 82% yield;
v. NaOH, THF/H$_2$O, RT, 68% yield.

i. Ethyl 2-methylcycloprop-2-ene-1-carboxylate S1

A 100 mL 2-neck round bottom flask was charged with CH$_2$Cl$_2$ (2 mL) and rhodium acetate (442 mg, 1 mmol, 0.05 eq), and fitted with a dry ice condenser. Propyne (approx. 10 mL) was condensed into the rhodium acetate suspension and the flask lowered into a water bath (20° C.), a steady reflux of propyne was obtained. Ethyl diazoacetate (2.1 mL, 20 mmol, 1 eq) was added to the stirred propyne solution drop-wise over 1 h using a syringe pump. The reaction was stirred at room temperature for a further 10 minutes whereby TLC analysis showed the reaction to be complete by after this time. The cyclopropene product was then purified by silica gel flash column chromatography eluting with pentane and diethyl ether (90:10). This gave the desired product S1 as a colourless volatile liquid (1.9 g, 75% yield). $^1$H NMR analysis $\delta_H$ (400 MHz, CDCl$_3$) 6.35 (1H, t, J 1.4), 4.18-4.09 (2H, m), 2.16 (3H, d, J 1.3), 2.12 (1H, d, J 1.6), 1.26 (3H, t, J 7.1); LRMS m/z (ES$^+$) 127.2 [M+H]$^+$.

These values are in good agreement with literature. {Liao, 2004 #1} ii. and iii. (2-Methylcycloprop-2-en-1-yl)methyl (4-nitrophenyl) Carbonate S3

DIBAL-H (22.5 mL of a 1M solution in CH$_2$Cl$_2$, 22.5 mmol, 1.5 eq) was added drop-wise to a stirred solution of cyclopropene ester S1 (1.9 g, 15 mmol, 1 eq) in CH$_2$Cl$_2$ (15 mL) at −10° C. The reaction was stirred at −10° C. for 20 minutes before quenching with the cautious addition of H$_2$O (1 mL), then NaOH (1 mL of a 1 M solution in H$_2$O) and H$_2$O (2.3 mL). The mixture was stirred for a further 2 h at room temperature before it was dried (Na$_2$SO$_4$) and filtered. Hunig's base (3.9 mL, 22.5 mmol, 1.5 eq) was added to the filtrate (containing crude cyclopropene alcohol S2) followed by the addition of 4-nitrophenyl chloroformate (3.3 g, 16.5 mmol, 1.1 eq). After stirring at room temperature for 18 hours a significant colourless precipitate formed, and TLC analysis showed complete consumption of the crude cyclopropene alcohol S2. The reaction was diluted with CH$_2$Cl$_2$ and then dry loaded onto silica gel, whereby the activated carbonate S3 was purified by silica gel column chromatography eluting with ethyl acetate and hexane (20:80). This gave the desired cyclopropene carbonate S3 as a colourless oil (2.7 g, 73% yield over 2 steps). $^1$H NMR analysis $\delta_H$ (400 MHz, CDCl$_3$) 8.28 (2H, d, J 9.2), 7.39 (2H, d, J 9.2), 6.62 (1H, s), 4.21 (1H, dd, J 10.9, 5.3), 4.14 (1H, dd, J 10.9, 5.3), 2.18 (3H, d, 1.3), 1.78 (1H, td, J 5.3, 1.3).

iv. N$^\alpha$-(Fmoc)-N$^\varepsilon$-(((2-methylcycloprop-2-en-1-yl)methoxy)carbonyl)-L-lysine S4

Fmoc-Lys-OH.HCl (6.7 g, 16.5 mmol, 1.5 eq) was dissolved in THF (30 mL) and DMF (10 mL), to this solution was added Hünig's base (9.0 mL, 55.0 mmol, 5 eq) followed by cyclopropene carbonate S3 (2.7 g, 11.0 mmol, 1 eq) an immediate yellow coloration was observed upon addition of the carbonate. The reaction was stirred at room temperature for 6 hours and was adjudged complete by the consumption of starting material after this time as shown by TLC analysis. The crude reaction mixture was dry loaded onto silica gel and the major product purified by silica gel column chromatography eluting with ethyl acetate, hexane and acetic acid (50:49:1 then 99:0:1). This gave the desired product S4 as a colourless gum (4.3 g, 82% yield). $^1$H NMR analysis $\delta_H$ (400 MHz, CDCl$_3$) 7.77 (2H, t, J 7.6), 7.65-7.55 (2H, m), 7.39 (2H, t, J 7.6), 7.31 (2H, t, J 7.3), 6.54 (1H, s), 5.68-5.57 (1H, m), 4.84 (1H, br-s), 4.44-4.32 (2H, m), 4.22 (1H, t, J 7.0), 3.98-3.87 (1H, m), 3.17-3.09 (2H, m), 2.15-2.06 (6H, m), 1.99-1.86 (1H, m), 1.84-1.70 (1H, m), 1.68-1.59 (1H, m), 1.58-1.34 (2H, m); LRMS m/z (ES$^+$) 479.3 [M+H]$^+$, 501.3 [M+Na]$^+$, m/z (ES$^-$) 477.2 [M−H]$^-$.

N$^\varepsilon$-[({2-methylcycloprop-2-en-1-yl}methoxy)carbonyl]-L-lysine 3

N$^\varepsilon$-(Fmoc)-N$^\varepsilon$-(((2-methylcycloprop-2-en-1-yl)methoxy)carbonyl)-L-lysine S4 (3.5 g, 7.0 mmol, 1 eq) was dissolved in THF and H$_2$O (3:1 40 mL), to this solution was added sodium hydroxide (0.9 g, 22.6 mmol, 3.1 eq). The reaction was stirred at room temperature for 8 hours after which time the reaction was adjudged complete by LC-MS analysis. The reaction mixture was diluted with H$_2$O (100 mL) and the pH adjusted to ~5 by the addition of HCl (1M). The aqueous solution was washed with Et$_2$O (5×100 mL), then concentrated to dryness yielding a colourless solid. The solid was purified by preparative HPLC, the product fractions were combined and the solvent removed by freeze-drying. This gave N$^\varepsilon$-[({2-methylcycloprop-2-en-1-yl}methoxy)carbonyl]-L-lysine 3 as a colourless solid. $\delta_H$ (400 MHz, D$_2$O) 6.45 (1H, s), 3.90-3.61 (2H, m), 3.09 (1H, t, J 6.4), 2.98-2.86 (2H, m), 1.92 (3H, s), 1.52-1.37 (2H, m), 1.37-1.22 (2H, m), 1.21-1.08 (2H, m), 0.83 (1H, d, J 5.2). LRMS m/z (ES$^+$) 257.2 [M+H]$^+$, m/z (ES$^-$) 255.2 [M−H]$^-$. $\delta_C$ (100 MHz, D$_2$O) 101.1 (CH), 72.3 (CH$_2$), 55.9 (CH), 40.2 (CH$_2$), 34.3 (CH$_2$), 28.9 (CH$_2$), 20.3 (CH$_2$), 16.6 (CH$_3$), 10.8 (CH) HRMS (ES$^+$) Found: (M+Na)$^+$ 279.1302. C$_{12}$H$_{20}$O$_4$N$_2$Na required M$^+$, 279.1315.

Example 2—Encoding the Site-Specific Incorporation of 3 in E. coli

Figure 2A:
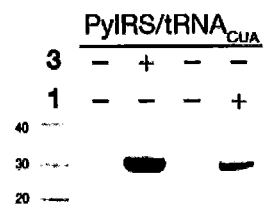
Figure 2B:
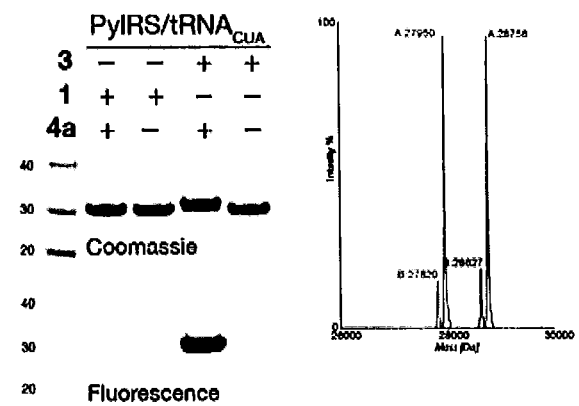

We demonstrated that 3 is efficiently and site-specifically incorporated into recombinant proteins in response to the amber codon using the PylRSARNA$_{CUA}$ pair and an SfGFP gene bearing an amber codon at position 150 (Supplementary FIG. 2a). The yield of protein is 8 mg per litre of culture, which is greater than that obtained for a well-established efficient substrate for PylRS N$^\varepsilon$-[(tert-butoxy)carbonyl]-L-lysine 1 (4 mg per litre of culture)[33] Electrospray ionisation mass spectrometry of SfGFP bearing 3 at position 150 (SfGFP-3) confirms the incorporation of the unnatural amino acid (Supplementary FIG. 2b). SfGFP-3 was specifically labelled with the fluorescent tetrazine probe 4a, while SfGFP-1 was left unlabelled (Supplementary FIG. 2b). 2 nmol of SfGFP-3 was quantitatively labelled with 10 equivalents of 4a in 30 minutes, as judged by both fluorescence imaging and mass spectrometry (Supplementary FIG. 2b). The second order rate constant for labelling SfGFP-3 with 4a was 27±1.8 M$^{-1}$ s$^{-1}$ (Supplementary FIG. 2c)[26]

Figure 4A:
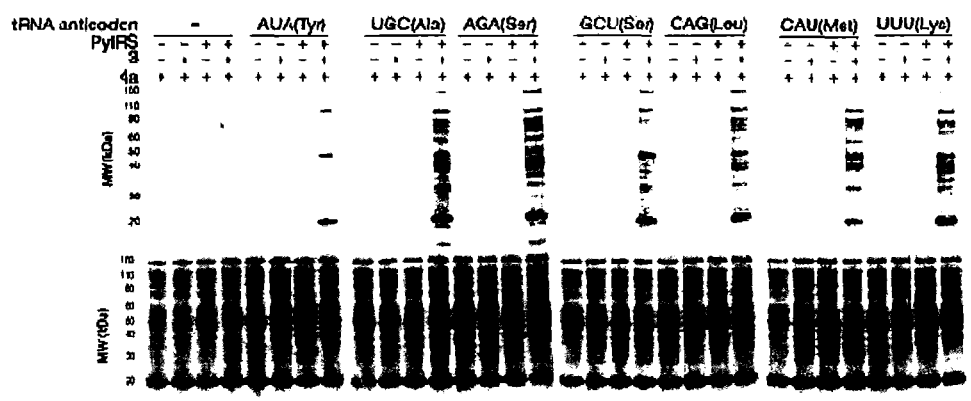
FIG. 4A-B Shows SORT-M Enables Codon Specific Proteome Tagging and Labelling in *E. coli*
Figure 4B:
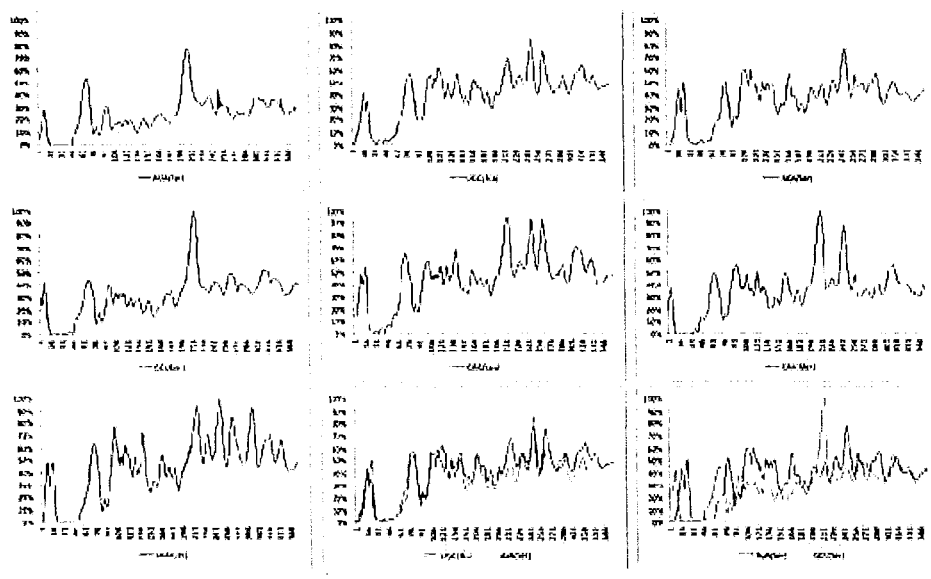
Figure 5:
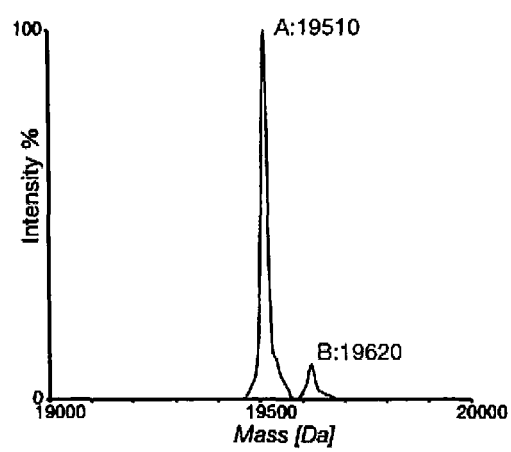
FIG. 5 Shows Specific Amino Acid Replacement in SORT Demonstrated by ESI-MS

Since PylRS does not recognize the anticodon of its cognate tRNA[34] it is possible to alter the anticodon of this tRNA to decode distinct codons. We created a new tRNA in which the anticodon of PyltRNA$_{CUA}$ was converted from CUA to UUU (Supplementary Table 1), to decode a set of lysine codons. We added 0.1 mM 3 to cells containing PylRS, PyltRNA$_{UUU}$, and the gene for T4 lysozyme. Following expression of T4 lysozyme we detected proteins in the lysate bearing 3 with the tetrazine probe 4a (20 microM 1 h, Supplementary FIG. 3). Control experiments show that the observed labelling requires the presence of the synthetase and tRNA, and electrospray ionization mass spectrometry demonstrates the incorporation of 3 in place of lysine in T4 lysozyme (Supplementary FIG. 4). The addition of 3 (0.1 or 0.5 mM) has little or no effect on cell growth (Supplementary FIG. 5) suggesting that the amino acid is not toxic at the concentration used, and there is substantial labelling within 1 h of amino acid addition (Supplementary FIG. 6).

Example 3—Genetic Encoding of 3 in Human Cells

Full-length mCherry-3-GFP-HA was expressed in HEK293 cells carrying the PylRSARNA$_{CUA}$ pair and mCherry-TAG-EGFP-HA (a fusion between the mCherry gene and the EGFP gene with a C-terminal HA tag, separated by the amber stop codon (TAG)).[18] Full-length protein was detected only in the presence of the 3 (FIG. 8a. Full gels in Supplementary FIG. 11). mCherry-3-EGFP-HA was selectively labelled with 4a, while mCherry-1-EGFP-HA was not labelled (FIG. 8b)[18] demonstrating the site-specific incorporation of 3 with the PylRS/tRNA$_{CUA}$ pair in human cells.

Example 4—Genetic Encoding of 3 in D. melanogaster

We demonstrated that 3 can be site specifically incorporated into proteins in D. melanogaster. To achieve this, we used flies containing the PylRS/tRNA$_{CUA}$ pair (with the tRNA expressed ubiquitously from a U6 promoter and UAS-PylRS expression directed to ovaries using a nos-vp16-GAL4 driver), and a dual luciferase reporter bearing an amber codon between firefly and renilla luciferase.[20] We observe a strong luciferase signal that is dependent on the addition of 1 or 3, and the dual luciferase signal is larger with 3. These experiments demonstrate that 3 is taken up by flies and is more efficiently incorporated in vivo in response to an amber codon than 1 (FIG. 10a), a known excellent substrate for PylRS. 3 may be supplied by feeding food supplemented with amino acid 3 at 10 mM. In additional experiments, we demonstrated by western blot the efficient incorporation of 3 into a GFP-TAG-mCherry-HA construct (Supplementary FIG. 15) expressed in ovaries[20] (FIG. 10b), and the specific fluorescent labelling of the incorporated amino acid with 4g (FIG. 10c).

Example 5—Synthesis of Tetrazine-BODIPY FL 4d

Scheme 3

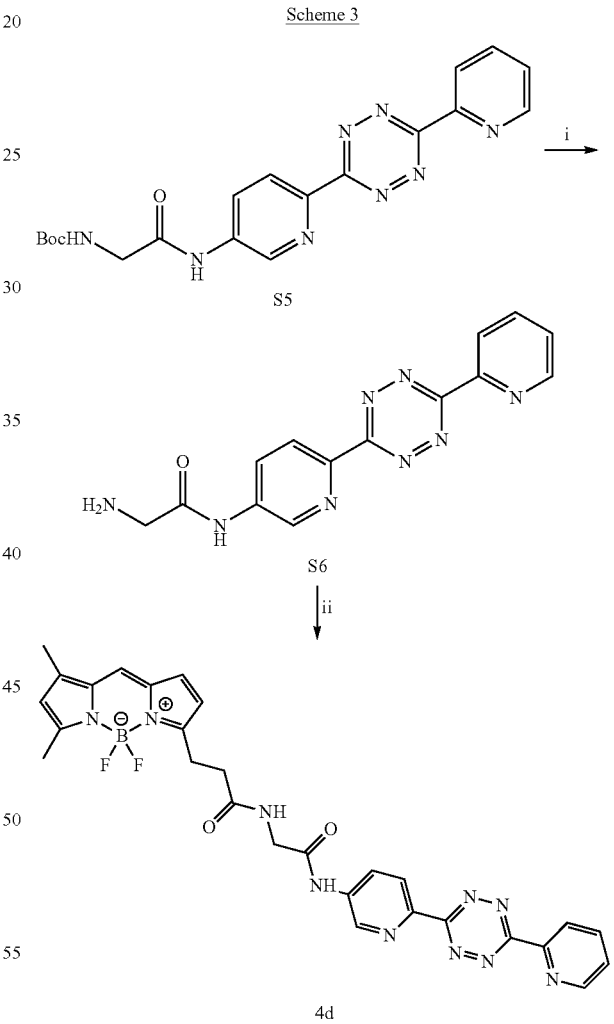

Synthesis of tetrazine-biotin 4d. Reagents and conditions: i. HCl dioxane, RT, 100% yield; ii. Bodipy-FL-NHS ester, Hunig's base, DMF, RT.

Boc-protected Tetrazine S6 was synthesized using the procedure reported earlier[6]. 4M HCl in dioxane (500 µL, 2.0 mmol) was added to a stirring solution of Tetrazine S5 (8 mg, 0.02 mmol) in DCM (500 µL). The reaction was carried out for 2 h at room temperature and subsequently the solvent was removed under reduced pressure to yield primary amine hydrochloride S6 as a pink solid (6 mg, 0.02 mmol, 100%). The compound was directly used in the next step without any further purification.

ii. 4d

BODIPY FL succinimidyl ester (5 mg, 0.013 mmol, Life technologies) and Hünig's base (50 µl, 2.8 mmol) were added to the solution of Tetrazine-amine S2 (6 mg, 0.02 mmol) in dry DMF (1 mL). The reaction mixture was stirred at room temperature for 16 h. The reaction mixture was diluted with 4 ml of water and the product was purified by semi-preparative reverse phase HPLC using a gradient from 10% to 90% of buffer B in buffer A (buffer A: $H_2O$; bufferB: acetonitrile). The identity and purity of the tetrazine-BODIPY FL conjugate 4d was confirmed by LC-MS. ESI-MS: [M−H]⁻, calcd. 581.38, found 581.2.

Summary of Examples 1 to 5

We have characterized the synthesis of, and the genetically encoded, site-specific incorporation of a cyclopropene containing amino acid 3, and demonstrated the quantitative labelling of 3, with tetrazine probes, in proteins expressed in E. coli, mammalian cells and D. melanogaster, thereby showing the widespread utility and industrial application of the present invention.

SUPPLEMENTARY REFERENCES TO EXAMPLES 1 to 5

1. Gautier, A. et al. Genetically Encoded Photocontrol of Protein Localization in Mammalian Cells. *Journal of the American Chemical Society* 132, 4086-4088 (2010).
2. Karp, N A, Kreil, D. P. & Lilley, K. S. Determining a significant change in protein expression with DeCyder during a pair-wise comparison using two-dimensional difference gel electrophoresis. *Proteomics* 4, 1421-1432 (2004).
3. Karp, N. A. & Lilley, K. S. Design and analysis issues in quantitative proteomics studies. *Proteomics* 7 Suppl 1, 42-50 (2007).
4. Lilley, K. S. in Current Protocols in Protein Science (John Wiley & Sons, Inc., 2001).
5. Von Stetina, J. R., Lafever, K. S., Rubin, M. & Drummond-Barbosa, D. A Genetic Screen for Dominant Enhancers of the Cell-Cycle Regulator alpha-Endosulfine Identifies Matrimony as a Strong Functional Interactor in *Drosophila*. G3 (Bethesda) 1, 607-613 (2011).
6. Lang, K. et al. Genetically encoded norbornene directs site-specific cellular protein labelling via a rapid bioorthogonal reaction. *Nat Chem* 4, 298-304 (2012).

Example 6—Dual Labelling of Proteins

The ability to attach two distinct molecules to programmed sites in proteins will facilitate a variety of applications including FRET[1,2] to study protein structure, conformation and dynamics. Several approaches for doubly labeling proteins have been reported. One approach relies on the installation of one unnatural amino acid that is specifically labeled in combination with cysteine thiol labeling, but this approach is generally limited to proteins that do not contain free thiols.[3,4] Chemical ligation approaches can be combined with the genetic encoding of a single unnatural amino acid for protein labeling,[5] but this may limit the size and/or sites that may be labeled. Perhaps the most generally applicable approach for protein double labelling is based on the genetic incorporation of two distinct amino acids in response to two distinct codons introduced at user defined sites in the gene of interest.

An ideal strategy for dual labeling requires i) the efficient, cellular, incorporation of two distinct unnatural amino acids into a protein that can be labelled in mutually orthogonal reactions, and the development of mutually orthogonal reactions that allow the simultaneous addition of two molecules to the protein for rapid, quantitative labelling of the protein in aqueous media at physiological pH, temperature and pressure.

Scheme A (FIG. 14) shows concerted, rapid, one-pot quantitative dual labelling of proteins in aqueous medium at physiological pH and temperature. (a) Unnatural amino acids and fluorophores used in this example. (b) Concerted labeling at an encoded terminal alkyne and an encoded cyclopropene via mutually orthogonal cycloadditions.

The cellular, genetically directed incorporation of two distinct unnatural amino acids into proteins has been demonstrated in response to an amber and quadruplet codon,[6] two distinct stop codons,[7,8] or two distinct quadruplet codons.[9] We previously demonstrated the evolution of an orthogonal ribosome (ribo-Q1) that efficiently reads quadruplet codons and amber codons on orthogonal mRNA using cognate extended anticodon tRNAs or amber suppressors respectively.[6] We demonstrated that the pyrrolysyl-tRNA synthetase/tRNA pair and synthetically evolved derivatives of the MjTyrRS/tRNA pair are mutually orthogonal in their aminoacylation specificity and can be used to direct the incorporation of pairs of unnatural amino acids in response to amber and quadruplet codons.[6] We recently described several major advances in this system, including the evolution of a series of quadruplet decoding tRNAs based on the pyrrolysyl-tRNA synthetase (PylRS)/tRNA pair that efficiently direct the incorporation of unnatural amino acids in response to quadruplet codons using the evolved orthogonal translation machinery.[9] We demonstrated the very efficient incorporation of a matrix of pairs of unnatural amino acids using the evolved PylRS/tRNA$_{UACU}$ pair and derivatives of the MjTyrRS/tRNA$_{CUA}$ pair with orthogonal messages bearing TAG and AGTA codons and ribo-Q1.[9]

A limited range of chemistries have been investigated for the double labeling of proteins containing pairs of unnatural amino acids. The incorporation of azide- and alkyne-containing amino acids, and their non-quantitative labeling with alkyne and azide based fluorophores has been reported[7], but this is not ideal for double labeling of proteins; if the encoded azide and alkyne are in proximity they can react to form a triazole in the protein, a strategy which allows genetically directed protein stapling,[6] but precludes labeling with probes. Moreover, an efficient one-pot reaction is not feasible because of the reaction between azide- and alkyne-bearing probes with each other. The incorporation of ketone and azide containing amino acids has been reported,[8,10] which allows one-pot reaction of the encoded ketone with alpha effect nucleophiles, and the azides with alkyne probes.[10] However this approach is problematic because encoded azides are subject to reduction in many proteins when expressed in E. coli,[8,11] which will prevents quantitative labeling. Moreover, ketone labeling with alpha effect nucleophiles is very slow (rate constant approximately $10^{-4}$ $M^{-1}$ $s^{-1}$) and the reaction is optimal at pH4-5.5,[12] which limits its utility for many proteins that are denatured or precipitate when kept for long periods under acidic conditions. We recently genetically installed a deactivated tetrazine containing amino acid[13] and a norbornene containing amino acid[14-16] into proteins using our optimized orthogonal translation system.[9] Because the rate of inverse electron demand Diels Alder reaction between the deactivated tetrazine and norbornene is very slow, but the tetrazine can react with bicyclononyne based probes and the norbornene can react with activated tetrazine probes we were able to use this approach to specifically and quantitatively double label proteins.[9] While this approach has the advantage of proceeding in aqueous media at physiological pH, temperature and pressure; it does require sequential labeling steps (to avoid inverse electron Demand reactions between probes), each of which takes several hours, with purification between steps. All approaches reported to date for doubly labeling proteins at genetically encoded unnatural amino acids take tens of hours to days to reach completion.

An ideal approach to double label proteins would allow rapid one-pot labeling of genetically installed bio-orthogonal functional groups, proceed rapidly in aqueous media at physiological pH, temperature and pressure and be implemented simply by adding the labeling reagents to a recombinant protein bearing the site specifically incorporated bioorthogonal groups. A promising pair of mutually orthogonal reactions for one-pot labeling under aqueous conditions at physiological pH are the Cu(I)-catalysed 3+2 cycloaddition between azides and terminal alkynes,[17] and the inverse electron demand Diels Alder reaction of a strained alkenes and a tetrazine[18-23] (FIG. 11). The reaction of strained alkynes and azides can also be orthogonal to strained alkene tetrazine reactions, but since tetrazines react with strained alkynes this approach requires careful tuning of the rate constants for each reaction.[24] No combination of 3+2 cycloaddition and inverse electron demand Diels Alder reaction has been demonstrated for protein labelling.

We demonstrated in examples 1 to 5 that a 1,3 disubstituted cyclopropene containing amino acid, 2 (referred to as 3 in examples 1 to 5 and elsewhere in this document), can be efficiently and site specifically incorporated into proteins using the PylRS/tRNA$_{CUA}$ pair.[25] This amino acid, unlike the 3,3 disubstituted cyclopropene incorporated for photoclickreactions,[26] reacts with tetrazines[19,27] with on-protein rate constants of 27 M$^{-1}$ s$^{-1}$.[25] Here we demonstrate the efficient genetic encoding of a terminal alkyne containing amino acid 1 and a cyclopropene containing amino acid 2 into a single protein and their rapid, quantitative, one-pot labeling with azide and tetrazine probes (FIG. 11). This work provides the first approach to the concerted double labeling of proteins in a one-pot process under aqueous conditions, at physiological pH, and provides a step change in the speed of double labeling, from days in previous work to 30 minutes in the approach reported here.

Proteins containing either 1 or 2 were overexpressed to examine the specificity of the orthogonality of the proposed labeling reactions. A fusion protein of glutathione-S-transferase and calmodulin (GST-CaM) with amino acid 1 at position 1 in calmodulin was expressed from cells containing ribo-Q1 (an evolved orthogonal ribosome[6,28,29]), O-gst-cam$_{1TAG}$ (a fusion gene between glutathione-S-transferase (gst) and calmodulin (cam) on an orthogonal message[30] in which the first codon of cam is replaced with a TAG codon), and MjPrpRS/tRNA$_{CUA}$ (a synthetase/tRNA pair developed for incorporating t in response to the TAG codon)[31] grown in the presence of (4 mM). The GST tag was subsequently removed by cleavage using thrombin at an engineered thrombin-cleavage site between GST and CaM. CaM1$_1$ (CaM containing 1 at position 1, ~100 pmole) was labelled with the azide containing fluorophore 3 (2 nmole), in a Cu (I)-catalysed click reaction. The reaction was quantitative as judged by both the quantitative shift of the fluorescently labelled protein by SDS-PAGE and electrospray ionization mass spectrometry (ESI-MS) (FIG. 11a).

The cyclopropene containing amino acid, 2, was site specifically incorporated at position 40 of calmodulin. The modified protein was expressed in cells bearing the PylRS/tRNA$_{CUA}$ (that efficiently directs the site specific incorporation of 2),[25] ribo-Q1, and O-gst-cam$_{40TAG}$ grown in the presence of 2 (1 mM). CaM2$_{40}$ (~100 pmol) (obtained after thrombin cleavage of the GST tag) was labelled with the tetrazine containing fluorophore 4 (2 nmole). The reaction was quantitative as judged by both the quantitative shift of the fluorescently labelled protein by SDS-PAGE and electrospray ionization mass spectrometry (ESI-MS) (FIG. 11b). CaM2$_{40}$ was not labeled with 3 under the conditions that led to quantitative labeling of CaM1$_1$ with 3 (FIG. 11a). Similarly, CaM1$_1$ was not labeled with 4 under conditions where CaM2$_{40}$ was quantitatively labeled with 4. These experiments demonstrate that the two labeling reagents react quantitatively with their target amino acid, but do not react with their non-targeted unnatural amino acid in proteins.

Next we investigated labeling 1 and 2 within the same protein. We site-specifically incorporated 1 and 2 at positions 1 and 40 of calmodulin to produce CaM1$_1$2$_{40}$ (FIG. 12). We directed the incorporation of amino acid 1 with an MjPrpRS/tRNA$_{CUA}$ pair and the incorporation of amino acid 2 with the evolved PylRS/tRNA$_{UACU}$ pair, which efficiently decodes the quadruplet AGTA codon on orthogonal messages using ribo-Q1.[9] Unnatural amino acids were incorporated in response to UAG and AGTA codons at positions 1 and 40 in calmodulin, within a GST-calmodulin gene on an orthogonal message (O-gst-cam$_{1TAG-40AGTA}$). Expression of full-length GST-CaM1$_1$2$_{40}$ was dependent on the addition of amino acids 1 and 2 to E. coli, and ESI-MS demonstrated the genetically directed incorporation of amino acids 1 and 2 (FIG. 12c). The yield of full length GST-CaM1$_1$2$_{40}$ was ~2 mg per L of culture.

To determine the time required to quantitatively label CaM1$_1$2$_{40}$ with azide 3 or tetrazine 4 we incubated 100 pmol of CaM1$_1$2$_{40}$ with 2 nmol of either 3 or 4 and followed each reaction by both mobility shift on SDS-PAGE and fluorescent imaging upon labeling (FIG. 12b). These experiments demonstrate that fluorophore labeling is complete in 30 minutes.

Next we investigated the labeling of CaM1$_1$2$_{40}$ with both 3 and 4 (FIG. 13). We first tested the addition of 4 (2 nmol) to CaM1$_1$2$_{40}$ (100 pmol) followed by purification to remove free 4, and subsequent labelling with 3 (2 nmol) (FIG. 13a lane 4). This led to efficient double labelling as judged by SDS-PAGE mobility shift and fluorescence imaging. Next we performed sequential labeling without purification by incubating CaM1$_1$2$_{40}$ with 4 for 30 minutes and then adding 3 and click reagents and incubating further for 30 min (FIG. 13a lane 5). This also led to efficient double labelling as judged by SDS-PAGE mobility shift and fluorescence imaging. Finally, we simultaneously added 4 (2 nmol), 3 (2 nmol) and click reagents to CaM1$_1$2$_{40}$ (100 pmol) and incubated for 30 minutes. (FIG. 13a lane 6). This again led to efficient double labelling as judged by SDS-PAGE mobility shift and fluorescence imaging. In all doubly labeled proteins we observe a decrease in the BODIPY-FL fluorescence relative to the singly labeled control upon excitation at 688 nm (compare lanes 4, 5, and 6 to lane 3 in FIG. 13a), consistent with in gel Förster resonance energy transfer (FRET) to between BODIPY-FL and BODIPY-TMR-X. ESI-MS further demonstrates that this concerted, one-pot protocol leads to genetically directed efficient, rapid and quantitative double labeling of proteins.

In summary, in this example we show an efficient and rapid protocol for expressing recombinant proteins bearing a site specifically incorporated alkyne and a site specifically incorporated cyclopropene. We demonstrate that the inverse electron demand Diels Alder reaction of an encoded 1,3 disubstituted cyclopropene and tetrazine probe, and the 3+2 cycloaddition reaction of the encoded alkyne and azide probe are mutually orthogonal to each other and to the functional groups in proteins. By combining the genetic encoding of an alkyne and a cyclopropene in a single protein and labelling with the mutually orthogonal reactions we demonstrate the concerted, one-pot rapid double labeling of a protein in aqueous media at physiological pH and temperature. This strategy has utility for doubly labeling proteins for a variety of studies and applications, and may be extended to the double labeling of diverse molecules in diverse cells and organisms.

Note on example 6: The chemical designations in example 6 and in the corresponding figures (drawings) discussed in example 6 are self-contained and apply only to example 6. Discussion of chemical designations in the rest of this document are consistent with the exception of example 6. For example, the skilled reader will immediately appreciate that compound 2 of example 6 corresponds to compound 3 in the rest of this document (i.e. the exemplary cyclopropene amino acid of the invention). Compounds 3 and 4 of example 6 are tetrazine compounds.

REFERENCES TO EXAMPLE 6

(1) Zhang, J.; Campbell, R. E.; Ting, A. Y.; Tsien, R. Y. *Nature Reviews Molecular Cell Biology* 2002, 3, 906.
(2) Kajihara, D.; Abe, R.; Iijima, I.; Komiyama, C.; Sisido, M.; Hohsaka, T. *Nat Methods* 2006, 3, 923.
(3) Brustad, E. M.; Lemke, E. A.; Schultz, P. G.; Deniz, A. A. *J Am Chem Soc* 2008, 130, 17664.
(4) Nguyen, D. P.; Elliott, T.; Holt, M.; Muir, T. W.; Chin, J. W. *J Am Chem Soc* 2011, 133, 11418.
(5) Wissner, R. F.; Batjargal, S.; Fadzen, C. M.; Petersson, E. J. *J Am Chem Soc* 2013, 135, 6529.
(6) Neumann, H.; Wang, K.; Davis, L.; Garcia-Alai, M.; Chin, J. W. *Nature* 2010, 464, 441.
(7) Wan, W.; Huang, Y.; Wang, Z.; Russell, W. K.; Pai, P. J.; Russell, D. H.; Liu, W. R. Angew *Chem Int Ed Engl* 2010, 49, 3211.
(8) Chatterjee, A.; Sun, S. B.; Furman, J. L.; Xiao, H.; Schultz, P. G. *Biochemistry* 2013.
(9) Wang, K; Sachdeva, A.; Cox, D. J.; Wilt N. W.; Wallace, S.; Mehl, R. A.; Chin, J. W. submitted.
(10) Wu, B.; Wang, Z.; Huang, Y.; Liu, W. R. Chembiochem: *a European journal of chemical biology* 2012, 13, 1405.
(11) Sasmal, P. K.; Carregal-Romero, S.; Han, A. A.; Streu, C. N.; Lin, Z.; Namikawa, K.; Elliott, S. L.; Koster, R. W.; Parak, W. J.; Meggers, E. *ChemBioChem* 2012, 13, 1116.
(12) Rotenberg, S. A.; Calogeropoulou, T.; Jaworski, J. S.; Weinstein, I. B.; Rideout, D. *Proceedings of the National Academy of Sciences of the United States of America* 1991, 88, 2490.
(13) Seitchik, J. L.; Peeler, J. C.; Taylor, M. T.; Blackman, M. L.; Rhoads, T. W.; Cooley, R. B.; Refakis, C.; Fox, J. M.; Mehl, R. A. *J Am Chem Soc* 2012, 134, 2898.
(14) Lang, K.; Davis, L.; Torres-Kolbus, J.; Chou, C.; Deiters, A.; Chin, J. W. *Nat Chem* 2012, 4, 298.
(15) Plass, T.; Mulles, S.; Koehler, C.; Szymański, J.; Mueller, R.; Wießler, M.; Schultz, C.; Lemke, E. A. *Angewandte Chemie International Edition* 2012, 51, 4166.
(16) Kaya, E.; Vrabel, M.; Deiml, C.; Prill, S.; Fluxa, V. S.; Carell, T. *Angewandte Chemie International Edition* 2012, 51, 4466.
(17) Wang, Q.; Chan, T. R.; Hilgraf, R.; Fokin, V. V.; Sharpless, K. B.; Finn, M. G. *J Am Chem Soc* 2003, 125, 3192.
(18) Devaraj, N. K.; Weissleder, R. *Accounts of Chemical Research* 2011, 44, 816.
(19) Yang, J.; Šečkutė, J.; Cole, C. M.; Devaraj, N. K. *Angewandte Chemie International Edition* 2012, 151, 7476.
(20) Blackman, M. L.; Royzen, M.; Fox, J. M. *J Am Chem Soc* 2008, 130, 13518.
(21) Lang, K.; Davis, L.; Wallace, S.; Mahesh, M.; Cox, D. J.; Blackman, M. L.; Fox, J. M.; Chin, J W. *J Am Chem Soc* 2012, 134, 10317.
(22) Borrmann, A.; Milks, S.; Plass, T.; Dommerholt, J.; Verkade, J. M. M.; Wießler, M.; Schultz, C.; van Hest, J. C. M.; van Delft, F. L.; Lemke, E. A. *ChemBioChem* 2012, 13, 2094.
(23) Schoch, J.; Staudt, M.; Samanta, A.; Wiessler, M.; Jaschke, A. *Bioconjug Chem* 2012, 23, 1382.
(24) Karver, M. R.; Weissleder, R.; Hilderbrand, S. A. *Angew Chem Int Ed Engl* 2012, 51, 920.
(25) Bianco, A.; Elliott, T. S.; Townsley, F. M.; Pisa, R.; Davis, L.; Elsässer, S. J.; Ernst, R. J.; Lang, K.; Sachdeva, A.; Chin, J. W. *Under Review.*
(26) Yu, Z.; Pan, Y.; Wang, Z.; Wang, J.; Lin, Q. *Angewandte Chemie International Edition* 2012, 51, 10600.
(27) Kamber, D. N.; Nazarova, L. A.; Liang, Y.; Lopez, S. A.; Patterson, D. M.; Shih, H. W.; Houk, K. N.; Prescher, J. A. *J Am Chem Soc* 2013, 135, 13680.
(28) Wang, K.; Schmied, W. H.; Chin, J. W. *Angew Chem Int Ed Engl* 2012, 51, 2288.
(29) Wang, K.; Neumann, H.; Peak-Chew, S. Y.; Chin, J. W. *Nature biotechnology* 2007, 25, 770.
(30) Rackham, O.; Chin, J. W. *Nature chemical biology* 2005, 1159.
(31) Deiters, A.; Schultz, P. G. *Bioorganic & Medicinal Chemistry Letters* 2005, 15, 1521.

What is claimed is:

1. A polypeptide comprising an amino acid having a cyclopropene group wherein said cyclopropene group is linked to the amino acid via a carbamate group and the carbamate group does not form a part of the polypeptide backbone, wherein said cyclopropene group is a 1,3-disubstituted cyclopropene.

2. A polypeptide according to claim 1 wherein said cyclopropene is a 1,3-dimethylcyclopropene.

3. A polypeptide according to claim 1 wherein said cyclopropene group is present as a residue of a lysine amino acid.

4. A polypeptide according to claim 1 further comprising a tetrazine compound linked to said cyclopropene group.

5. An amino acid comprising cyclopropene wherein said cyclopropene group is linked to the amino acid moiety via a carbamate group and the carbamate group does not form a part of the peptide backbone, wherein said cyclopropene group is a 1,3-disubstituted cyclopropene.

6. An amino acid according to claim 5 wherein said cyclopropene is a 1,3-dimethylcyclopropene.

7. An amino acid according to claim 5 wherein said amino acid is a lysine amino acid.

8. An amino acid according to claim 7 which comprises N$^\varepsilon$-[((2-methylcycloprop-2-en-1-yl)methoxy)carbonyl]-1-lysine.

9. An amino acid according to claim 7 which consists of

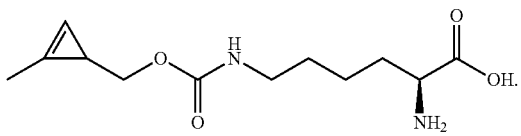 [SMILES: CC1=CC1COC(=O)NCCCC[C@H](N)C(=O)O]

10. A method of producing a polypeptide comprising a cyclopropene group wherein said cyclopropene group is joined to an amino acid moiety of the polypeptide via a carbamate group, said method comprising genetically incorporating said amino acid comprising said cyclopropene group joined to said amino acid moiety via said carbamate group, into said polypeptide.

11. A method according to claim 10 wherein producing the polypeptide comprises
(i) providing a nucleic acid encoding the polypeptide which nucleic acid comprises an orthogonal codon encoding the amino acid having a cyclopropene group;
(ii) translating said nucleic acid in the presence of an orthogonal tRNA synthetase/tRNA pair capable of recognising said orthogonal codon and incorporating said amino acid having a cyclopropene group into the polypeptide chain.

12. A method according to claim 10 wherein said orthogonal codon comprises an amber codon (TAG), said tRNA comprises MbtRNA$_{CUA}$ and said tRNA synthetase comprises MbPylRS; or wherein said orthogonal codon comprises an amber codon (TAG), said tRNA comprises MmtRNA$_{CUA}$ and said tRNA synthetase comprises MmPylRS.

13. A method according to claim 10 wherein said carbamate group does not form a part of the peptide backbone, and wherein said cyclopropene group is a 1,3-disubstituted cyclopropene.

14. A method of producing a polypeptide comprising a tetrazine group, said method comprising providing a polypeptide according to claim 1, contacting said polypeptide with a tetrazine compound, and incubating to allow joining of the tetrazine to a cyclopropene group of the polypeptide by an inverse electron demand Diels-Alder cycloaddition reaction.

15. A method according to claim 14 wherein said reaction is allowed to proceed for 10 minutes or less, preferably for 1 minute or less, preferably for 30 seconds or less.

16. A polypeptide according to claim 1 wherein said polypeptide comprises two or more amino acids each having a cyclopropene group, wherein each said cyclopropene group is linked to each said amino acid via a carbamate group and wherein each carbamate group does not form a part of the polypeptide backbone.

17. A polypeptide according to claim 16 wherein said polypeptide comprises four amino acids each having a cyclopropene group.

18. An antibody drug conjugate (ADC) comprising a polypeptide according to claim 1.

* * * * *

SEQUENCE LISTING

<160> NUMBER OF SEQ ID NOS: 47

<210> SEQ ID NO 1
<211> LENGTH: 419
<212> TYPE: PRT
<213> ORGANISM: Methanosarcina barkeri

<400> SEQUENCE: 1

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Ala Pro Lys Val Lys Lys Ala Met Pro Lys Ser Val Ser
                100                 105                 110

Arg Ala Pro Lys Pro Leu Glu Asn Pro Val Ser Ala Lys Ala Ser Thr
            115                 120                 125

Asp Thr Ser Arg Ser Val Pro Ser Pro Ala Lys Ser Thr Pro Asn Ser
        130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
                180                 185                 190

Lys Asn Asp Phe Gln Arg Leu Tyr Thr Asn Asp Arg Glu Asp Tyr Leu
            195                 200                 205

Gly Lys Leu Glu Arg Asp Ile Thr Lys Phe Phe Val Asp Arg Asp Phe
210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Asp Pro Ile Lys Ile Phe
        275                 280                 285

Glu Val Gly Pro Cys Tyr Arg Lys Glu Ser Asp Gly Lys Glu His Leu
        290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Pro Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415
```

Thr Asn Leu

<210> SEQ ID NO 2
<211> LENGTH: 419
<212> TYPE: PRT
<213> ORGANISM: Methanosarcina barkeri MS

<400> SEQUENCE: 2

| Met | Asp | Lys | Lys | Pro | Leu | Asp | Val | Leu | Ile | Ser | Ala | Thr | Gly | Leu | Trp |
|---|---|---|---|---|---|---|---|---|---|---|---|---|---|---|---|
| 1 | | | | 5 | | | | | 10 | | | | | 15 | |

| Met | Ser | Arg | Thr | Gly | Thr | Leu | His | Lys | Ile | Lys | His | His | Glu | Val | Ser |
|---|---|---|---|---|---|---|---|---|---|---|---|---|---|---|---|
| | | | 20 | | | | | 25 | | | | | 30 | | |

| Arg | Ser | Lys | Ile | Tyr | Ile | Glu | Met | Ala | Cys | Gly | Asp | His | Leu | Val | Val |
|---|---|---|---|---|---|---|---|---|---|---|---|---|---|---|---|
| | | 35 | | | | | 40 | | | | | 45 | | | |

| Asn | Asn | Ser | Arg | Ser | Cys | Arg | Thr | Ala | Arg | Ala | Phe | Arg | His | His | Lys |
|---|---|---|---|---|---|---|---|---|---|---|---|---|---|---|---|
| | 50 | | | | | 55 | | | | | 60 | | | | |

| Tyr | Arg | Lys | Thr | Cys | Lys | Arg | Cys | Arg | Val | Ser | Asp | Glu | Asp | Ile | Asn |
|---|---|---|---|---|---|---|---|---|---|---|---|---|---|---|---|
| 65 | | | | | 70 | | | | | 75 | | | | | 80 |

| Asn | Phe | Leu | Thr | Arg | Ser | Thr | Glu | Ser | Lys | Asn | Ser | Val | Lys | Val | Arg |
|---|---|---|---|---|---|---|---|---|---|---|---|---|---|---|---|
| | | | | 85 | | | | | 90 | | | | | 95 | |

| Val | Val | Ser | Ala | Pro | Lys | Val | Lys | Lys | Ala | Met | Pro | Lys | Ser | Val | Ser |
|---|---|---|---|---|---|---|---|---|---|---|---|---|---|---|---|
| | | | 100 | | | | | 105 | | | | | 110 | | |

| Arg | Ala | Pro | Lys | Pro | Leu | Glu | Asn | Ser | Val | Ser | Ala | Lys | Ala | Ser | Thr |
|---|---|---|---|---|---|---|---|---|---|---|---|---|---|---|---|
| | | 115 | | | | | 120 | | | | | 125 | | | |

| Asn | Thr | Ser | Arg | Ser | Val | Pro | Ser | Pro | Ala | Lys | Ser | Thr | Pro | Asn | Ser |
|---|---|---|---|---|---|---|---|---|---|---|---|---|---|---|---|
| | 130 | | | | | 135 | | | | | 140 | | | | |

| Ser | Val | Pro | Ala | Ser | Ala | Pro | Ala | Pro | Ser | Leu | Thr | Arg | Ser | Gln | Leu |
|---|---|---|---|---|---|---|---|---|---|---|---|---|---|---|---|
| 145 | | | | | 150 | | | | | 155 | | | | | 160 |

| Asp | Arg | Val | Glu | Ala | Leu | Leu | Ser | Pro | Glu | Asp | Lys | Ile | Ser | Leu | Asn |
|---|---|---|---|---|---|---|---|---|---|---|---|---|---|---|---|
| | | | | 165 | | | | | 170 | | | | | 175 | |

| Met | Ala | Lys | Pro | Phe | Arg | Glu | Leu | Glu | Pro | Glu | Leu | Val | Thr | Arg | Arg |
|---|---|---|---|---|---|---|---|---|---|---|---|---|---|---|---|
| | | | 180 | | | | | 185 | | | | | 190 | | |

| Lys | Asn | Asp | Phe | Gln | Arg | Leu | Tyr | Thr | Asn | Asp | Arg | Glu | Asp | Tyr | Leu |
|---|---|---|---|---|---|---|---|---|---|---|---|---|---|---|---|
| | | 195 | | | | | 200 | | | | | 205 | | | |

| Gly | Lys | Leu | Glu | Arg | Asp | Ile | Thr | Lys | Phe | Phe | Val | Asp | Arg | Gly | Phe |
|---|---|---|---|---|---|---|---|---|---|---|---|---|---|---|---|
| | 210 | | | | | 215 | | | | | 220 | | | | |

| Leu | Glu | Ile | Lys | Ser | Pro | Ile | Leu | Ile | Pro | Ala | Glu | Tyr | Val | Glu | Arg |
|---|---|---|---|---|---|---|---|---|---|---|---|---|---|---|---|
| 225 | | | | | 230 | | | | | 235 | | | | | 240 |

| Met | Gly | Ile | Asn | Asn | Asp | Thr | Glu | Leu | Ser | Lys | Gln | Ile | Phe | Arg | Val |
|---|---|---|---|---|---|---|---|---|---|---|---|---|---|---|---|
| | | | | 245 | | | | | 250 | | | | | 255 | |

| Asp | Lys | Asn | Leu | Cys | Leu | Arg | Pro | Met | Leu | Ala | Pro | Thr | Leu | Tyr | Asn |
|---|---|---|---|---|---|---|---|---|---|---|---|---|---|---|---|
| | | | 260 | | | | | 265 | | | | | 270 | | |

| Tyr | Leu | Arg | Lys | Leu | Asp | Arg | Ile | Leu | Pro | Gly | Pro | Ile | Lys | Ile | Phe |
|---|---|---|---|---|---|---|---|---|---|---|---|---|---|---|---|
| | | 275 | | | | | 280 | | | | | 285 | | | |

| Glu | Val | Gly | Pro | Cys | Tyr | Arg | Lys | Glu | Ser | Asp | Gly | Lys | Glu | His | Leu |
|---|---|---|---|---|---|---|---|---|---|---|---|---|---|---|---|
| | 290 | | | | | 295 | | | | | 300 | | | | |

| Glu | Glu | Phe | Thr | Met | Val | Asn | Phe | Cys | Gln | Met | Gly | Ser | Gly | Cys | Thr |
|---|---|---|---|---|---|---|---|---|---|---|---|---|---|---|---|
| 305 | | | | | 310 | | | | | 315 | | | | | 320 |

| Arg | Glu | Asn | Leu | Glu | Ala | Leu | Ile | Lys | Glu | Phe | Leu | Asp | Tyr | Leu | Glu |
|---|---|---|---|---|---|---|---|---|---|---|---|---|---|---|---|
| | | | | 325 | | | | | 330 | | | | | 335 | |

| Ile | Asp | Phe | Glu | Ile | Val | Gly | Asp | Ser | Cys | Met | Val | Tyr | Gly | Asp | Thr |
|---|---|---|---|---|---|---|---|---|---|---|---|---|---|---|---|
| | | | 340 | | | | | 345 | | | | | 350 | | |

| Leu | Asp | Ile | Met | His | Gly | Asp | Leu | Glu | Leu | Ser | Ser | Ala | Val | Val | Gly |
|---|---|---|---|---|---|---|---|---|---|---|---|---|---|---|---|
| | | 355 | | | | | 360 | | | | | 365 | | | |

```
Pro Val Ser Leu Asp Arg Glu Trp Gly Ile Asp Lys Pro Trp Ile Gly
370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 3
<211> LENGTH: 419
<212> TYPE: PRT
<213> ORGANISM: Methanosarcina barkeri str. Fusaro

<400> SEQUENCE: 3

Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
                20                  25                  30

Arg Ser Lys Ile Tyr Ile Glu Met Ala Cys Gly Asp His Leu Val Val
                35                  40                  45

Asn Asn Ser Arg Ser Cys Arg Thr Ala Arg Ala Phe Arg His His Lys
50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Ala Pro Lys Val Lys Lys Ala Met Pro Lys Ser Val Ser
                100                 105                 110

Arg Ala Pro Lys Pro Leu Glu Asn Pro Val Ser Ala Lys Ala Ser Thr
                115                 120                 125

Asp Thr Ser Arg Ser Val Pro Ser Pro Ala Lys Ser Thr Pro Asn Ser
130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
                180                 185                 190

Lys Asn Asp Phe Gln Arg Leu Tyr Thr Asn Asp Arg Glu Asp Tyr Leu
                195                 200                 205

Gly Lys Leu Glu Arg Asp Ile Thr Lys Phe Phe Val Asp Arg Asp Phe
210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
                260                 265                 270

Tyr Leu Arg Lys Leu Asp Arg Ile Leu Pro Asp Pro Ile Lys Ile Phe
                275                 280                 285

Glu Val Gly Pro Cys Tyr Arg Lys Glu Ser Asp Gly Lys Glu His Leu
                290                 295                 300

Glu Glu Phe Thr Met Val Asn Phe Cys Gln Met Gly Ser Gly Cys Thr
305                 310                 315                 320
```

-continued

```
Arg Glu Asn Leu Glu Ser Leu Ile Lys Glu Phe Leu Asp Tyr Leu Glu
            325                 330                 335

Ile Asp Phe Glu Ile Val Gly Asp Ser Cys Met Val Tyr Gly Asp Thr
        340                 345                 350

Leu Asp Ile Met His Gly Asp Leu Glu Leu Ser Ser Ala Val Val Gly
            355                 360                 365

Pro Val Pro Leu Asp Arg Glu Trp Gly Ile Asp Lys Pro Trp Ile Gly
        370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 4
<211> LENGTH: 454
<212> TYPE: PRT
<213> ORGANISM: Methanosarcina mazei Go1

<400> SEQUENCE: 4

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270
```

-continued

```
Ile Glu Arg Met Gly Ile Asp Asn Asp Thr Glu Leu Ser Lys Gln Ile
            275                 280                 285

Phe Arg Val Asp Lys Asn Phe Cys Leu Arg Pro Met Leu Ala Pro Asn
        290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450
```

<210> SEQ ID NO 5
<211> LENGTH: 443
<212> TYPE: PRT
<213> ORGANISM: Methanosarcina acetivorans C2A

<400> SEQUENCE: 5

```
Met Asp Lys Lys Pro Leu Asp Thr Leu Ile Ser Ala Thr Gly Leu Trp
1               5                   10                  15

Met Ser Arg Thr Gly Met Ile His Lys Ile Lys His Glu Val Ser
            20                  25                  30

Arg Ser Lys Ile Tyr Ile Glu Met Ala Cys Gly Glu Arg Leu Val Val
        35                  40                  45

Asn Asn Ser Arg Ser Ser Arg Thr Ala Arg Ala Leu Arg His His Lys
    50                  55                  60

Tyr Arg Lys Thr Cys Arg His Cys Arg Val Ser Asp Glu Asp Ile Asn
65                  70                  75                  80

Asn Phe Leu Thr Lys Thr Ser Glu Glu Lys Thr Thr Val Lys Val Lys
                85                  90                  95

Val Val Ser Ala Pro Arg Val Arg Lys Ala Met Pro Lys Ser Val Ala
            100                 105                 110

Arg Ala Pro Lys Pro Leu Glu Ala Thr Ala Gln Val Pro Leu Ser Gly
        115                 120                 125

Ser Lys Pro Ala Pro Ala Thr Pro Val Ser Ala Pro Ala Gln Ala Pro
    130                 135                 140

Ala Pro Ser Thr Gly Ser Ala Ser Ala Thr Ser Ala Ser Ala Gln Arg
145                 150                 155                 160

Met Ala Asn Ser Ala Ala Ala Pro Ala Pro Val Pro Thr Ser Ala
                165                 170                 175

Pro Ala Leu Thr Lys Gly Gln Leu Asp Arg Leu Glu Gly Leu Leu Ser
            180                 185                 190
```

Pro Lys Asp Glu Ile Ser Leu Asp Ser Glu Lys Pro Phe Arg Glu Leu
            195                 200                 205

Glu Ser Glu Leu Leu Ser Arg Arg Lys Lys Asp Leu Lys Arg Ile Tyr
210                 215                 220

Ala Glu Arg Glu Asn Tyr Leu Gly Lys Leu Glu Arg Glu Ile Thr
225                 230                 235                 240

Lys Phe Phe Val Asp Arg Gly Phe Leu Glu Ile Lys Ser Pro Ile Leu
            245                 250                 255

Ile Pro Ala Glu Tyr Val Glu Arg Met Gly Ile Asn Ser Asp Thr Glu
            260                 265                 270

Leu Ser Lys Gln Val Phe Arg Ile Asp Lys Asn Phe Cys Leu Arg Pro
            275                 280                 285

Met Leu Ala Pro Asn Leu Tyr Asn Tyr Leu Arg Lys Leu Asp Arg Ala
290                 295                 300

Leu Pro Asp Pro Ile Lys Ile Phe Glu Ile Gly Pro Cys Tyr Arg Lys
305                 310                 315                 320

Glu Ser Asp Gly Lys Glu His Leu Glu Glu Phe Thr Met Leu Asn Phe
            325                 330                 335

Cys Gln Met Gly Ser Gly Cys Thr Arg Glu Asn Leu Glu Ala Ile Ile
            340                 345                 350

Thr Glu Phe Leu Asn His Leu Gly Ile Asp Phe Glu Ile Ile Gly Asp
            355                 360                 365

Ser Cys Met Val Tyr Gly Asn Thr Leu Asp Val Met His Asp Asp Leu
            370                 375                 380

Glu Leu Ser Ser Ala Val Val Gly Pro Val Pro Leu Asp Arg Glu Trp
385                 390                 395                 400

Gly Ile Asp Lys Pro Trp Ile Gly Ala Gly Phe Gly Leu Glu Arg Leu
            405                 410                 415

Leu Lys Val Met His Gly Phe Lys Asn Ile Lys Arg Ala Ala Arg Ser
            420                 425                 430

Glu Ser Tyr Tyr Asn Gly Ile Ser Thr Asn Leu
            435                 440

<210> SEQ ID NO 6
<211> LENGTH: 478
<212> TYPE: PRT
<213> ORGANISM: Methanosarcina thermophila

<400> SEQUENCE: 6

Met Asp Lys Lys Pro Leu Asn Thr Leu Ile Ser Ala Thr Gly Leu Trp
1               5                   10                  15

Met Ser Arg Thr Gly Lys Leu His Lys Ile Arg His His Glu Val Ser
            20                  25                  30

Lys Arg Lys Ile Tyr Ile Glu Met Glu Cys Gly Glu Arg Leu Val Val
        35                  40                  45

Asn Asn Ser Arg Ser Cys Arg Ala Ala Arg Ala Leu Arg His His Lys
    50                  55                  60

Tyr Arg Lys Ile Cys Lys His Cys Arg Val Ser Asp Glu Asp Leu Asn
65                  70                  75                  80

Lys Phe Leu Thr Arg Thr Asn Glu Asp Lys Ser Asn Ala Lys Val Thr
                85                  90                  95

Val Val Ser Ala Pro Lys Ile Arg Lys Val Met Pro Lys Ser Val Ala
            100                 105                 110

Arg Thr Pro Lys Pro Leu Glu Asn Thr Ala Pro Val Gln Thr Leu Pro

```
            115                 120                 125
Ser Glu Ser Gln Pro Ala Pro Thr Thr Pro Ile Ser Ala Ser Thr Thr
    130                 135                 140

Ala Pro Ala Ser Thr Ser Thr Thr Ala Pro Ala Pro Ala Ser Thr Thr
145                 150                 155                 160

Ala Pro Ala Pro Ala Ser Thr Thr Ala Pro Ala Ser Ala Ser Thr Thr
                165                 170                 175

Ile Ser Thr Ser Ala Met Pro Ala Ser Thr Ser Ala Gln Gly Thr Thr
                180                 185                 190

Lys Phe Asn Tyr Ile Ser Gly Gly Phe Pro Arg Pro Ile Pro Val Gln
                195                 200                 205

Ala Ser Ala Pro Ala Leu Thr Lys Ser Gln Ile Asp Arg Leu Gln Gly
        210                 215                 220

Leu Leu Ser Pro Lys Asp Glu Ile Ser Leu Asp Ser Gly Thr Pro Phe
225                 230                 235                 240

Arg Lys Leu Glu Ser Glu Leu Leu Ser Arg Arg Lys Asp Leu Lys
                245                 250                 255

Gln Ile Tyr Ala Glu Glu Arg Glu His Tyr Leu Gly Lys Leu Glu Arg
                260                 265                 270

Glu Ile Thr Lys Phe Phe Val Asp Arg Gly Phe Leu Glu Ile Lys Ser
            275                 280                 285

Pro Ile Leu Ile Pro Met Glu Tyr Ile Glu Arg Met Gly Ile Asp Asn
    290                 295                 300

Asp Lys Glu Leu Ser Lys Gln Ile Phe Arg Val Asp Asn Asn Phe Cys
305                 310                 315                 320

Leu Arg Pro Met Leu Ala Pro Asn Leu Tyr Asn Tyr Leu Arg Lys Leu
                325                 330                 335

Asn Arg Ala Leu Pro Asp Pro Ile Lys Ile Phe Glu Ile Gly Pro Cys
                340                 345                 350

Tyr Arg Lys Glu Ser Asp Gly Lys Glu His Leu Glu Glu Phe Thr Met
            355                 360                 365

Leu Asn Phe Cys Gln Met Gly Ser Gly Cys Thr Arg Glu Asn Leu Glu
    370                 375                 380

Ala Ile Ile Lys Asp Phe Leu Asp Tyr Leu Gly Ile Asp Phe Glu Ile
385                 390                 395                 400

Val Gly Asp Ser Cys Met Val Tyr Gly Asp Thr Leu Asp Val Met His
                405                 410                 415

Gly Asp Leu Glu Leu Ser Ser Ala Val Val Gly Pro Val Pro Met Asp
                420                 425                 430

Arg Asp Trp Gly Ile Asn Lys Pro Trp Ile Gly Ala Gly Phe Gly Leu
            435                 440                 445

Glu Arg Leu Leu Lys Val Met His Asn Phe Lys Asn Ile Lys Arg Ala
    450                 455                 460

Ser Arg Ser Glu Ser Tyr Tyr Asn Gly Ile Ser Thr Asn Leu
465                 470                 475

<210> SEQ ID NO 7
<211> LENGTH: 416
<212> TYPE: PRT
<213> ORGANISM: Methanococcoides burtonii DSM 6242

<400> SEQUENCE: 7

Met Glu Lys Gln Leu Leu Asp Val Leu Val Glu Leu Asn Gly Val Trp
1               5                   10                  15
```

Leu Ser Arg Ser Gly Leu Leu His Gly Ile Arg Asn Phe Glu Ile Thr
            20                  25                  30

Thr Lys His Ile His Ile Glu Thr Asp Cys Gly Ala Arg Phe Thr Val
            35                  40                  45

Arg Asn Ser Arg Ser Ser Arg Ser Ala Arg Ser Leu Arg His Asn Lys
 50                  55                  60

Tyr Arg Lys Pro Cys Lys Arg Cys Arg Pro Ala Asp Glu Gln Ile Asp
 65                  70                  75                  80

Arg Phe Val Lys Lys Thr Phe Lys Glu Lys Arg Gln Thr Val Ser Val
             85                  90                  95

Phe Ser Ser Pro Lys Lys His Val Pro Lys Lys Pro Lys Val Ala Val
            100                 105                 110

Ile Lys Ser Phe Ser Ile Ser Thr Pro Ser Pro Lys Glu Ala Ser Val
            115                 120                 125

Ser Asn Ser Ile Pro Thr Pro Ser Ile Ser Val Val Lys Asp Glu Val
            130                 135                 140

Lys Val Pro Glu Val Lys Tyr Thr Pro Ser Gln Ile Glu Arg Leu Lys
145                 150                 155                 160

Thr Leu Met Ser Pro Asp Asp Lys Ile Pro Ile Gln Asp Glu Leu Pro
            165                 170                 175

Glu Phe Lys Val Leu Glu Lys Glu Leu Ile Gln Arg Arg Asp Asp
            180                 185                 190

Leu Lys Lys Met Tyr Glu Glu Asp Arg Glu Asp Arg Leu Gly Lys Leu
            195                 200                 205

Glu Arg Asp Ile Thr Glu Phe Phe Val Asp Arg Gly Phe Leu Glu Ile
210                 215                 220

Lys Ser Pro Ile Met Ile Pro Phe Glu Tyr Ile Glu Arg Met Gly Ile
225                 230                 235                 240

Asp Lys Asp Asp His Leu Asn Lys Gln Ile Phe Arg Val Asp Glu Ser
            245                 250                 255

Met Cys Leu Arg Pro Met Leu Ala Pro Cys Leu Tyr Asn Tyr Leu Arg
            260                 265                 270

Lys Leu Asp Lys Val Leu Pro Asp Pro Ile Arg Ile Phe Glu Ile Gly
            275                 280                 285

Pro Cys Tyr Arg Lys Glu Ser Asp Gly Ser Ser His Leu Glu Glu Phe
            290                 295                 300

Thr Met Val Asn Phe Cys Gln Met Gly Ser Gly Cys Thr Arg Glu Asn
305                 310                 315                 320

Met Glu Ala Leu Ile Asp Glu Phe Leu Glu His Leu Gly Ile Glu Tyr
            325                 330                 335

Glu Ile Glu Ala Asp Asn Cys Met Val Tyr Gly Asp Thr Ile Asp Ile
            340                 345                 350

Met His Gly Asp Leu Glu Leu Ser Ser Ala Val Val Gly Pro Ile Pro
            355                 360                 365

Leu Asp Arg Glu Trp Gly Val Asn Lys Pro Trp Met Gly Ala Gly Phe
            370                 375                 380

Gly Leu Glu Arg Leu Leu Lys Val Arg His Asn Tyr Thr Asn Ile Arg
385                 390                 395                 400

Arg Ala Ser Arg Ser Glu Leu Tyr Tyr Asn Gly Ile Asn Thr Asn Leu
                405                 410                 415

<210> SEQ ID NO 8
<211> LENGTH: 279
<212> TYPE: PRT

<213> ORGANISM: Desulfitobacterium hafniense DCB-2

<400> SEQUENCE: 8

```
Met Ser Ser Phe Trp Thr Lys Val Gln Tyr Gln Arg Leu Lys Glu Leu
1               5                   10                  15

Asn Ala Ser Gly Glu Gln Leu Glu Met Gly Phe Ser Asp Ala Leu Ser
            20                  25                  30

Arg Asp Arg Ala Phe Gln Gly Ile Glu His Gln Leu Met Ser Gln Gly
        35                  40                  45

Lys Arg His Leu Glu Gln Leu Arg Thr Val Lys His Arg Pro Ala Leu
    50                  55                  60

Leu Glu Leu Glu Glu Gly Leu Ala Lys Ala Leu His Gln Gln Gly Phe
65                  70                  75                  80

Val Gln Val Val Thr Pro Thr Ile Ile Thr Lys Ser Ala Leu Ala Lys
                85                  90                  95

Met Thr Ile Gly Glu Asp His Pro Leu Phe Ser Gln Val Phe Trp Leu
            100                 105                 110

Asp Gly Lys Lys Cys Leu Arg Pro Met Leu Ala Pro Asn Leu Tyr Thr
        115                 120                 125

Leu Trp Arg Glu Leu Glu Arg Leu Trp Asp Lys Pro Ile Arg Ile Phe
    130                 135                 140

Glu Ile Gly Thr Cys Tyr Arg Lys Glu Ser Gln Gly Ala Gln His Leu
145                 150                 155                 160

Asn Glu Phe Thr Met Leu Asn Leu Thr Glu Leu Gly Thr Pro Leu Glu
                165                 170                 175

Glu Arg His Gln Arg Leu Glu Asp Met Ala Arg Trp Val Leu Glu Ala
            180                 185                 190

Ala Gly Ile Arg Glu Phe Glu Leu Val Thr Glu Ser Ser Val Val Tyr
        195                 200                 205

Gly Asp Thr Val Asp Val Met Lys Gly Asp Leu Glu Leu Ala Ser Gly
    210                 215                 220

Ala Met Gly Pro His Phe Leu Asp Glu Lys Trp Glu Ile Val Asp Pro
225                 230                 235                 240

Trp Val Gly Leu Gly Phe Gly Leu Glu Arg Leu Leu Met Ile Arg Glu
                245                 250                 255

Gly Thr Gln His Val Gln Ser Met Ala Arg Ser Leu Ser Tyr Leu Asp
            260                 265                 270

Gly Val Arg Leu Asn Ile Asn
        275
```

<210> SEQ ID NO 9
<211> LENGTH: 312
<212> TYPE: PRT
<213> ORGANISM: Desulfitobacterium hafniense Y51

<400> SEQUENCE: 9

```
Met Asp Arg Ile Asp His Thr Asp Ser Lys Phe Val Gln Ala Gly Glu
1               5                   10                  15

Thr Pro Val Leu Pro Ala Thr Phe Met Phe Leu Thr Arg Arg Asp Pro
            20                  25                  30

Pro Leu Ser Ser Phe Trp Thr Lys Val Gln Tyr Gln Arg Leu Lys Glu
        35                  40                  45

Leu Asn Ala Ser Gly Glu Gln Leu Glu Met Gly Phe Ser Asp Ala Leu
    50                  55                  60

Ser Arg Asp Arg Ala Phe Gln Gly Ile Glu His Gln Leu Met Ser Gln
```

```
                65                  70                  75                  80
        Gly Lys Arg His Leu Glu Gln Leu Arg Thr Val Lys His Arg Pro Ala
                            85                  90                  95

Leu Leu Glu Leu Glu Glu Gly Leu Ala Lys Ala Leu His Gln Gln Gly
                        100                 105                 110

Phe Val Gln Val Val Thr Pro Thr Ile Ile Thr Lys Ser Ala Leu Ala
                    115                 120                 125

Lys Met Thr Ile Gly Glu Asp His Pro Leu Phe Ser Gln Val Phe Trp
        130                 135                 140

Leu Asp Gly Lys Lys Cys Leu Arg Pro Met Leu Ala Pro Asn Leu Tyr
        145                 150                 155                 160

Thr Leu Trp Arg Glu Leu Glu Arg Leu Trp Asp Lys Pro Ile Arg Ile
                        165                 170                 175

Phe Glu Ile Gly Thr Cys Tyr Arg Lys Glu Ser Gln Gly Ala Gln His
                    180                 185                 190

Leu Asn Glu Phe Thr Met Leu Asn Leu Thr Glu Leu Gly Thr Pro Leu
                195                 200                 205

Glu Glu Arg His Gln Arg Leu Glu Asp Met Ala Arg Trp Val Leu Glu
            210                 215                 220

Ala Ala Gly Ile Arg Glu Phe Glu Leu Val Thr Glu Ser Ser Val Val
        225                 230                 235                 240

Tyr Gly Asp Thr Val Asp Val Met Lys Gly Asp Leu Glu Leu Ala Ser
                        245                 250                 255

Gly Ala Met Gly Pro His Phe Leu Asp Glu Lys Trp Glu Ile Val Asp
                    260                 265                 270

Pro Trp Val Gly Leu Gly Phe Gly Leu Glu Arg Leu Leu Met Ile Arg
                275                 280                 285

Glu Gly Thr Gln His Val Gln Ser Met Ala Arg Ser Leu Ser Tyr Leu
            290                 295                 300

Asp Gly Val Arg Leu Asn Ile Asn
        305                 310

<210> SEQ ID NO 10
        <211> LENGTH: 288
        <212> TYPE: PRT
        <213> ORGANISM: Desulfitobacterium hafniense

<400> SEQUENCE: 10

Met Phe Leu Thr Arg Arg Asp Pro Pro Leu Ser Ser Phe Trp Thr Lys
        1               5                   10                  15

Val Gln Tyr Gln Arg Leu Lys Glu Leu Asn Ala Ser Gly Glu Gln Leu
                        20                  25                  30

Glu Met Gly Phe Ser Asp Ala Leu Ser Arg Asp Arg Ala Phe Gln Gly
                    35                  40                  45

Ile Glu His Gln Leu Met Ser Gln Gly Lys Arg His Leu Glu Gln Leu
                50                  55                  60

Arg Thr Val Lys His Arg Pro Ala Leu Leu Glu Glu Lys Leu
        65                  70                  75                  80

Ala Lys Ala Leu His Gln Gln Gly Phe Val Gln Val Val Thr Pro Thr
                        85                  90                  95

Ile Ile Thr Lys Ser Ala Leu Ala Lys Met Thr Ile Gly Glu Asp His
                    100                 105                 110

Pro Leu Phe Ser Gln Val Phe Trp Leu Asp Gly Lys Lys Cys Leu Arg
                115                 120                 125
```

```
Pro Met Leu Ala Pro Asn Leu Tyr Thr Leu Trp Arg Glu Leu Glu Arg
            130                 135                 140

Leu Trp Asp Lys Pro Ile Arg Ile Phe Glu Ile Gly Thr Cys Tyr Arg
145                 150                 155                 160

Lys Glu Ser Gln Gly Ala Gln His Leu Asn Glu Phe Thr Met Leu Asn
                165                 170                 175

Leu Thr Glu Leu Gly Thr Pro Leu Glu Glu Arg His Gln Arg Leu Glu
            180                 185                 190

Asp Met Ala Arg Trp Val Leu Glu Ala Ala Gly Ile Arg Glu Phe Glu
                195                 200                 205

Leu Val Thr Glu Ser Ser Val Val Tyr Gly Asp Thr Val Asp Val Met
210                 215                 220

Lys Gly Asp Leu Glu Leu Ala Ser Gly Ala Met Gly Pro His Phe Leu
225                 230                 235                 240

Asp Glu Lys Trp Glu Ile Phe Asp Pro Trp Val Gly Leu Gly Phe Gly
                245                 250                 255

Leu Glu Arg Leu Leu Met Ile Arg Glu Gly Thr Gln His Val Gln Ser
            260                 265                 270

Met Ala Arg Ser Leu Ser Tyr Leu Asp Gly Val Arg Leu Asn Ile Asn
            275                 280                 285

<210> SEQ ID NO 11
<211> LENGTH: 277
<212> TYPE: PRT
<213> ORGANISM: Desulfotomaculum acetoxidans DSM 771

<400> SEQUENCE: 11

Met Ser Phe Leu Trp Thr Val Ser Gln Gln Lys Arg Leu Ser Glu Leu
1               5                   10                  15

Asn Ala Ser Glu Glu Lys Asn Met Ser Phe Ser Ser Thr Ser Ser Asp
                20                  25                  30

Arg Glu Ala Ala Tyr Lys Arg Val Glu Met Arg Leu Ile Asn Glu Ser
            35                  40                  45

Lys Gln Arg Leu Asn Lys Leu Arg His Glu Thr Arg Pro Ala Ile Cys
50                  55                  60

Ala Leu Glu Asn Arg Leu Ala Ala Leu Arg Gly Ala Gly Phe Val
65                  70                  75                  80

Gln Val Ala Thr Pro Val Ile Leu Ser Lys Lys Leu Leu Gly Lys Met
                85                  90                  95

Thr Ile Thr Asp Glu His Ala Leu Phe Ser Gln Val Phe Trp Ile Glu
            100                 105                 110

Glu Asn Lys Cys Leu Arg Pro Met Leu Ala Pro Asn Leu Tyr Tyr Ile
            115                 120                 125

Leu Lys Asp Leu Leu Arg Leu Trp Glu Lys Pro Val Arg Ile Phe Glu
            130                 135                 140

Ile Gly Ser Cys Phe Arg Lys Glu Ser Gln Gly Ser Asn His Leu Asn
145                 150                 155                 160

Glu Phe Thr Met Leu Asn Leu Val Glu Trp Gly Leu Pro Glu Glu Gln
                165                 170                 175

Arg Gln Lys Arg Ile Ser Glu Leu Ala Lys Leu Val Met Asp Glu Thr
            180                 185                 190

Gly Ile Asp Glu Tyr His Leu Glu His Ala Glu Ser Val Val Tyr Gly
            195                 200                 205

Glu Thr Val Asp Val Met His Arg Asp Ile Glu Leu Gly Ser Gly Ala
210                 215                 220
```

```
Leu Gly Pro His Phe Leu Asp Gly Arg Trp Val Gly Pro Trp
225                 230                 235                 240

Val Gly Ile Gly Phe Gly Leu Glu Arg Leu Met Val Glu Gln Gly
                245                 250                 255

Gly Gln Asn Val Arg Ser Met Gly Lys Ser Leu Thr Tyr Leu Asp Gly
            260                 265                 270

Val Arg Leu Asn Ile
            275

<210> SEQ ID NO 12
<211> LENGTH: 419
<212> TYPE: PRT
<213> ORGANISM: Methanosarcina barkeri

<400> SEQUENCE: 12

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
```

```
                305                 310                 315                 320
Arg Glu Asn Leu Glu Ala Leu Ile Lys Glu Phe Leu Asp Tyr Leu Glu
                    325                 330                 335

Ile Asp Phe Glu Ile Val Gly Asp Ser Cys Met Val Tyr Gly Asp Thr
                340                 345                 350

Leu Asp Ile Met His Gly Asp Leu Glu Leu Ser Ser Ala Val Val Gly
                355                 360                 365

Pro Val Ser Leu Asp Arg Glu Trp Gly Ile Asp Lys Pro Trp Ile Gly
            370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                    405                 410                 415

Thr Asn Leu

<210> SEQ ID NO 13
<211> LENGTH: 419
<212> TYPE: PRT
<213> ORGANISM: Methanosarcina barkeri

<400> SEQUENCE: 13

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Gly Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
                100                 105                 110

Arg Ala Pro Lys Pro Leu Glu Asn Ser Val Ser Ala Lys Ala Ser Thr
            115                 120                 125

Asn Thr Ser Arg Ser Val Pro Ser Pro Ala Lys Ser Thr Pro Asn Ser
        130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Val Ala Pro Thr Ile Phe Asn
```

```
                260                 265                 270
Tyr Ala Arg Lys Leu Asp Arg Ile Leu Pro Gly Pro Ile Lys Ile Phe
            275                 280                 285

Glu Val Gly Pro Cys Tyr Arg Lys Glu Ser Asp Gly Lys Glu His Leu
        290                 295                 300

Glu Glu Phe Thr Met Val Asn Phe Phe Gln Met Gly Ser Gly Cys Thr
305                 310                 315                 320

Arg Glu Asn Leu Glu Ala Leu Ile Lys Glu Phe Leu Asp Tyr Leu Glu
            325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
            355                 360                 365

Pro Val Ser Leu Asp Arg Glu Trp Gly Ile Asp Lys Pro Trp Ile Gly
        370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
            405                 410                 415

Thr Asn Leu
```

<210> SEQ ID NO 14
<211> LENGTH: 419
<212> TYPE: PRT
<213> ORGANISM: Methanosarcina barkeri

<400> SEQUENCE: 14

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
            85                  90                  95

Val Val Ser Ala Pro Lys Val Lys Lys Ala Met Pro Lys Ser Val Ser
        100                 105                 110

Arg Ala Pro Lys Pro Leu Glu Asn Ser Val Ser Ala Lys Ala Ser Thr
    115                 120                 125

Asn Thr Ser Arg Ser Val Pro Ser Pro Ala Lys Ser Thr Pro Asn Ser
130                 135                 140

Ser Val Pro Ala Ser Ala Pro Pro Ser Leu Thr Arg Ser Gln Leu
145                 150                 155                 160

Asp Arg Val Glu Ala Leu Leu Ser Pro Glu Asp Lys Ile Ser Leu Asn
            165                 170                 175

Met Ala Lys Pro Phe Arg Glu Leu Glu Pro Glu Leu Val Thr Arg Arg
        180                 185                 190

Lys Asn Asp Phe Gln Arg Leu Tyr Thr Asn Asp Arg Glu Asp Tyr Leu
    195                 200                 205

Gly Lys Leu Glu Arg Asp Ile Thr Lys Phe Phe Val Asp Arg Gly Phe
```

```
                  210                 215                 220
Leu Glu Ile Lys Ser Pro Ile Leu Ile Pro Ala Glu Tyr Val Glu Arg
225                 230                 235                 240

Phe Gly Ile Asn Asn Asp Thr Glu Leu Ser Lys Gln Ile Phe Arg Val
                245                 250                 255

Asp Lys Asn Leu Cys Leu Arg Pro Met Leu Ser Pro Thr Leu Cys Asn
            260                 265                 270

Tyr Met Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 15
<211> LENGTH: 454
<212> TYPE: PRT
<213> ORGANISM: Methanosarcina mazei

<400> SEQUENCE: 15

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
```

```
                165                 170                 175
Thr Ser Met Ser Ala Pro Val Gln Ala Ser Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
                260                 265                 270

Ile Glu Arg Met Gly Ile Asp Asn Asp Thr Glu Leu Ser Lys Gln Ile
                275                 280                 285

Phe Arg Val Asp Lys Asn Phe Cys Leu Arg Pro Met Leu Ala Pro Asn
            290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
                420                 425                 430

Asp Phe Lys Asn Ile Lys Arg Ala Ala Arg Ser Glu Ser Tyr Tyr Asn
            435                 440                 445

Gly Ile Ser Thr Asn Leu
        450

<210> SEQ ID NO 16
<211> LENGTH: 454
<212> TYPE: PRT
<213> ORGANISM: Methanosarcina mazei

<400> SEQUENCE: 16

Met Asp Lys Lys Pro Leu Asn Thr Leu Ile Ser Ala Thr Gly Leu Trp
1               5                  10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80
```

```
Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Val Ala Pro Asn
    290                 295                 300

Ile Phe Asn Tyr Ala Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Phe Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 17
<211> LENGTH: 454
<212> TYPE: PRT
<213> ORGANISM: Methanosarcina mazei

<400> SEQUENCE: 17
```

-continued

```
Met Asp Lys Lys Pro Leu Asn Thr Leu Ile Ser Ala Thr Gly Leu Trp
 1               5                  10                 15

Met Ser Arg Thr Gly Thr Ile His Lys Ile Lys His His Glu Val Ser
             20                  25                 30

Arg Ser Lys Ile Tyr Ile Glu Met Ala Cys Gly Asp His Leu Val Val
         35                  40                  45

Asn Asn Ser Arg Ser Ser Arg Thr Ala Arg Ala Leu Arg His His Lys
     50                  55                  60

Tyr Arg Lys Thr Cys Lys Arg Cys Arg Val Ser Asp Glu Asp Leu Asn
 65                  70                  75                  80

Lys Phe Leu Thr Lys Ala Asn Glu Asp Gln Thr Ser Val Lys Val Lys
                 85                  90                  95

Val Val Ser Ala Pro Thr Arg Thr Lys Lys Ala Met Pro Lys Ser Val
             100                 105                 110

Ala Arg Ala Pro Lys Pro Leu Glu Asn Thr Glu Ala Ala Gln Ala Gln
         115                 120                 125

Pro Ser Gly Ser Lys Phe Ser Pro Ala Ile Pro Val Ser Thr Gln Glu
         130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
             165                 170                 175

Thr Ser Met Ser Ala Pro Val Gln Ala Ser Ala Pro Ala Leu Thr Lys
             180                 185                 190

Ser Gln Thr Asp Arg Leu Glu Val Leu Leu Asn Pro Lys Asp Glu Ile
         195                 200                 205

Ser Leu Asn Ser Gly Lys Pro Phe Arg Glu Leu Glu Ser Glu Leu Leu
     210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                 245                 250                 255

Arg Gly Phe Leu Glu Ile Lys Ser Pro Ile Leu Ile Pro Leu Glu Tyr
             260                 265                 270

Ile Glu Arg Phe Gly Ile Asp Asn Asp Thr Glu Leu Ser Lys Gln Ile
         275                 280                 285

Phe Arg Val Asp Lys Asn Phe Cys Leu Arg Pro Met Leu Ser Pro Asn
         290                 295                 300

Leu Cys Asn Tyr Met Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                 325                 330                 335

Glu His Leu Glu Glu Phe Thr Met Leu Asn Phe Cys Gln Met Gly Ser
             340                 345                 350

Gly Cys Thr Arg Glu Asn Leu Glu Ser Ile Ile Thr Asp Phe Leu Asn
             355                 360                 365

His Leu Gly Ile Asp Phe Lys Ile Val Gly Asp Ser Cys Met Val Tyr
         370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                 405                 410                 415
```

```
Trp Ile Gly Ala Gly Phe Gly Leu Glu Arg Leu Leu Lys Val Lys His
        420             425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 18
<211> LENGTH: 38
<212> TYPE: DNA
<213> ORGANISM: Artificial Sequence
<220> FEATURE:
<223> OTHER INFORMATION: FMT17

<400> SEQUENCE: 18
catgtagatc gaatggacta taaatccgtt cagccggg                       38

<210> SEQ ID NO 19
<211> LENGTH: 38
<212> TYPE: DNA
<213> ORGANISM: Artificial Sequence
<220> FEATURE:
<223> OTHER INFORMATION: FMT18

<400> SEQUENCE: 19
cccggctgaa cggatttata gtccattcga tctacatg                       38

<210> SEQ ID NO 20
<211> LENGTH: 42
<212> TYPE: DNA
<213> ORGANISM: Artificial Sequence
<220> FEATURE:
<223> OTHER INFORMATION: FMT19

<400> SEQUENCE: 20
catgtagatc gaatggactt gcaatccgtt cagccgggtt ag                  42

<210> SEQ ID NO 21
<211> LENGTH: 42
<212> TYPE: DNA
<213> ORGANISM: Artificial Sequence
<220> FEATURE:
<223> OTHER INFORMATION: FMT20

<400> SEQUENCE: 21
ctaacccggc tgaacggatt gcaagtccat tcgatctaca tg                  42

<210> SEQ ID NO 22
<211> LENGTH: 35
<212> TYPE: DNA
<213> ORGANISM: Artificial Sequence
<220> FEATURE:
<223> OTHER INFORMATION: FMT21

<400> SEQUENCE: 22
gtagatcgaa tggactagaa atccgttcag ccggg                          35

<210> SEQ ID NO 23
<211> LENGTH: 35
<212> TYPE: DNA
<213> ORGANISM: Artificial Sequence
<220> FEATURE:
<223> OTHER INFORMATION: FMT22

<400> SEQUENCE: 23
```

```
cccggctgaa cggatttcta gtccattcga tctac                                35
```

<210> SEQ ID NO 24
<211> LENGTH: 42
<212> TYPE: DNA
<213> ORGANISM: Artificial Sequence
<220> FEATURE:
<223> OTHER INFORMATION: FMT23

<400> SEQUENCE: 24

```
catgtagatc gaatggactg ctaatccgtt cagccgggtt ag                        42
```

<210> SEQ ID NO 25
<211> LENGTH: 42
<212> TYPE: DNA
<213> ORGANISM: Artificial Sequence
<220> FEATURE:
<223> OTHER INFORMATION: FMT24

<400> SEQUENCE: 25

```
ctaacccggc tgaacggatt agcagtccat tcgatctaca tg                        42
```

<210> SEQ ID NO 26
<211> LENGTH: 35
<212> TYPE: DNA
<213> ORGANISM: Artificial Sequence
<220> FEATURE:
<223> OTHER INFORMATION: FMT25

<400> SEQUENCE: 26

```
gtagatcgaa tggacttaaa atccgttcag ccggg                                35
```

<210> SEQ ID NO 27
<211> LENGTH: 35
<212> TYPE: DNA
<213> ORGANISM: Artificial Sequence
<220> FEATURE:
<223> OTHER INFORMATION: FMT26

<400> SEQUENCE: 27

```
cccggctgaa cggattttaa gtccattcga tctac                                35
```

<210> SEQ ID NO 28
<211> LENGTH: 35
<212> TYPE: DNA
<213> ORGANISM: Artificial Sequence
<220> FEATURE:
<223> OTHER INFORMATION: FMT27

<400> SEQUENCE: 28

```
gtagatcgaa tggactcaga atccgttcag ccggg                                35
```

<210> SEQ ID NO 29
<211> LENGTH: 35
<212> TYPE: DNA
<213> ORGANISM: Artificial Sequence
<220> FEATURE:
<223> OTHER INFORMATION: FMT28

<400> SEQUENCE: 29

```
cccggctgaa cggattctga gtccattcga tctac                                35
```

<210> SEQ ID NO 30
<211> LENGTH: 35
<212> TYPE: DNA
<213> ORGANISM: Artificial Sequence

```
<220> FEATURE:
<223> OTHER INFORMATION: FMT29

<400> SEQUENCE: 30
gtagatcgaa tggactcata atccgttcag ccggg                              35

<210> SEQ ID NO 31
<211> LENGTH: 35
<212> TYPE: DNA
<213> ORGANISM: Artificial Sequence
<220> FEATURE:
<223> OTHER INFORMATION: FMT30

<400> SEQUENCE: 31
cccggctgaa cggattatga gtccattcga tctac                              35

<210> SEQ ID NO 32
<211> LENGTH: 42
<212> TYPE: DNA
<213> ORGANISM: Artificial Sequence
<220> FEATURE:
<223> OTHER INFORMATION: FMT31

<400> SEQUENCE: 32
catgtagatc gaatggactt ttaatccgtt cagccgggtt ag                      42

<210> SEQ ID NO 33
<211> LENGTH: 42
<212> TYPE: DNA
<213> ORGANISM: Artificial Sequence
<220> FEATURE:
<223> OTHER INFORMATION: FMT32

<400> SEQUENCE: 33
ctaacccggc tgaacggatt aaaagtccat tcgatctaca tg                      42

<210> SEQ ID NO 34
<211> LENGTH: 35
<212> TYPE: DNA
<213> ORGANISM: Artificial Sequence
<220> FEATURE:
<223> OTHER INFORMATION: MAM01

<400> SEQUENCE: 34
gtagatcgaa tggactcata atccgttcag ccggg                              35

<210> SEQ ID NO 35
<211> LENGTH: 35
<212> TYPE: DNA
<213> ORGANISM: Artificial Sequence
<220> FEATURE:
<223> OTHER INFORMATION: MAM02

<400> SEQUENCE: 35
cccggctgaa cggattatga gtccattcga tctac                              35

<210> SEQ ID NO 36
<211> LENGTH: 31
<212> TYPE: DNA
<213> ORGANISM: Artificial Sequence
<220> FEATURE:
<223> OTHER INFORMATION: MAM03

<400> SEQUENCE: 36
gatcgaatgg actcacaatc cgttcagccg g                                  31
```

<210> SEQ ID NO 37
<211> LENGTH: 31
<212> TYPE: DNA
<213> ORGANISM: Artificial Sequence
<220> FEATURE:
<223> OTHER INFORMATION: MAM04

<400> SEQUENCE: 37
ccggctgaac ggattgtgag tccattcgat c                          31

<210> SEQ ID NO 38
<211> LENGTH: 30
<212> TYPE: DNA
<213> ORGANISM: Artificial Sequence
<220> FEATURE:
<223> OTHER INFORMATION: MAM05

<400> SEQUENCE: 38
gatcgaatgg actcttaatc cgttcagccg                             30

<210> SEQ ID NO 39
<211> LENGTH: 30
<212> TYPE: DNA
<213> ORGANISM: Artificial Sequence
<220> FEATURE:
<223> OTHER INFORMATION: MAM06

<400> SEQUENCE: 39
cggctgaacg gattaagagt ccattcgatc                             30

<210> SEQ ID NO 40
<211> LENGTH: 30
<212> TYPE: DNA
<213> ORGANISM: Artificial Sequence
<220> FEATURE:
<223> OTHER INFORMATION: MAM07

<400> SEQUENCE: 40
gatcgaatgg actctcaatc cgttcagccg                             30

<210> SEQ ID NO 41
<211> LENGTH: 30
<212> TYPE: DNA
<213> ORGANISM: Artificial Sequence
<220> FEATURE:
<223> OTHER INFORMATION: MAM08

<400> SEQUENCE: 41
cggctgaacg gattgagagt ccattcgatc                             30

<210> SEQ ID NO 42
<211> LENGTH: 33
<212> TYPE: DNA
<213> ORGANISM: Artificial Sequence
<220> FEATURE:
<223> OTHER INFORMATION: MAM09

<400> SEQUENCE: 42
gtagatcgaa tggactgtaa atccgttcag ccg                         33

<210> SEQ ID NO 43
<211> LENGTH: 33
<212> TYPE: DNA
<213> ORGANISM: Artificial Sequence
<220> FEATURE:
<223> OTHER INFORMATION: MAM10

<400> SEQUENCE: 43
cggctgaacg gatttacagt ccattcgatc tac    33

<210> SEQ ID NO 44
<211> LENGTH: 30
<212> TYPE: DNA
<213> ORGANISM: Artificial Sequence
<220> FEATURE:
<223> OTHER INFORMATION: MAM11

<400> SEQUENCE: 44
gatcgaatgg actccaaatc cgttcagccg    30

<210> SEQ ID NO 45
<211> LENGTH: 30
<212> TYPE: DNA
<213> ORGANISM: Artificial Sequence
<220> FEATURE:
<223> OTHER INFORMATION: MAM12

<400> SEQUENCE: 45
cggctgaacg gatttggagt ccattcgatc    30

<210> SEQ ID NO 46
<211> LENGTH: 1587
<212> TYPE: DNA
<213> ORGANISM: Artificial Sequence
<220> FEATURE:
<223> OTHER INFORMATION: Drosophila GFP-amber-mCherry-HA

<400> SEQUENCE: 46
atggtgtcca agggcgagga gctgtttacc ggcgtggtgc ccattctggt ggagctggat    60
ggcgacgtga acggccacaa gttcagcgtg tccggcgagg gcgagggcga cgccacctat    120
ggaaagctga ccctgaagtt catctgcacc accggcaagc tgcccgtgcc atggccaacc    180
ctcgtgacca ccctgaccta tggcgtgcag tgcttcagcc gctaccccga tcacatgaag    240
cagcacgatt tcttcaagag cgccatgccc gagggctacg tgcaggagcg caccatcttt    300
ttcaaggatg acggcaacta caagacccgc gccgaagtga agttcgaggg cgataccctc    360
gtgaaccgca tcgagctgaa gggcatcgat ttcaaggagg atggaaacat cctgggccac    420
aagctggagt acaactacaa cagccacaac gtgtacatca tggccgacaa gcagaagaac    480
ggcatcaaag tgaacttcaa gatccgccac aacatcgagg atggcagcgt gcagctggcc    540
gatcactacc agcagaacac cccaatcggc gacggcccag tgctgctgcc cgataaccat    600
tacctgagca cccagagcgc cctgagcaag gaccccaacg agaagcgcga ccacatggtg    660
ctgctggagt ttgtgaccgc cgccggcatt accctgggca tggatgagct gtacaagcgc    720
gcccagatcc acgatctggt gtaggtggga ggatcgaccc gcgtgtcgaa gggcgaggag    780
gataacatgg ccatcatcaa ggagttcatg cgcttcaagg tgcacatgga gggctccgtg    840
aatggacacg agttcgagat tgagggcgag ggcgagggac gcccatatga gggaacccag    900
accgccaagc tgaaagtgac caagggcgga cccctgccct tcgcctggga tattctgagc    960
ccccagttta tgtacggcag caaggcctac gtgaagcacc ccgccgatat ccccgattac    1020
ctgaagctga gcttcccaga gggcttcaag tgggagcgcg tgatgaattt cgaggacggc    1080
ggagtcgtga ccgtgaccca ggatagcagt ttgcaggatg gcgagttcat ctacaaagtg    1140
aagctgcgcg gcaccaactt cccgtccgat ggcccagtga tgcagaagaa gaccatgggc    1200

```
tgggaggcca gcagcgagcg catgtatcca gaggatggcg ccctgaaggg cgagatcaag    1260
cagcgcctga agctgaagga tggcggccac tacgatgccg aagtgaagac cacctacaag    1320
gccaagaagc cggtgcagct gccaggcgcc tacaatgtga acatcaagct ggatatcacc    1380
tcccacaacg aggactacac catcgtggag cagtatgagc gcgccgaggg ccgccatagt    1440
accggcggaa tggacgagct gtataagatg taccccctacg atgtgcccga ttacgccgag    1500
cagaagctga tctccgagga ggacctgcac catcaccacc accacggaag tggcagcggc    1560
tccccaaaga agaagcgcaa ggtgtaa                                        1587

<210> SEQ ID NO 47
<211> LENGTH: 527
<212> TYPE: PRT
<213> ORGANISM: Artificial Sequence
<220> FEATURE:
<223> OTHER INFORMATION: Drosophila GFP-amber-mCherry-HA

<400> SEQUENCE: 47
```

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Arg
225                 230                 235                 240

Ala Gln Ile His Asp Leu Val Val Gly Ser Thr Arg Val Ser Lys
                245                 250                 255

Gly Glu Glu Asp Asn Met Ala Ile Ile Lys Glu Phe Met Arg Phe Lys
            260                 265                 270

Val His Met Glu Gly Ser Val Asn Gly His Glu Phe Glu Ile Glu Gly
        275                 280                 285

Glu Gly Glu Gly Arg Pro Tyr Glu Gly Thr Gln Thr Ala Lys Leu Lys

|   |   |   |   |   | 290 |   |   |   |   | 295 |   |   |   |   | 300 |
|---|---|---|---|---|---|---|---|---|---|---|---|---|---|---|---|
| Val | Thr | Lys | Gly | Gly | Pro | Leu | Pro | Phe | Ala | Trp | Asp | Ile | Leu | Ser | Pro |
| 305 |   |   |   |   | 310 |   |   |   |   | 315 |   |   |   |   | 320 |
| Gln | Phe | Met | Tyr | Gly | Ser | Lys | Ala | Tyr | Val | Lys | His | Pro | Ala | Asp | Ile |
|   |   |   |   | 325 |   |   |   |   | 330 |   |   |   |   | 335 |   |
| Pro | Asp | Tyr | Leu | Lys | Leu | Ser | Phe | Pro | Glu | Gly | Phe | Lys | Trp | Glu | Arg |
|   |   |   | 340 |   |   |   |   | 345 |   |   |   |   | 350 |   |   |
| Val | Met | Asn | Phe | Glu | Asp | Gly | Gly | Val | Val | Thr | Val | Thr | Gln | Asp | Ser |
|   |   | 355 |   |   |   | 360 |   |   |   |   | 365 |   |   |   |   |
| Ser | Leu | Gln | Asp | Gly | Glu | Phe | Ile | Tyr | Lys | Val | Lys | Leu | Arg | Gly | Thr |
|   | 370 |   |   |   |   | 375 |   |   |   |   | 380 |   |   |   |   |
| Asn | Phe | Pro | Ser | Asp | Gly | Pro | Val | Met | Gln | Lys | Lys | Thr | Met | Gly | Trp |
| 385 |   |   |   |   | 390 |   |   |   |   | 395 |   |   |   |   | 400 |
| Glu | Ala | Ser | Ser | Glu | Arg | Met | Tyr | Pro | Glu | Asp | Gly | Ala | Leu | Lys | Gly |
|   |   |   |   | 405 |   |   |   |   | 410 |   |   |   |   | 415 |   |
| Glu | Ile | Lys | Gln | Arg | Leu | Lys | Leu | Lys | Asp | Gly | Gly | His | Tyr | Asp | Ala |
|   |   |   | 420 |   |   |   |   | 425 |   |   |   |   | 430 |   |   |
| Glu | Val | Lys | Thr | Thr | Tyr | Lys | Ala | Lys | Lys | Pro | Val | Gln | Leu | Pro | Gly |
|   |   |   | 435 |   |   |   |   | 440 |   |   |   |   | 445 |   |   |
| Ala | Tyr | Asn | Val | Asn | Ile | Lys | Leu | Asp | Ile | Thr | Ser | His | Asn | Glu | Asp |
|   |   |   |   | 450 |   |   |   |   | 455 |   |   |   |   | 460 |   |
| Tyr | Thr | Ile | Val | Glu | Gln | Tyr | Glu | Arg | Ala | Glu | Gly | Arg | His | Ser | Thr |
| 465 |   |   |   |   | 470 |   |   |   |   | 475 |   |   |   |   | 480 |
| Gly | Gly | Met | Asp | Glu | Leu | Tyr | Lys | Met | Tyr | Pro | Tyr | Asp | Val | Pro | Asp |
|   |   |   | 485 |   |   |   |   | 490 |   |   |   |   | 495 |   |   |
| Tyr | Ala | Glu | Gln | Lys | Leu | Ile | Ser | Glu | Glu | Asp | Leu | His | His | His | His |
|   |   |   | 500 |   |   |   |   | 505 |   |   |   |   | 510 |   |   |
| His | His | Gly | Ser | Gly | Ser | Gly | Ser | Pro | Lys | Lys | Lys | Arg | Lys | Val |   |
|   |   |   | 515 |   |   |   |   | 520 |   |   |   |   | 525 |   |   |